US006648820B1

(12) United States Patent
Sarel

(10) Patent No.: US 6,648,820 B1
(45) Date of Patent: Nov. 18, 2003

(54) MEDICAL CONDITION SENSING SYSTEM

(75) Inventor: Oded Sarel, Even-Yehuda (IL)

(73) Assignee: Home-Medicine (USA), Inc., Even-Yehuda (IL)

( * ) Notice: Subject to any disclaimer, the term of this patent is extended or adjusted under 35 U.S.C. 154(b) by 0 days.

(21) Appl. No.: 09/428,430

(22) Filed: Oct. 27, 1999

(51) Int. Cl.$^7$ ............................................. A61B 5/00
(52) U.S. Cl. ........................ 600/300; 600/301; 128/903; 128/904; 128/920; 705/4
(58) Field of Search ............................... 600/300–301, 600/544–545; 128/903–904, 920–925, 897–898; 705/2–4; 702/19; 607/30, 32, 60

(56) References Cited

U.S. PATENT DOCUMENTS

| | | | |
|---|---|---|---|
| 3,688,413 A | 9/1972 | Harte | 35/9 E |
| 3,786,510 A | 1/1974 | Hodges | 346/33 ME |
| 4,216,462 A | 8/1980 | McGrath et al. | 340/150 |
| 4,284,847 A | 8/1981 | Besserman | 179/1 N |
| 4,367,752 A | 1/1983 | Jimenez et al. | 128/689 |
| 4,489,610 A | 12/1984 | Slavin | 73/585 |
| 4,561,449 A | 12/1985 | Hu et al. | 128/746 |
| 4,671,772 A | 6/1987 | Slade et al. | 434/219 |
| 4,740,072 A | 4/1988 | Griffin et al. | 351/243 |
| 4,768,074 A | 8/1988 | Yoshida et al. | 357/34 |
| 4,803,625 A | 2/1989 | Fu et al. | 364/413.03 |
| 5,002,491 A | 3/1991 | Abrahaneson et al. | 434/322 |
| 5,008,853 A | 4/1991 | Bly et al. | 364/900 |
| 5,019,974 A | 5/1991 | Beckers | 364/413.02 |
| 5,103,408 A | 4/1992 | Greenberg et al. | 364/550 |
| 5,197,332 A | 3/1993 | Shennib | 73/585 |
| 5,211,564 A | 5/1993 | Martinez et al. | 434/323 |
| 5,267,865 A | 12/1993 | Lee et al. | 434/350 |
| 5,283,856 A | 2/1994 | Gross et al. | 395/51 |
| 5,306,154 A | 4/1994 | Ujita et al. | 434/218 |
| 5,310,349 A | 5/1994 | Daniels et al. | 434/350 |
| 5,422,690 A | 6/1995 | Rothberg et al. | 351/209 |

(List continued on next page.)

FOREIGN PATENT DOCUMENTS

| | | |
|---|---|---|
| IL | 105547 | 4/1993 |
| WO | WO 98/02083 | 1/1998 |

OTHER PUBLICATIONS

"The health.net Industry—The Convergence of Healthcare and the Internet", Jun. 8, 1999, pp. 1–38, Fitzgibbons, Stephen et al.

(List continued on next page.)

Primary Examiner—Max F. Hindenburg
Assistant Examiner—Michael Astorino
(74) Attorney, Agent, or Firm—G. E. Ehrlich Ltd.

(57) ABSTRACT

This invention discloses a medical condition sensing system including a multiplicity of general purpose computers disposed in user locations and being connected via a computer network to at least one controller computer remote from at least one of the user locations, personal parameter measuring software resident on at least one of the multiplicity of general purpose computers and the at least one controller computer for measuring at least one personal parameter of at least one user, personal parameter reference generating software resident on at least one of the multiplicity of general purpose computers and the at least one controller computer for establishing a reference for the at least one personal parameter, and personal parameter comparison software resident on at least one of said multiplicity of general purpose computers and the at least one controller computer for comparing at least one currently measured personal parameter with a corresponding reference and providing a comparison output.

A method for medical condition sensing is also disclosed.

108 Claims, 52 Drawing Sheets

U.S. PATENT DOCUMENTS

| | | | | |
|---|---|---|---|---|
| 5,451,162 | A | 9/1995 | Parsons | 434/16 |
| 5,473,537 | A | 12/1995 | Glazer et al. | 364/419.2 |
| 5,517,405 | A | 5/1996 | McAndrew et al. | 364/401 |
| 5,542,420 | A | 8/1996 | Goldman et al. | 128/630 |
| 5,549,117 | A | 8/1996 | Tacklind et al. | 128/716 |
| 5,553,609 | A | 9/1996 | Chen et al. | 128/630 |
| 5,619,991 | A | 4/1997 | Sloane | 128/630 |
| 5,647,834 | A | 7/1997 | Ron | 600/23 |
| 5,677,979 | A | 10/1997 | Squicciarini et al. | 386/46 |
| 5,715,823 | A | 2/1998 | Wood et al. | 128/660.01 |
| 5,758,652 | A | 6/1998 | Nikolic | 128/673 |
| 5,769,074 | A | 6/1998 | Barnhill et al. | 128/630 |
| 5,791,342 | A | 8/1998 | Woodard | 128/630 |
| 5,791,908 | A | 8/1998 | Gillio | 434/262 |
| 5,810,747 | A | 9/1998 | Brudny et al. | 600/595 |
| 5,811,681 | A | 9/1998 | Braun et al. | 73/585 |
| 5,827,180 | A | 10/1998 | Goodman | 600/300 |
| 5,840,018 | A | 11/1998 | Michaeli | 600/300 |
| 5,842,975 | A | 12/1998 | Illyes et al. | 600/300 |
| 5,842,977 | A | 12/1998 | Lesho et al. | 600/300 |
| 5,848,975 | A | 12/1998 | Phillips | 600/532 |
| 5,851,186 | A | 12/1998 | Wood et al. | 600/437 |
| 5,855,550 | A | 1/1999 | Lai et al. | 600/300 |
| 5,859,972 | A | 1/1999 | Subramaniam et al. | 395/200.33 |
| 5,865,733 | A | 2/1999 | Malinouskas et al. | 600/300 |
| 5,868,134 | A | 2/1999 | Sugiyama et al. | 128/630 |
| 5,868,135 | A | 2/1999 | Kaufman et al. | 128/630 |
| 5,868,669 | A | 2/1999 | Iliff | 600/300 |
| 5,873,369 | A | 2/1999 | Laniado et al. | 128/903 |
| 5,879,292 | A | 3/1999 | Sternberg et al. | 600/300 |
| 5,892,570 | A | 4/1999 | Stevens | 351/237 |
| 5,895,354 | A | 4/1999 | Simmons | 600/301 |
| 5,897,493 | A | 4/1999 | Brown | 600/300 |
| 5,902,234 | A | 5/1999 | Webb | 600/300 |
| 5,906,208 | A | 5/1999 | Ishikawa et al. | 128/898 |
| 5,907,291 | A | 5/1999 | Chen et al. | 340/870.16 |
| 5,928,160 | A * | 7/1999 | Clark et al. | 600/559 |
| 5,961,446 | A * | 10/1999 | Beller et al. | 600/300 |
| 5,978,292 | A | 11/1999 | Lim | 365/201 |
| 6,073,046 | A * | 6/2000 | Patel et al. | 128/904 |
| 6,135,951 | A * | 10/2000 | Richardson et al. | 600/300 |
| 6,168,563 | B1 * | 1/2001 | Brown | 128/904 |
| 6,206,829 | B1 * | 3/2001 | Iliff | 600/300 |
| 6,295,506 | B1 * | 9/2001 | Heinonen et al. | 702/104 |
| 6,302,844 | B1 * | 10/2001 | Walker et al. | 600/300 |

OTHER PUBLICATIONS

BACS Profile: Revolutionizing Medical Data Collection & Management, pp. 1–2.

BACS Automated Self Operated Audiometer, Model 101 (Product Description), pp. 1–2.

Panasonic Vital Signs Box (Product Description), Matsushita Electric Industrial Co., Ltd. p. 1, Dec. 6, 1999.

BACS AVAT Model 201: Automated Self–Operated Vision Tester, pp. 1–2.

* cited by examiner

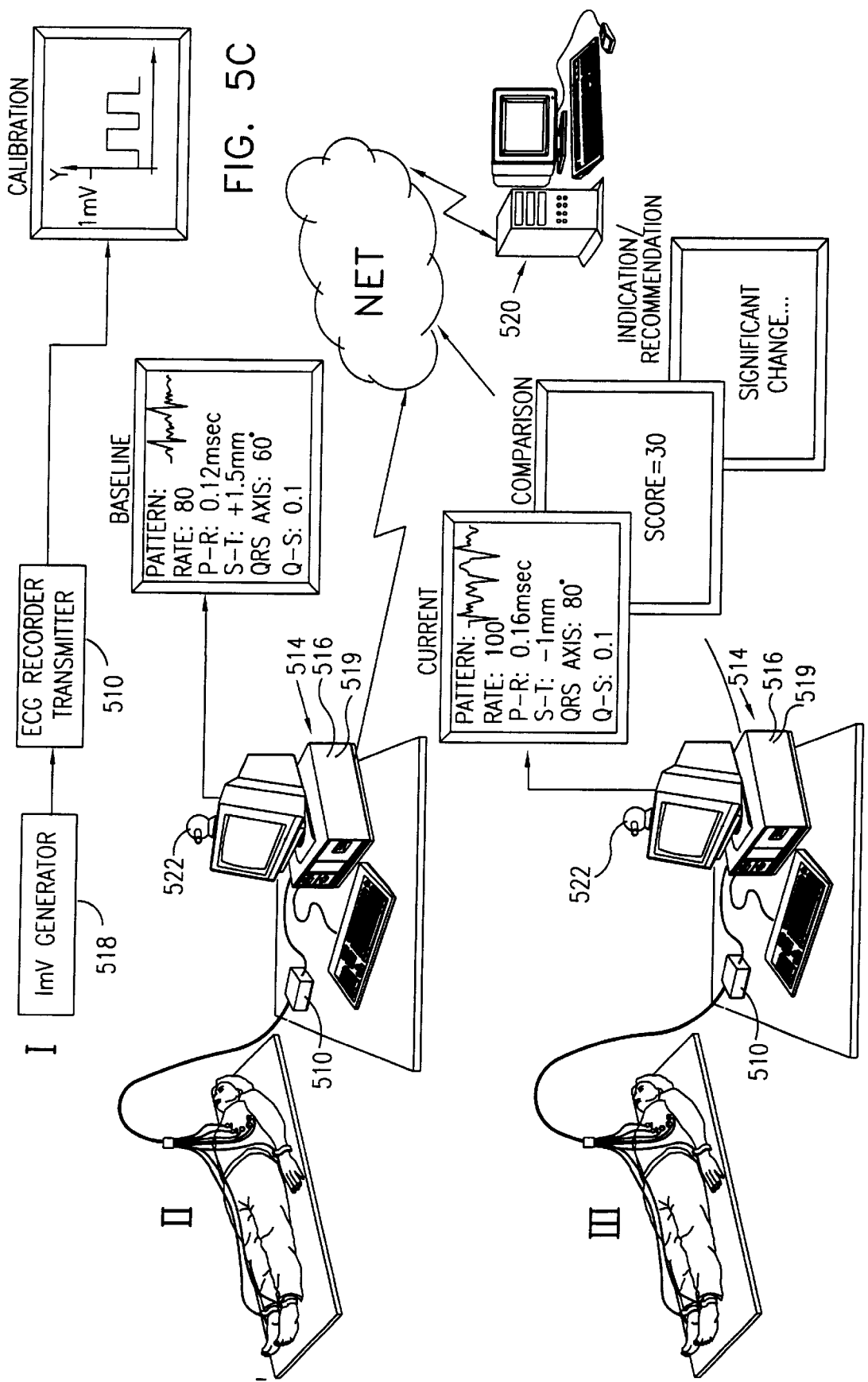

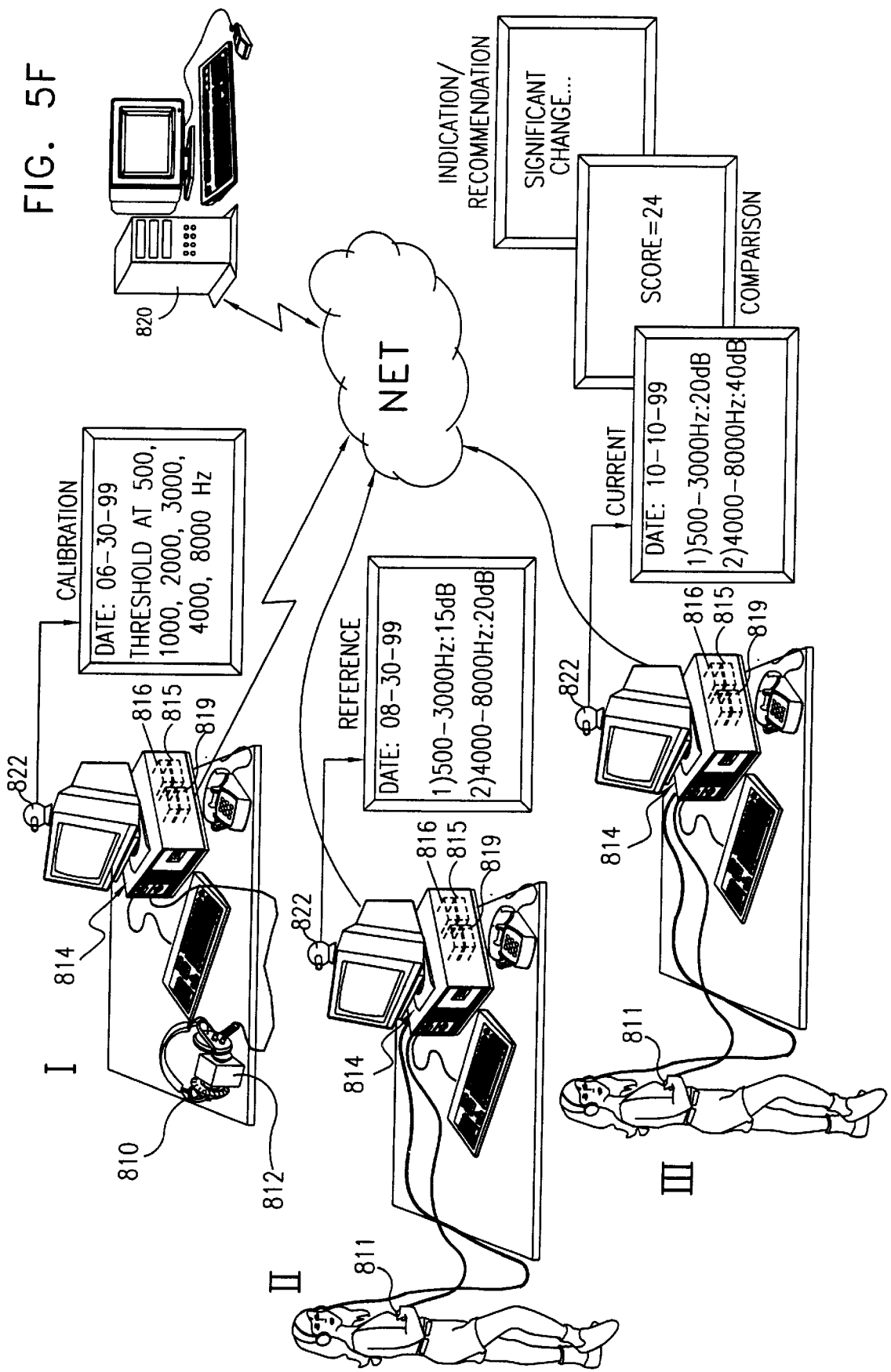

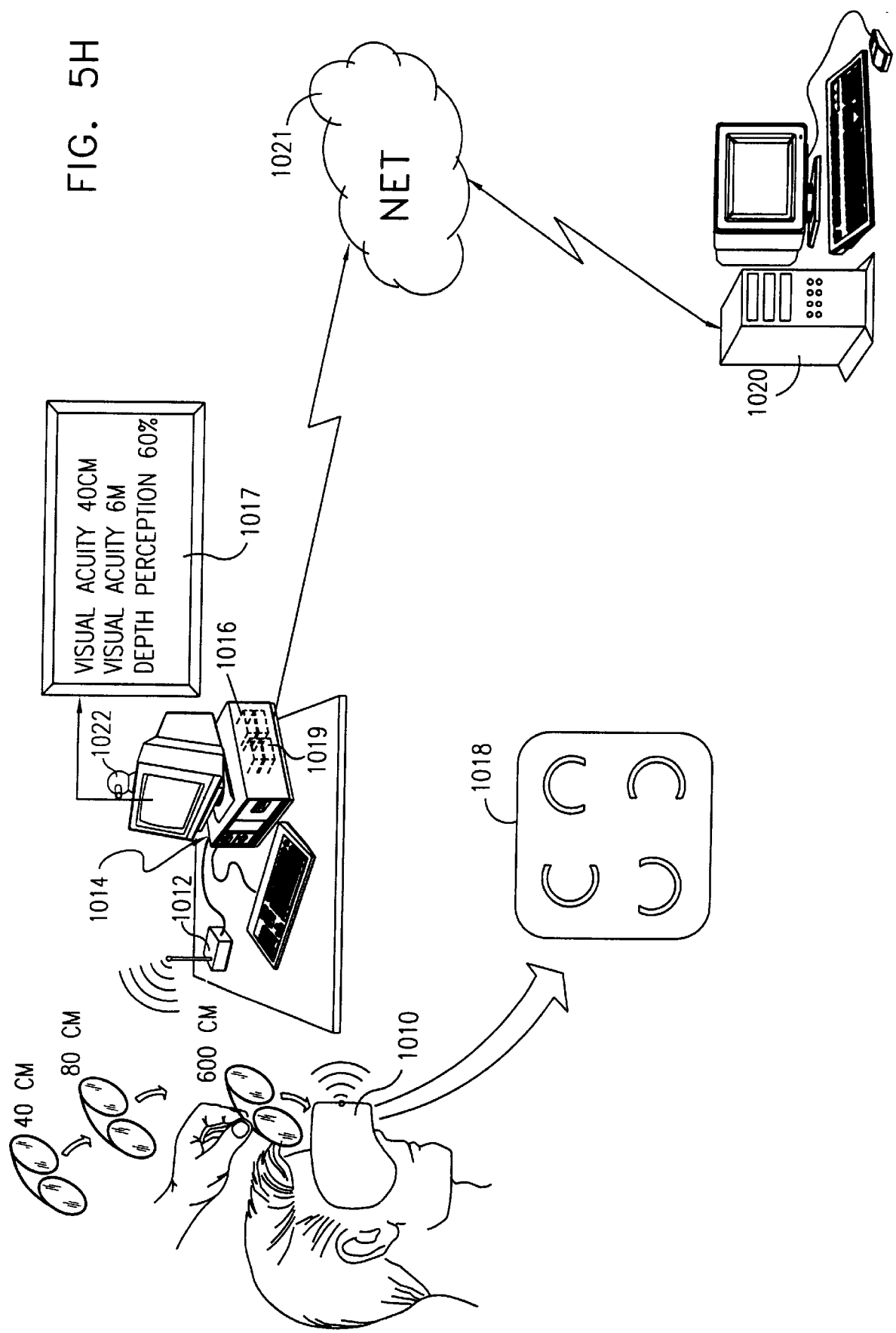

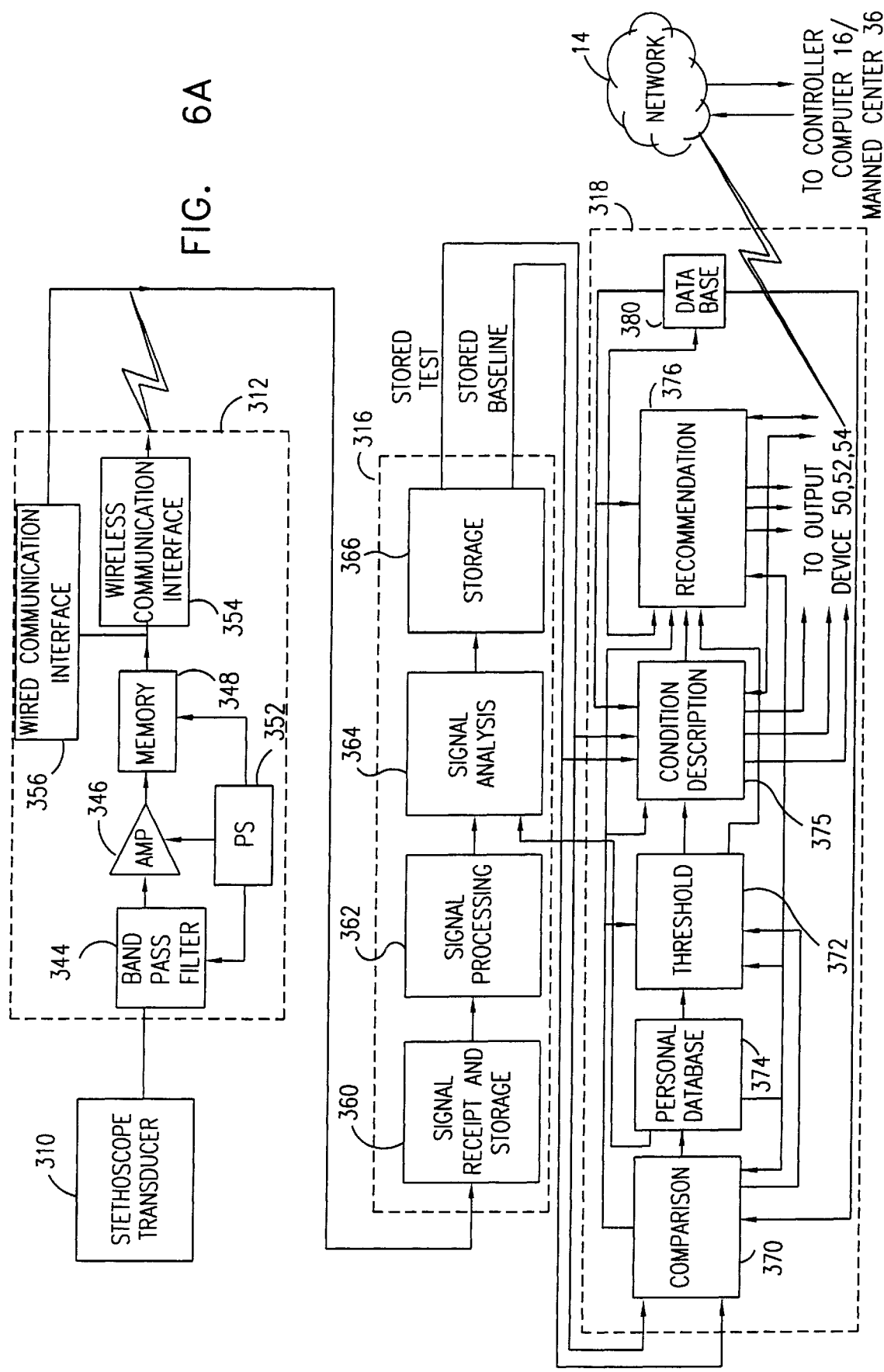

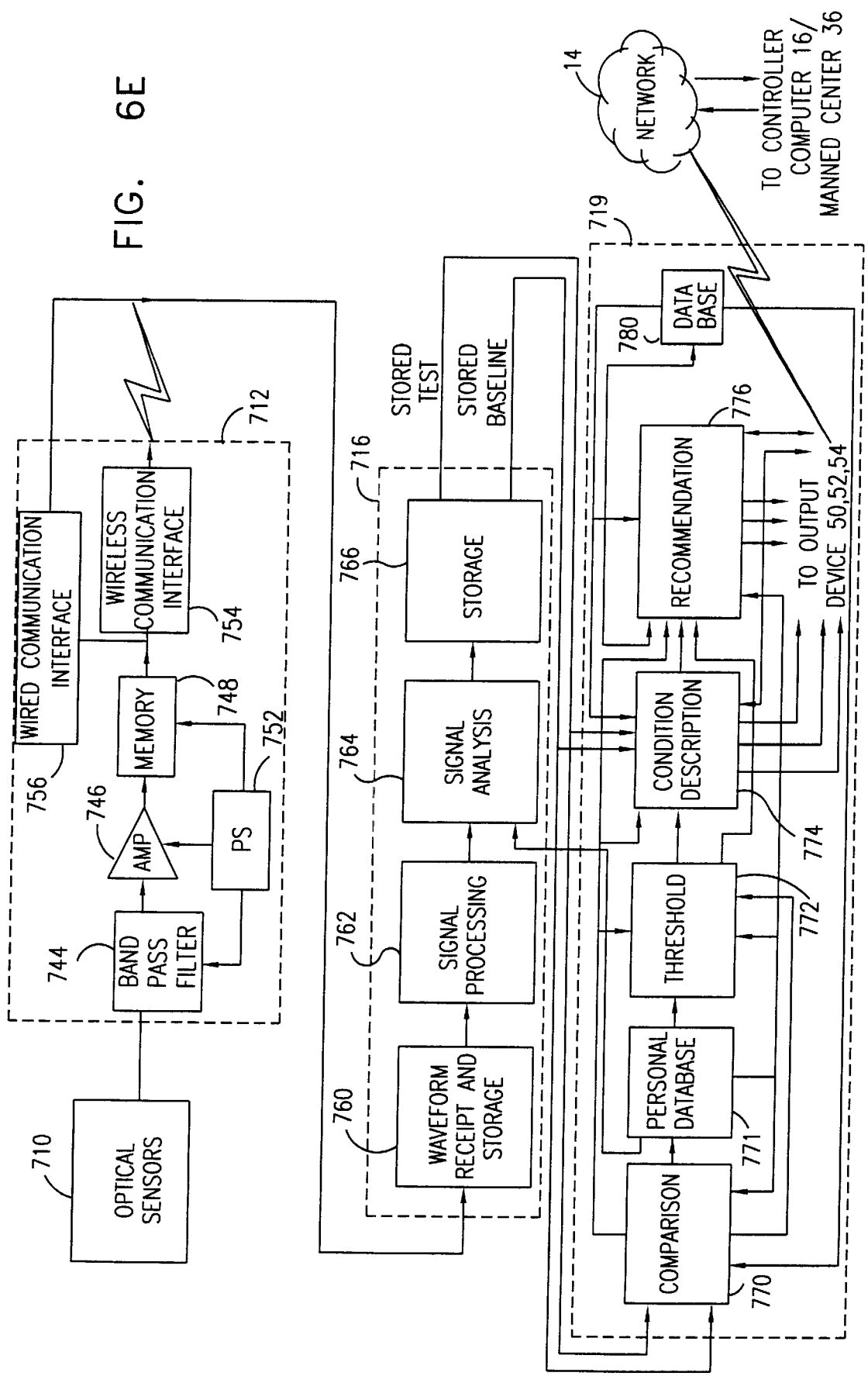

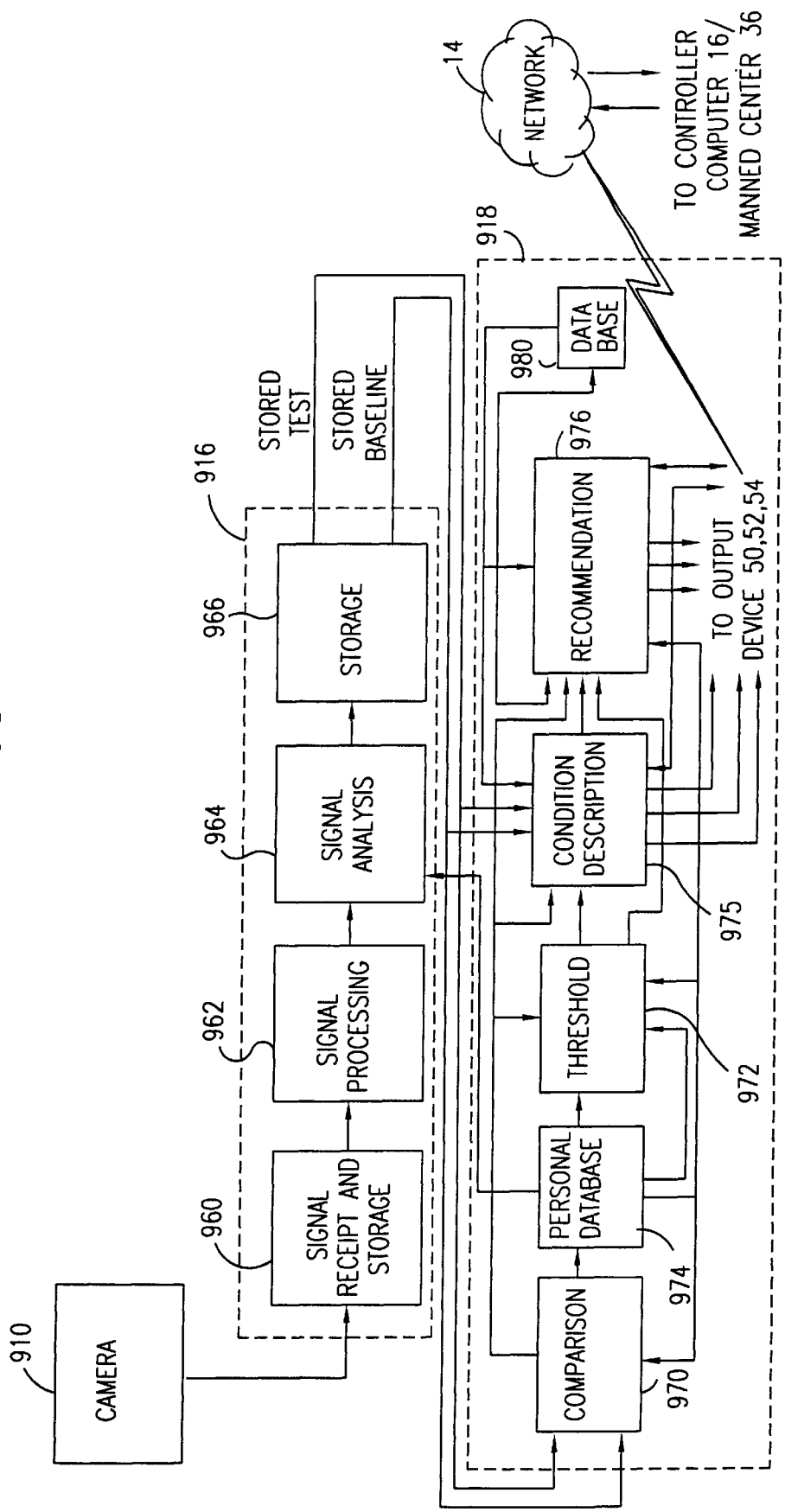

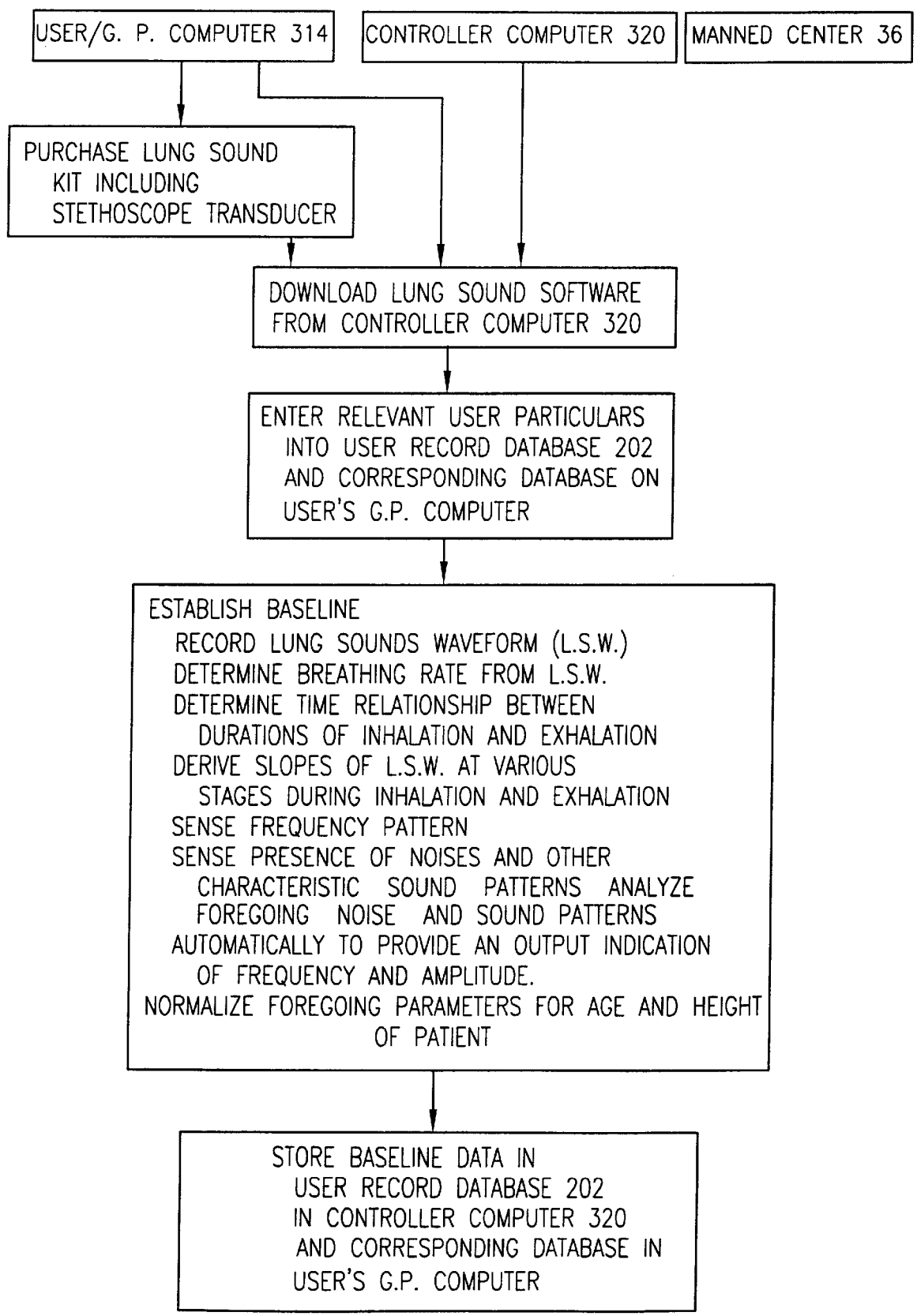

FIG. 7A(2)
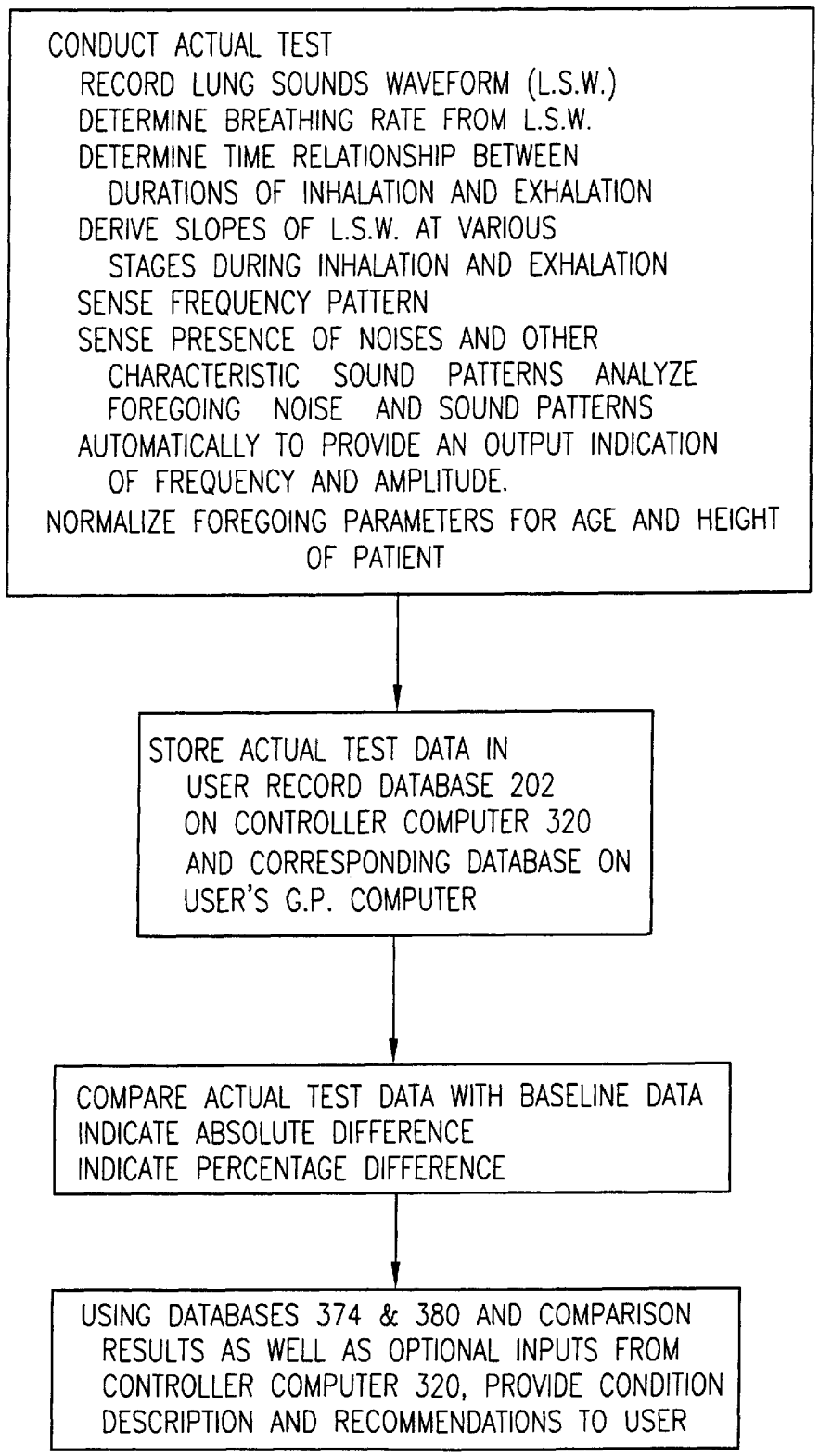

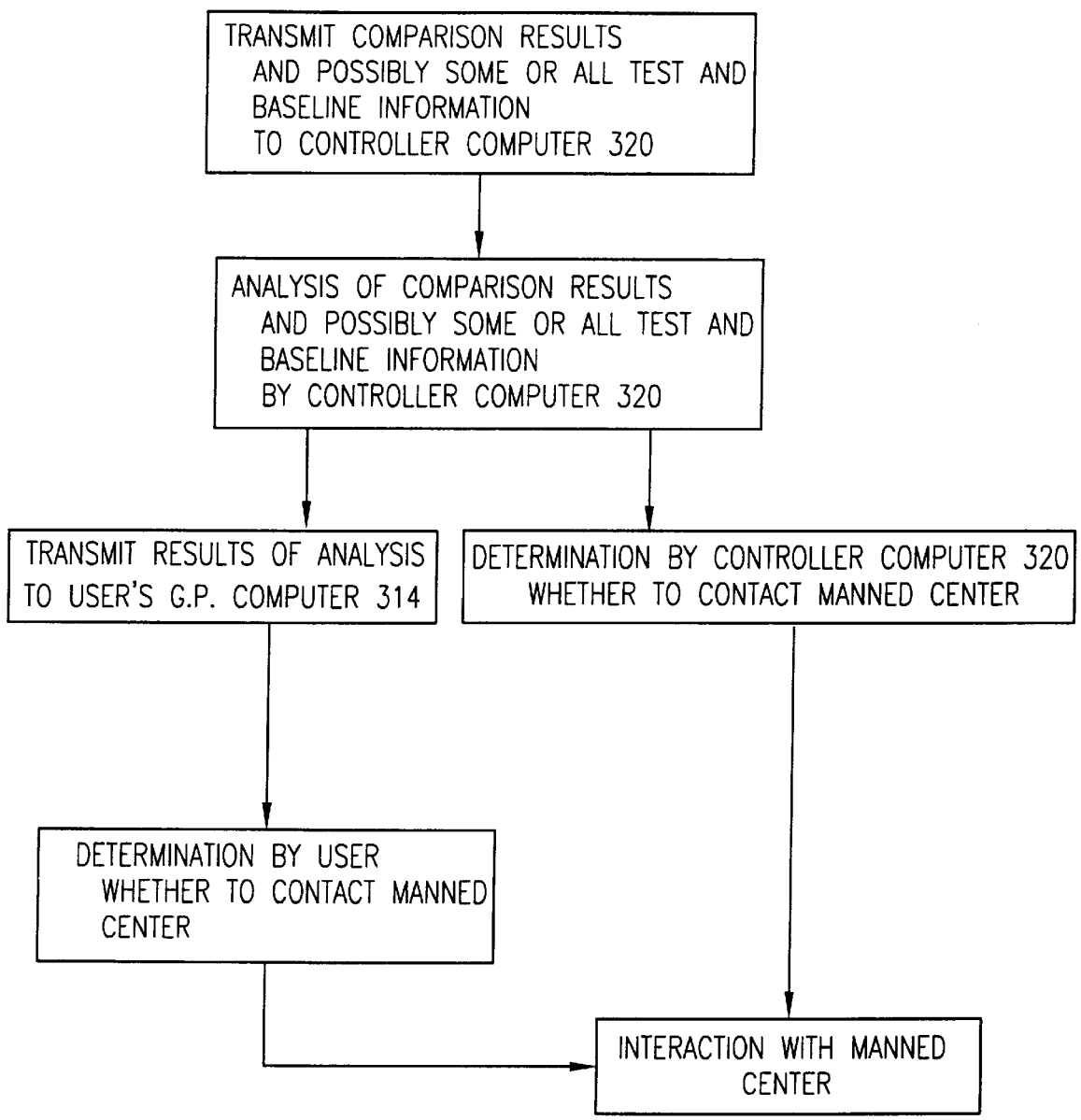
FIG. 7A(3)

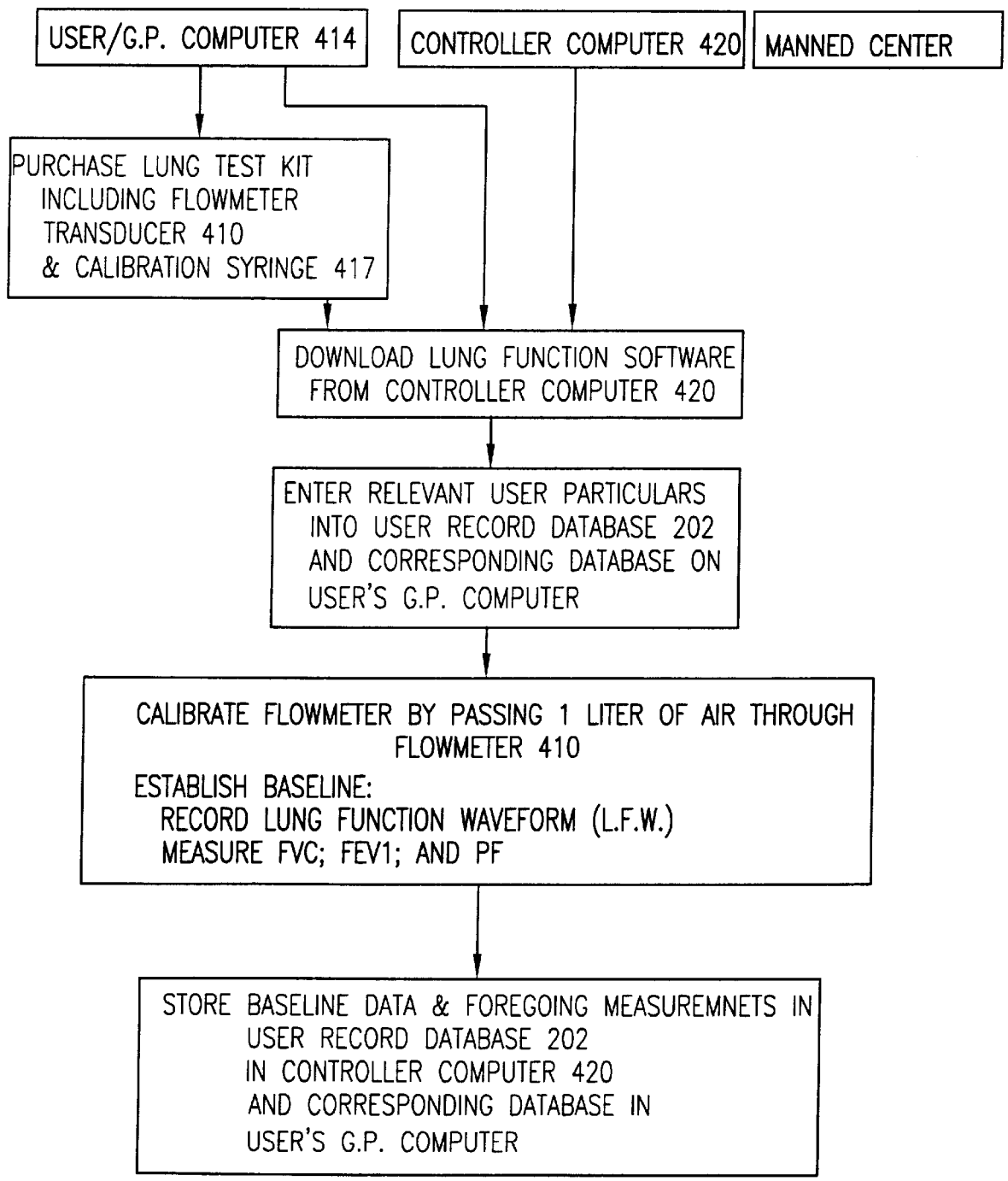
FIG. 7B(1)

FIG. 7B(2)
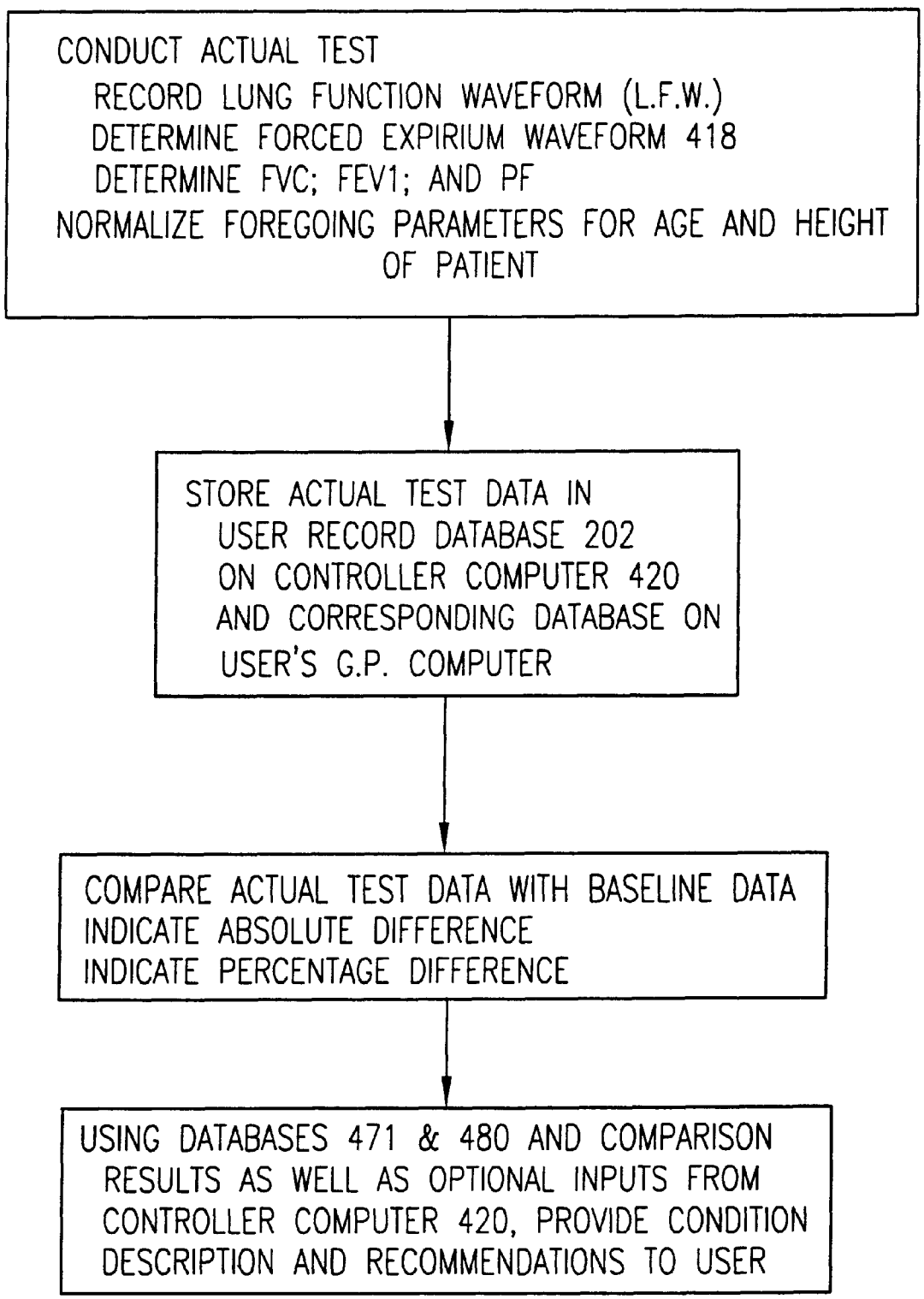

FIG. 7B(3)
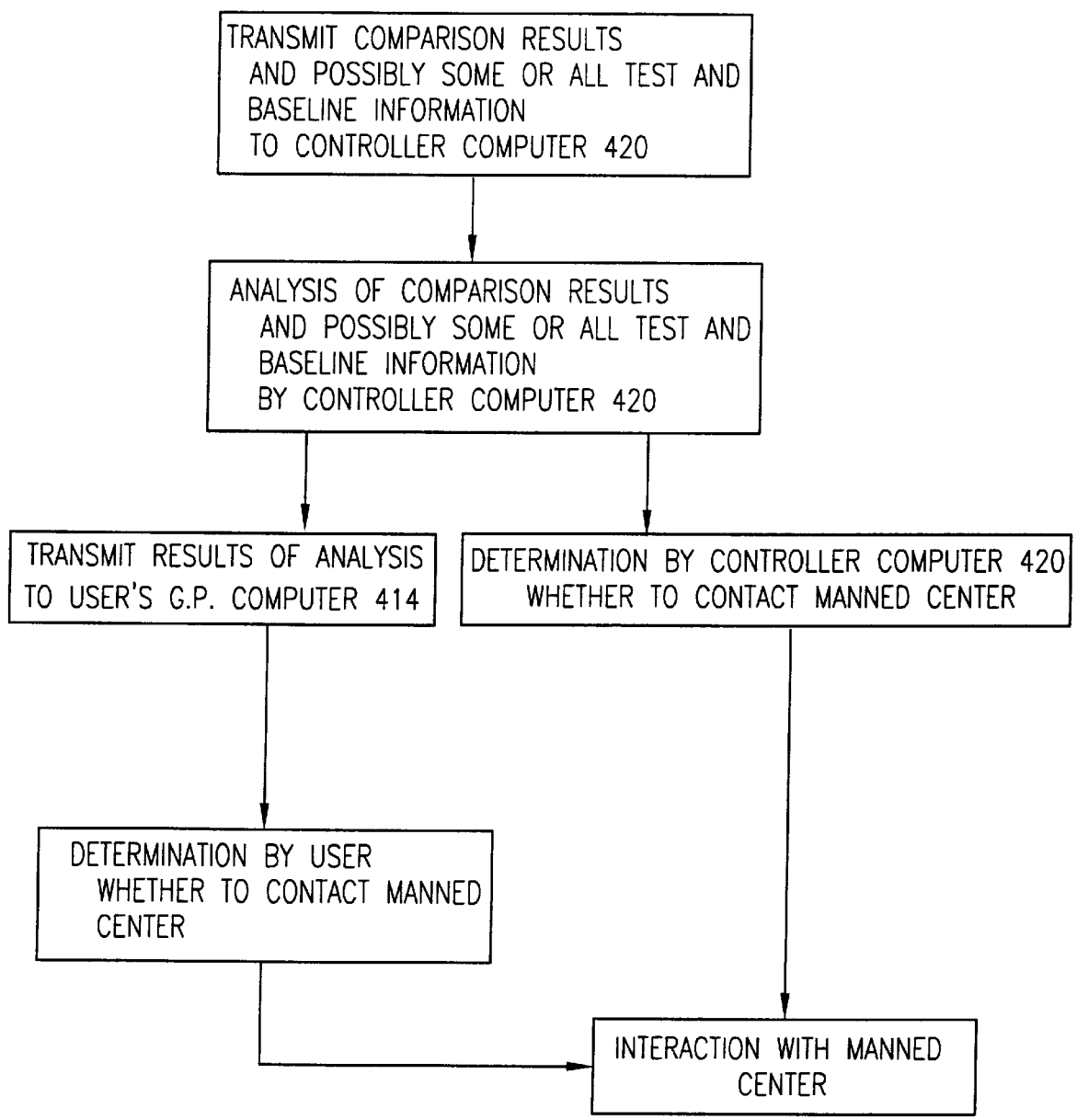

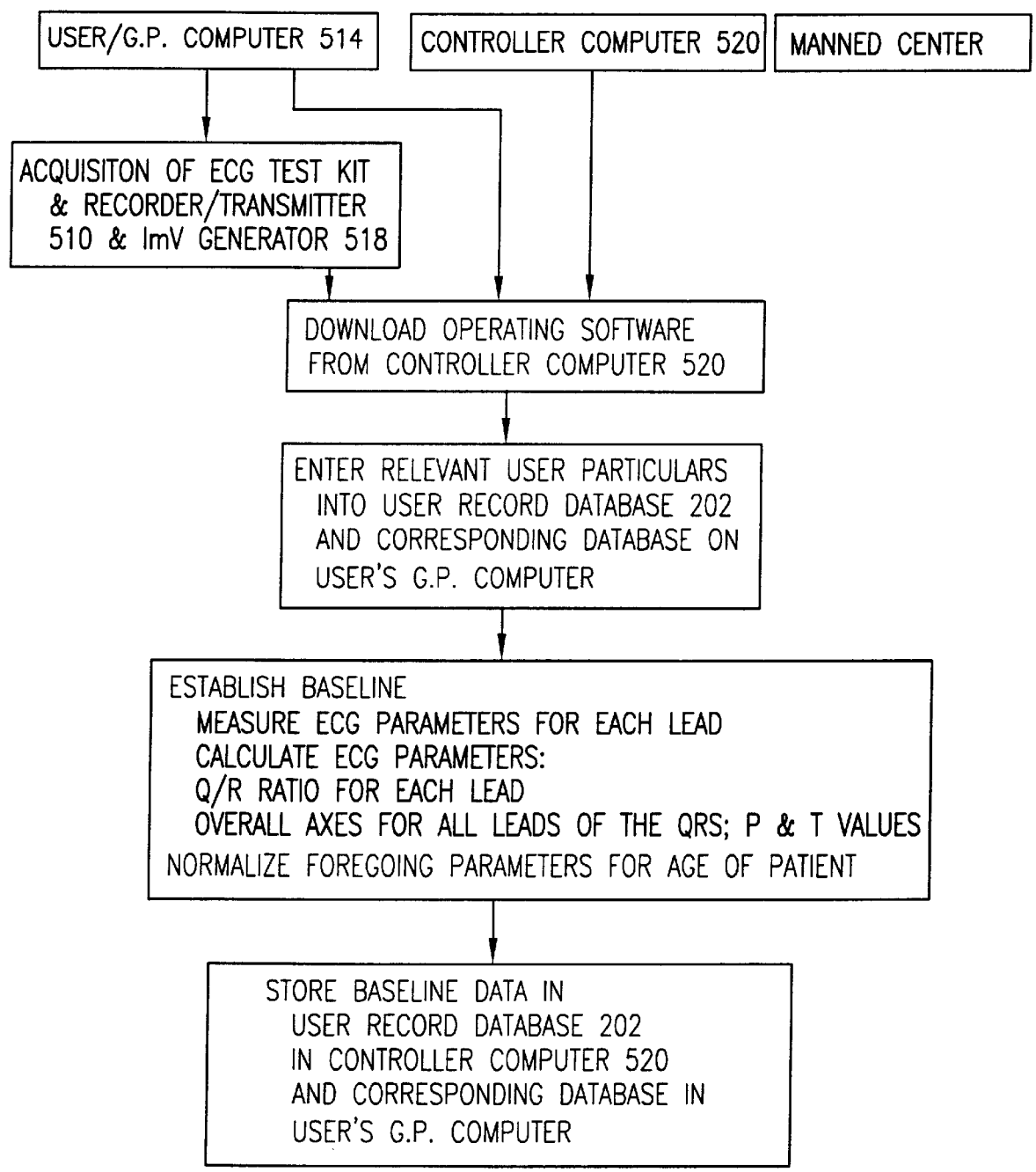

FIG. 7C(2)
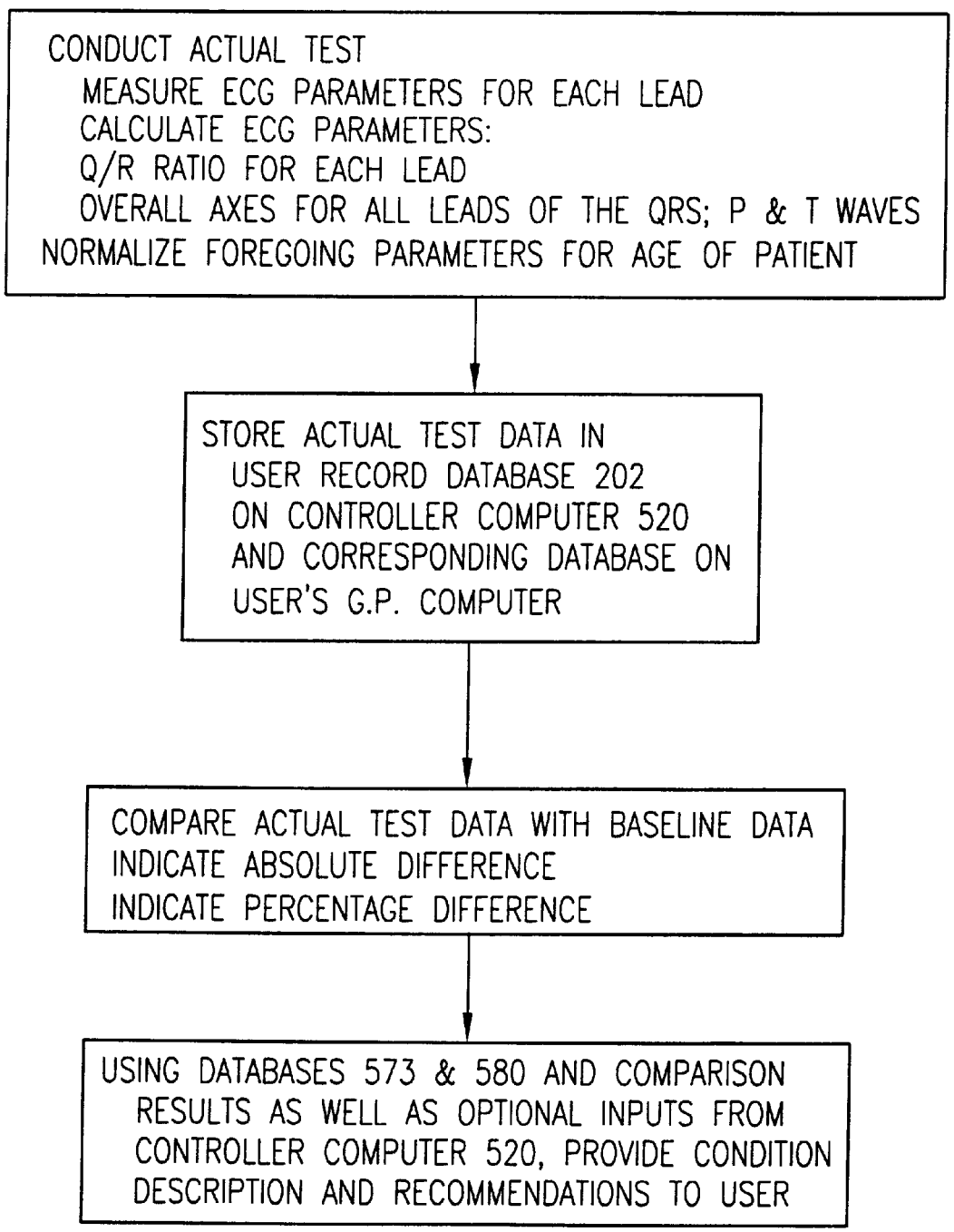

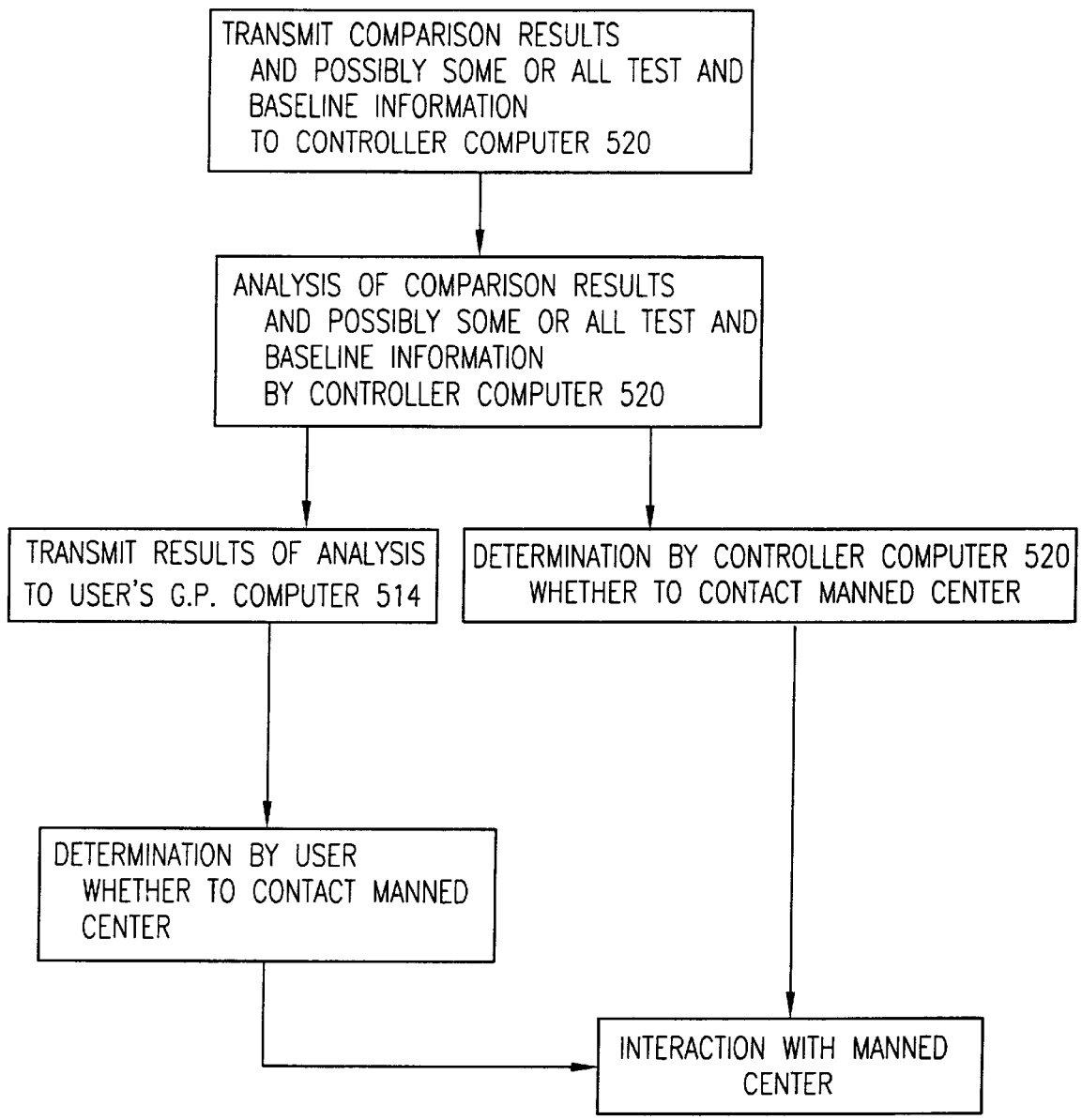
FIG. 7C(3)

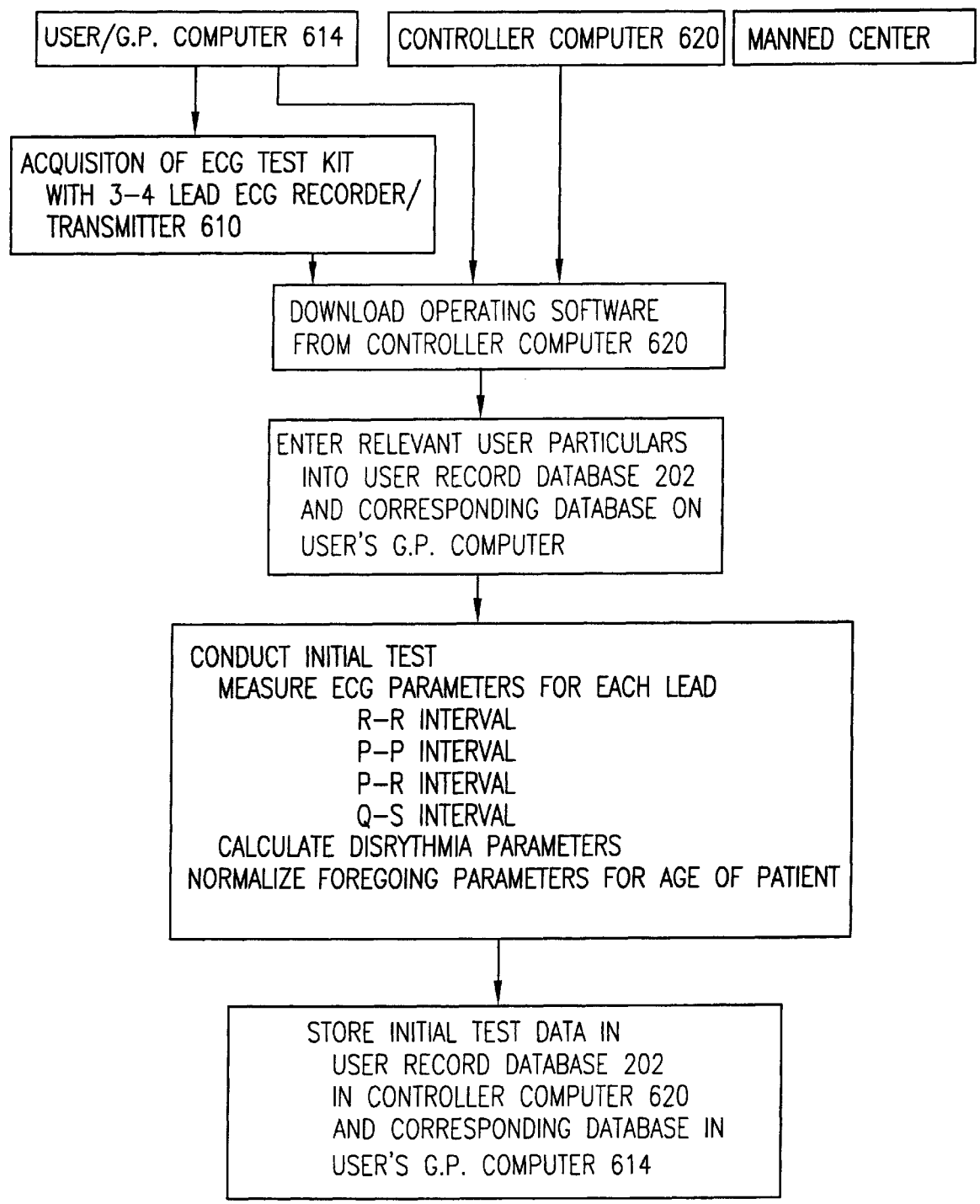
FIG. 7D(1)

FIG. 7D(2)
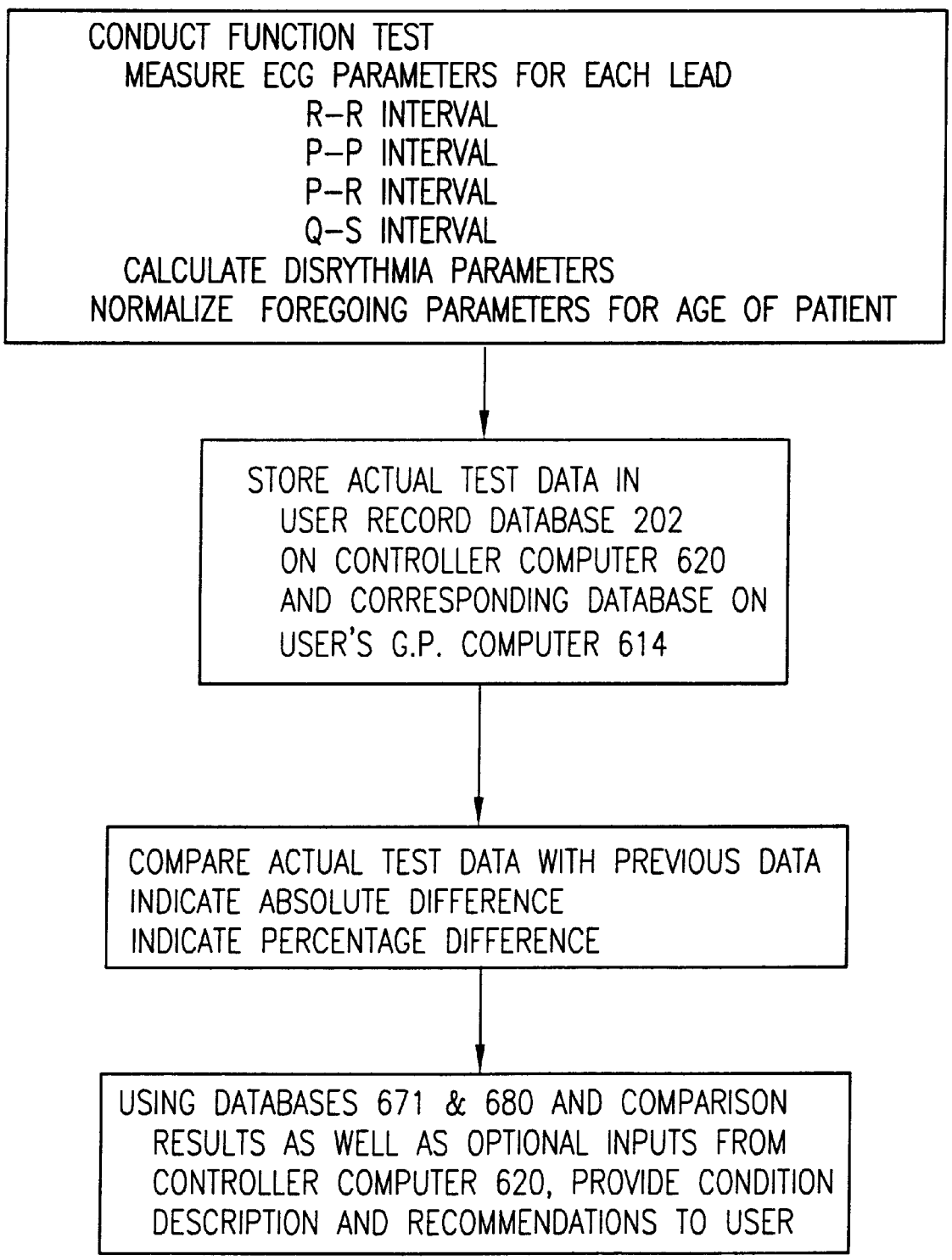

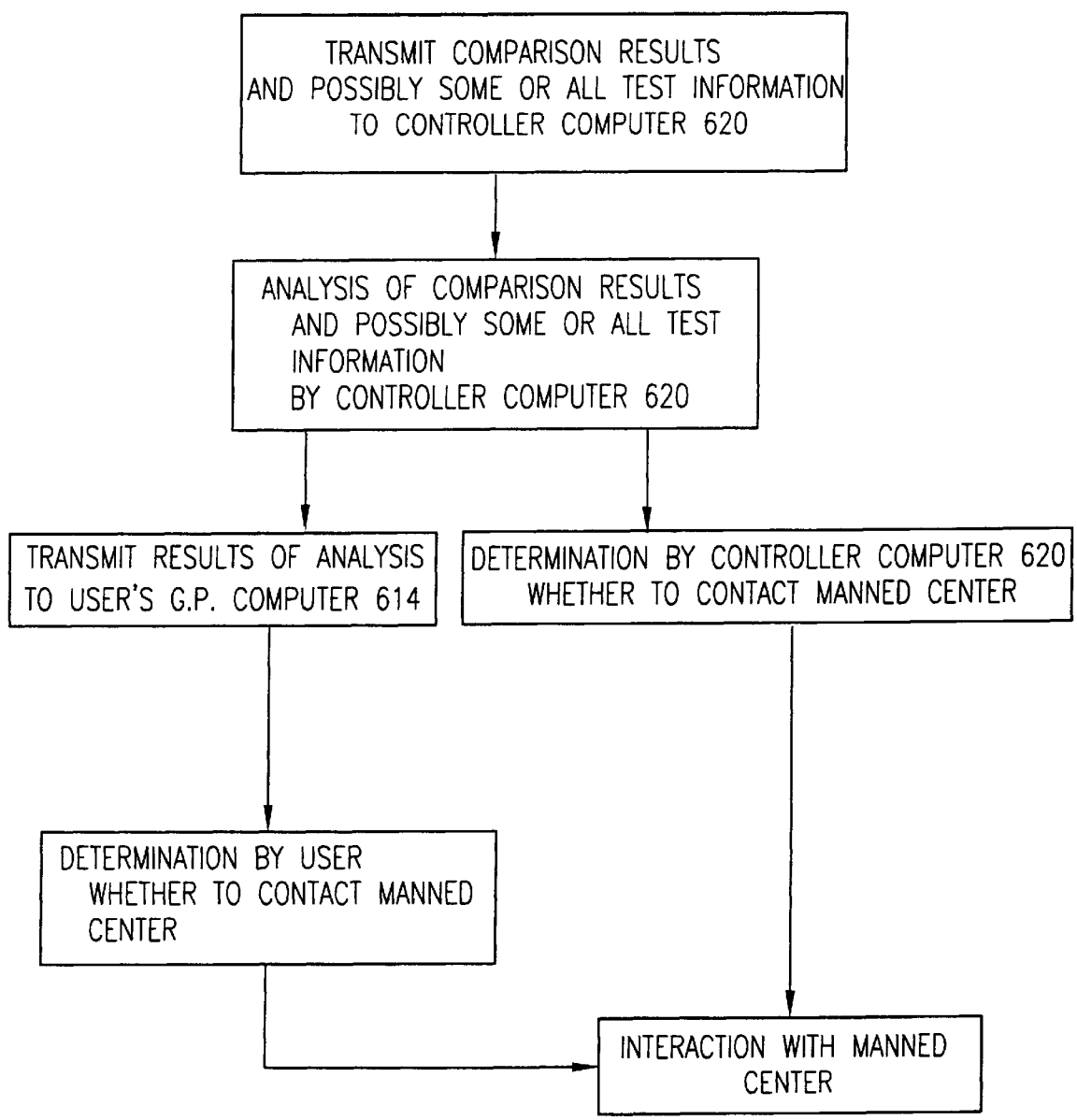
FIG. 7D(3)

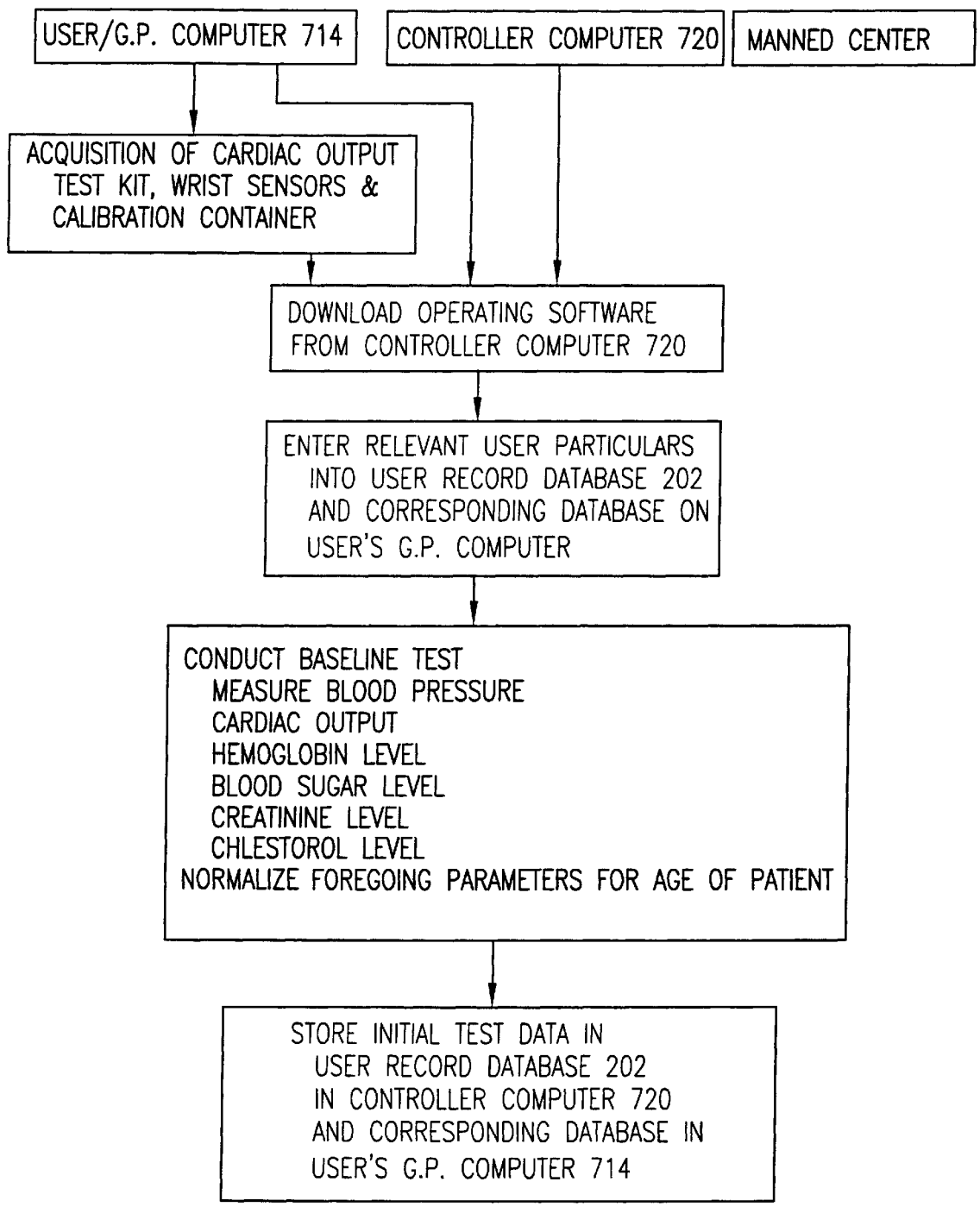

FIG. 7E(2)
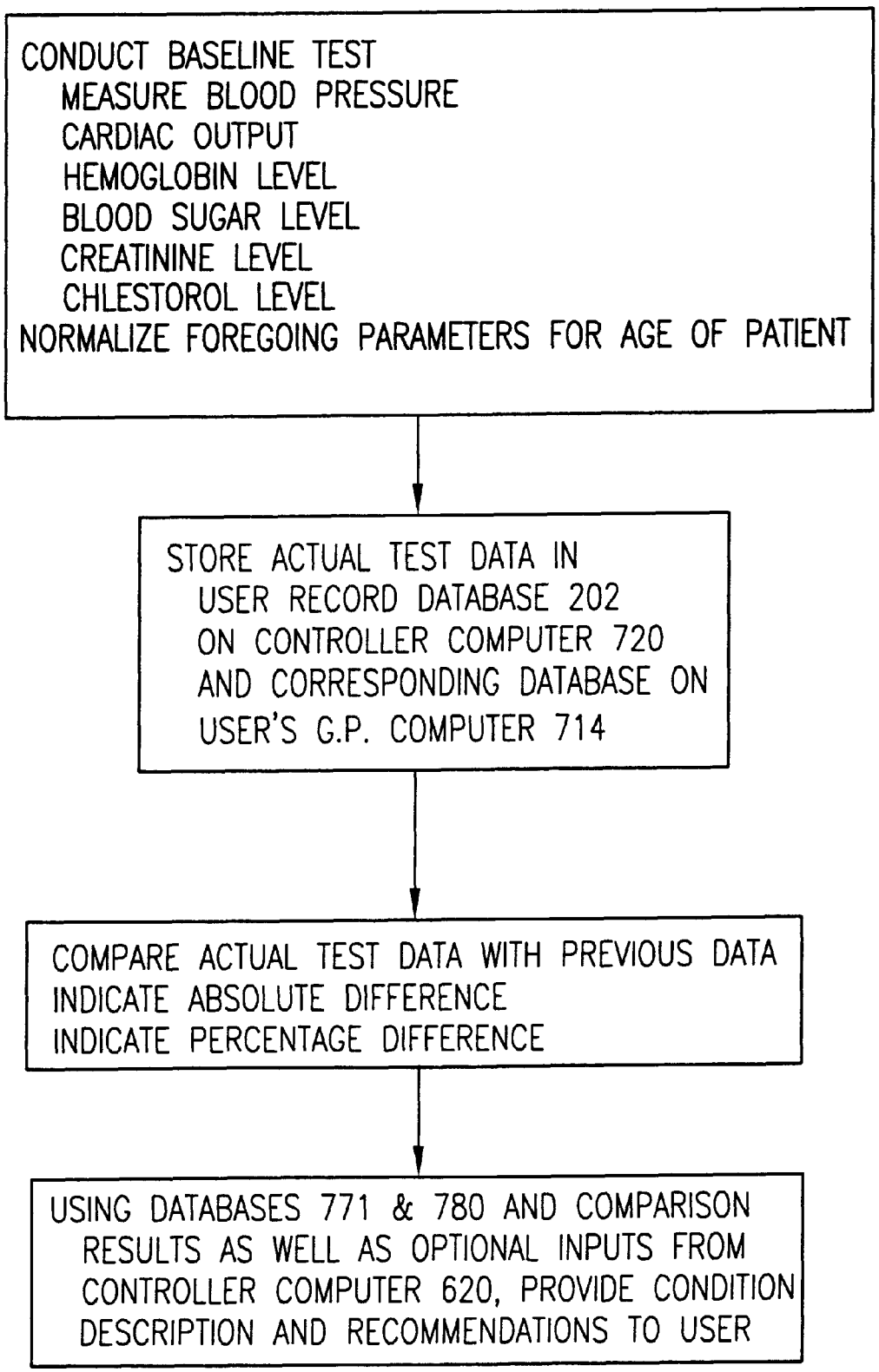

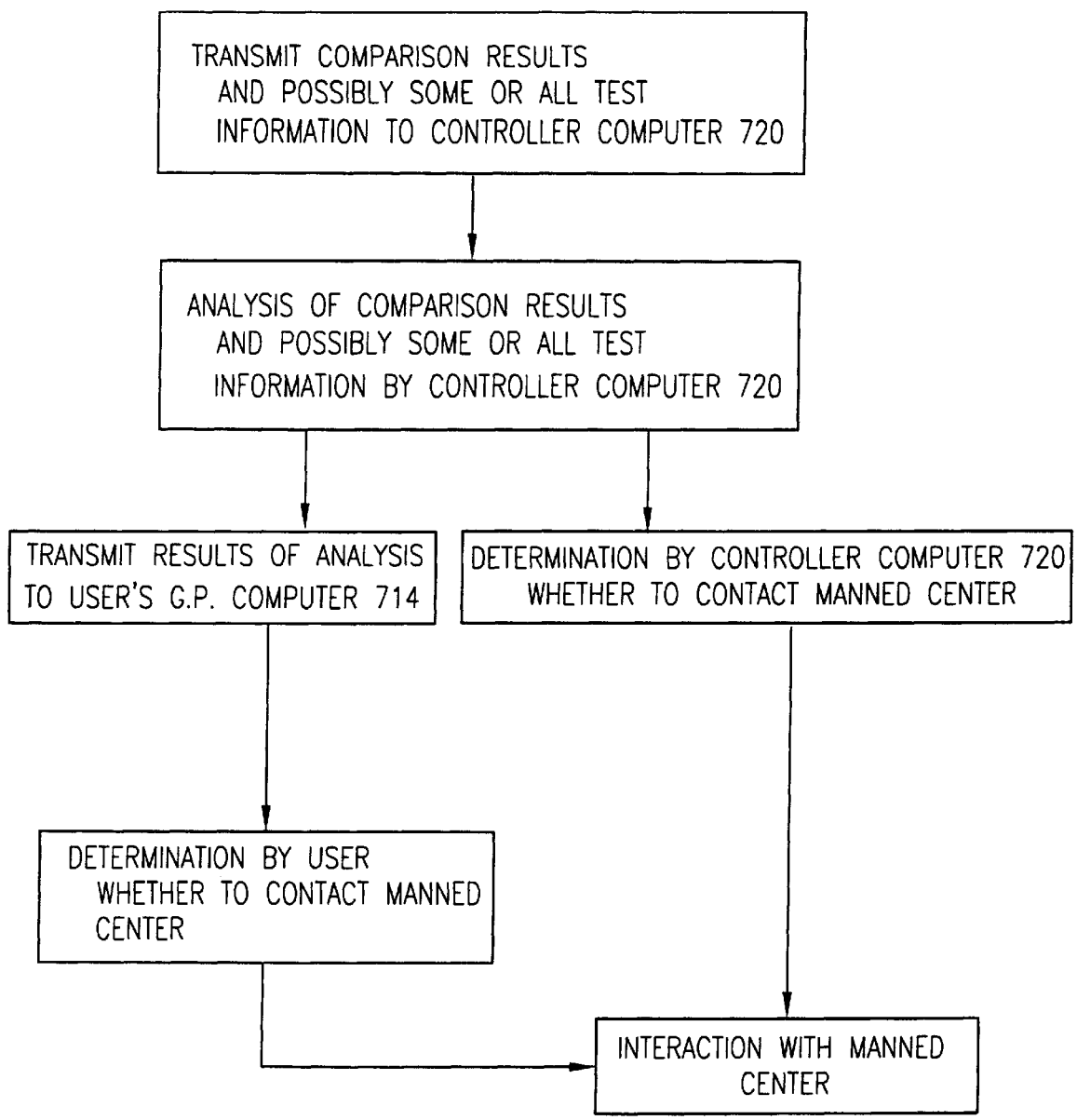
FIG. 7E(3)

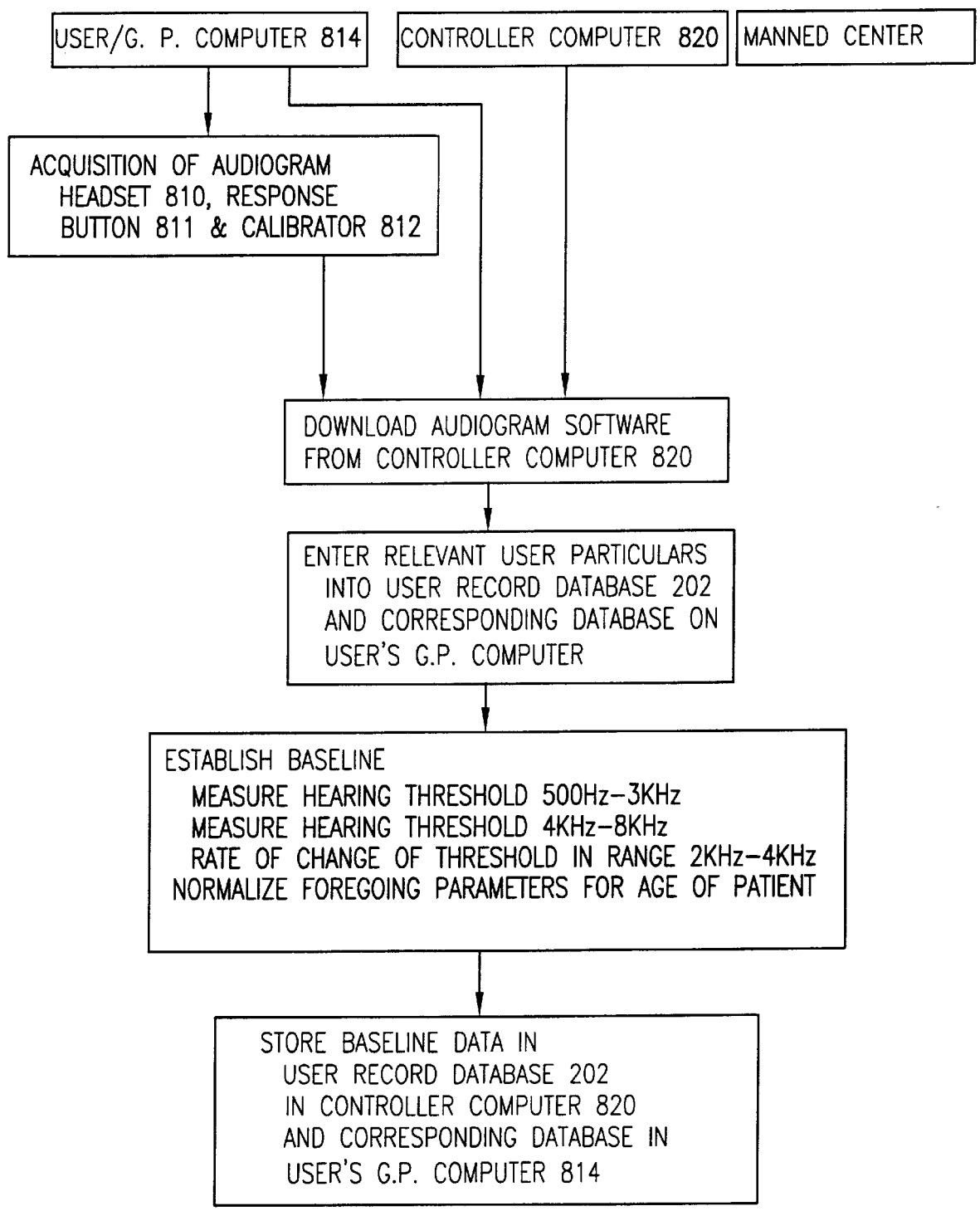

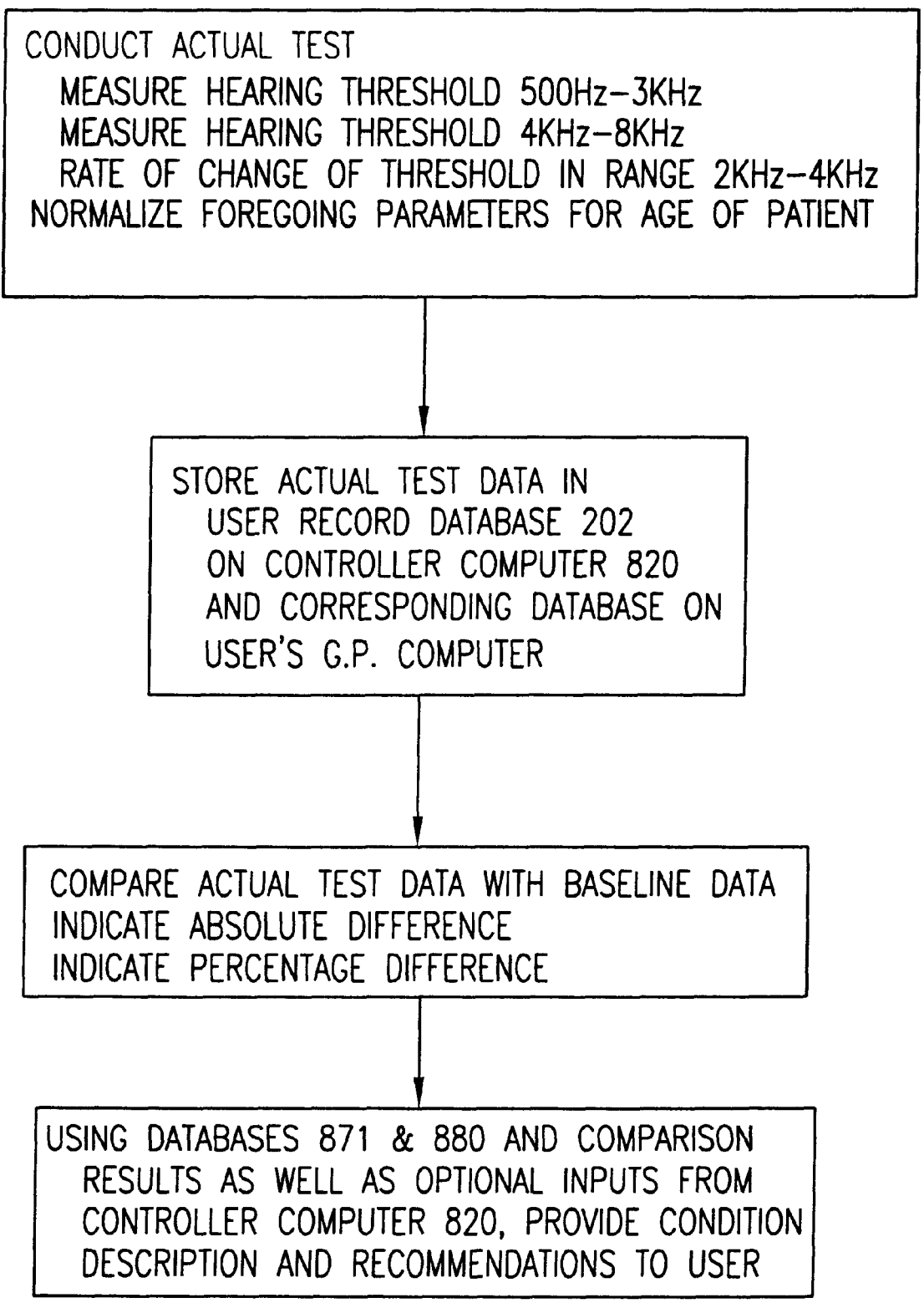
FIG. 7F(2)

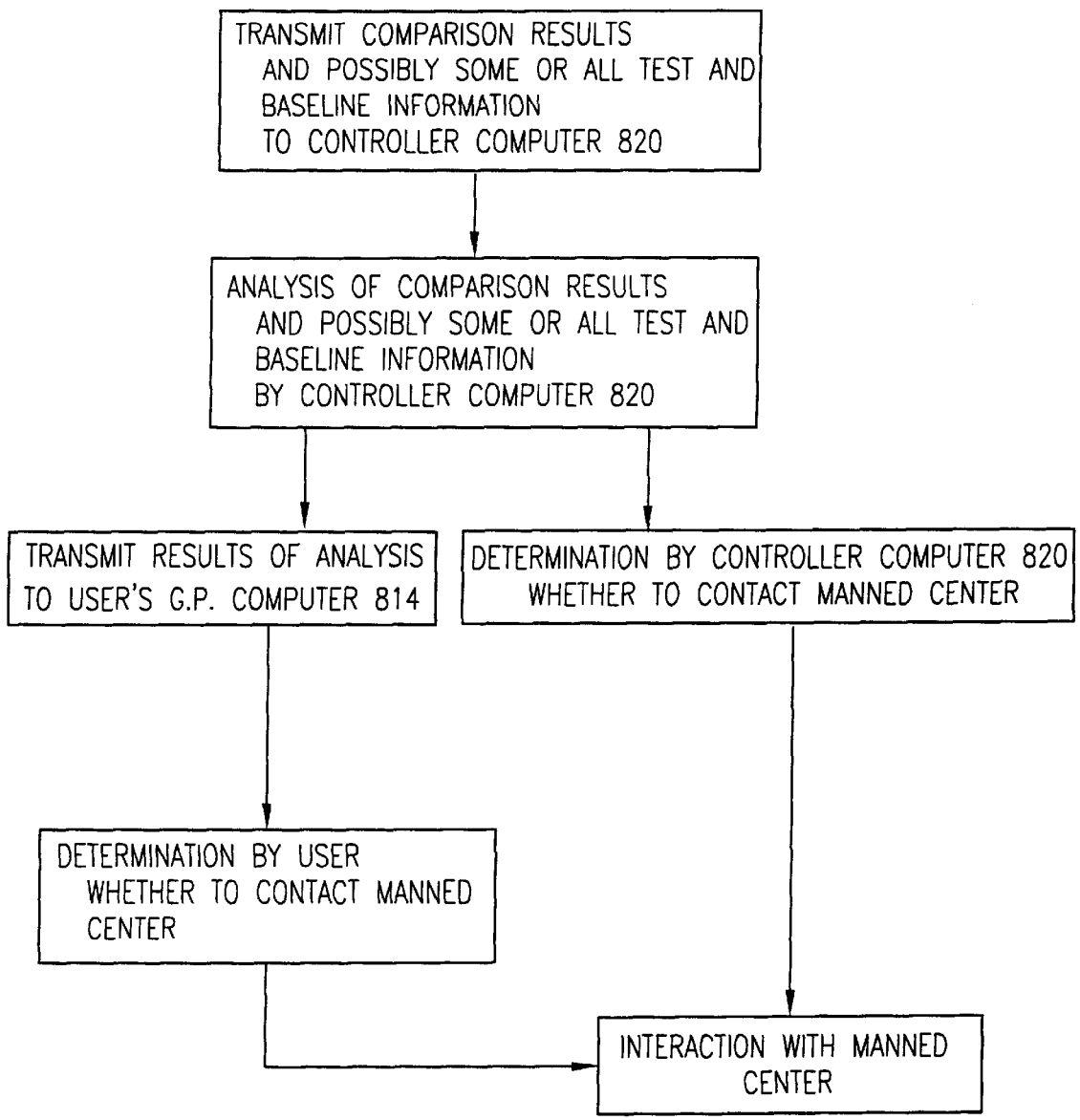
FIG. 7F(3)

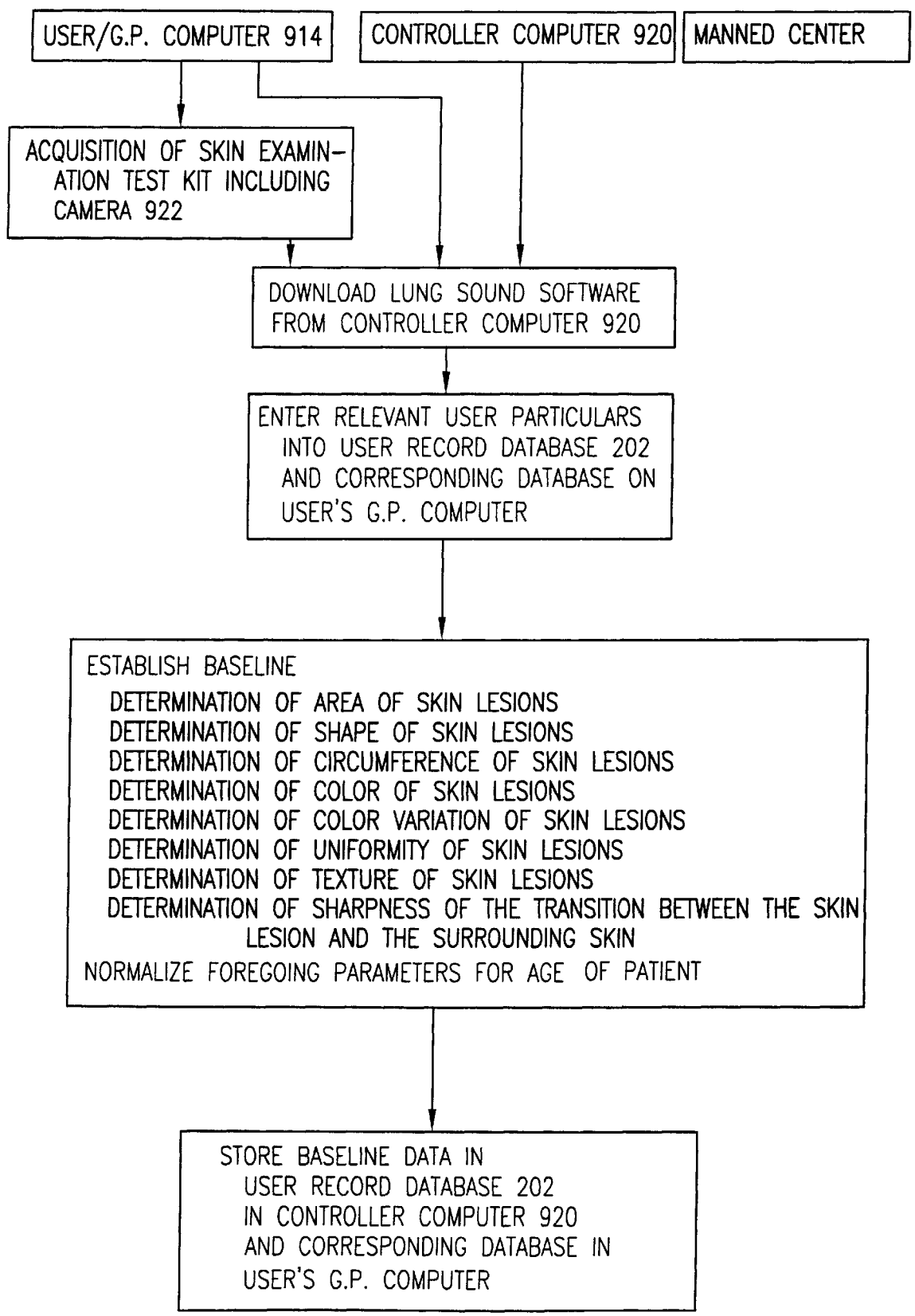
FIG. 7G(1)

FIG. 7G(2)
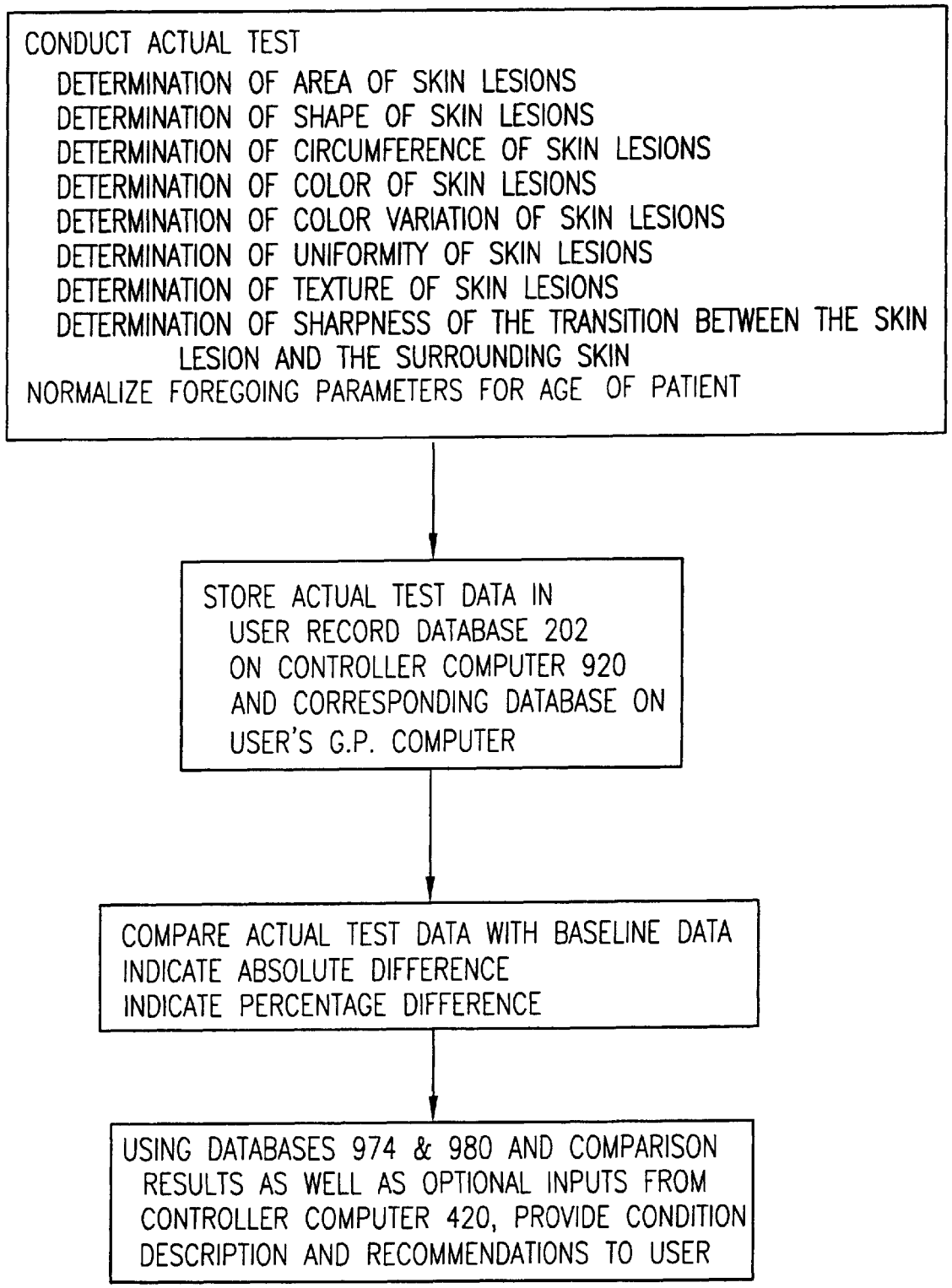

FIG. 7G(3)
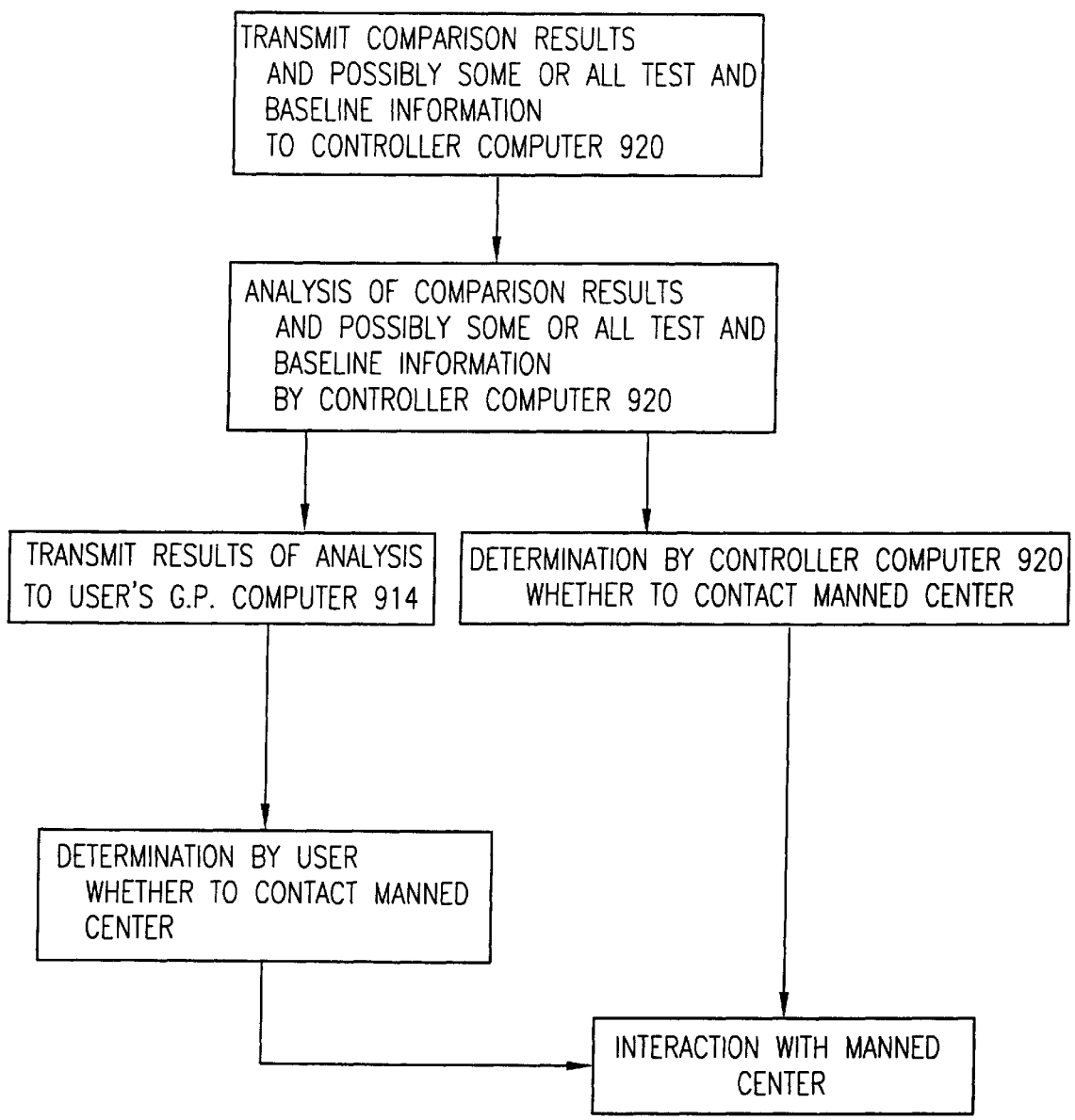

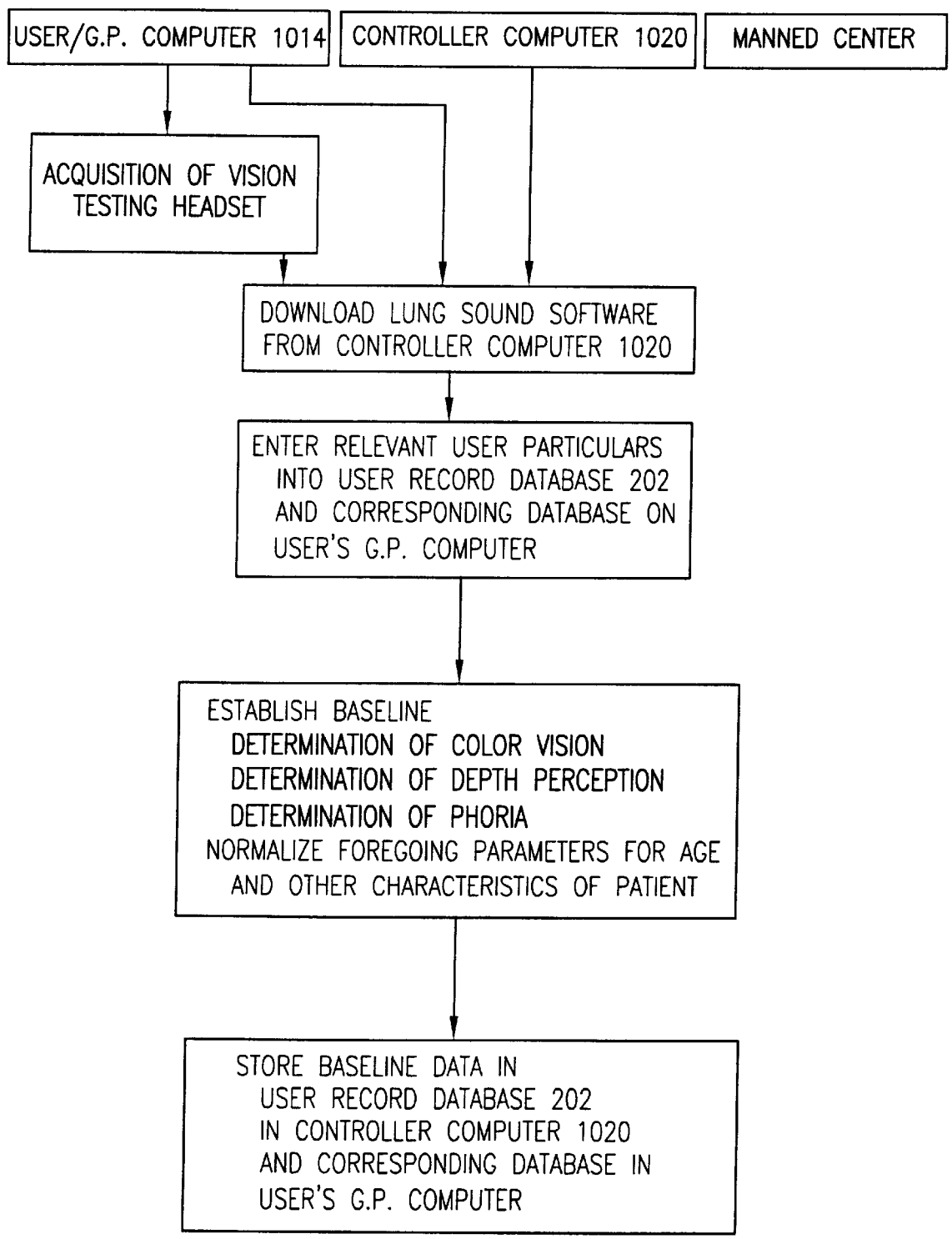
FIG. 7H(1)

FIG. 7H(2)
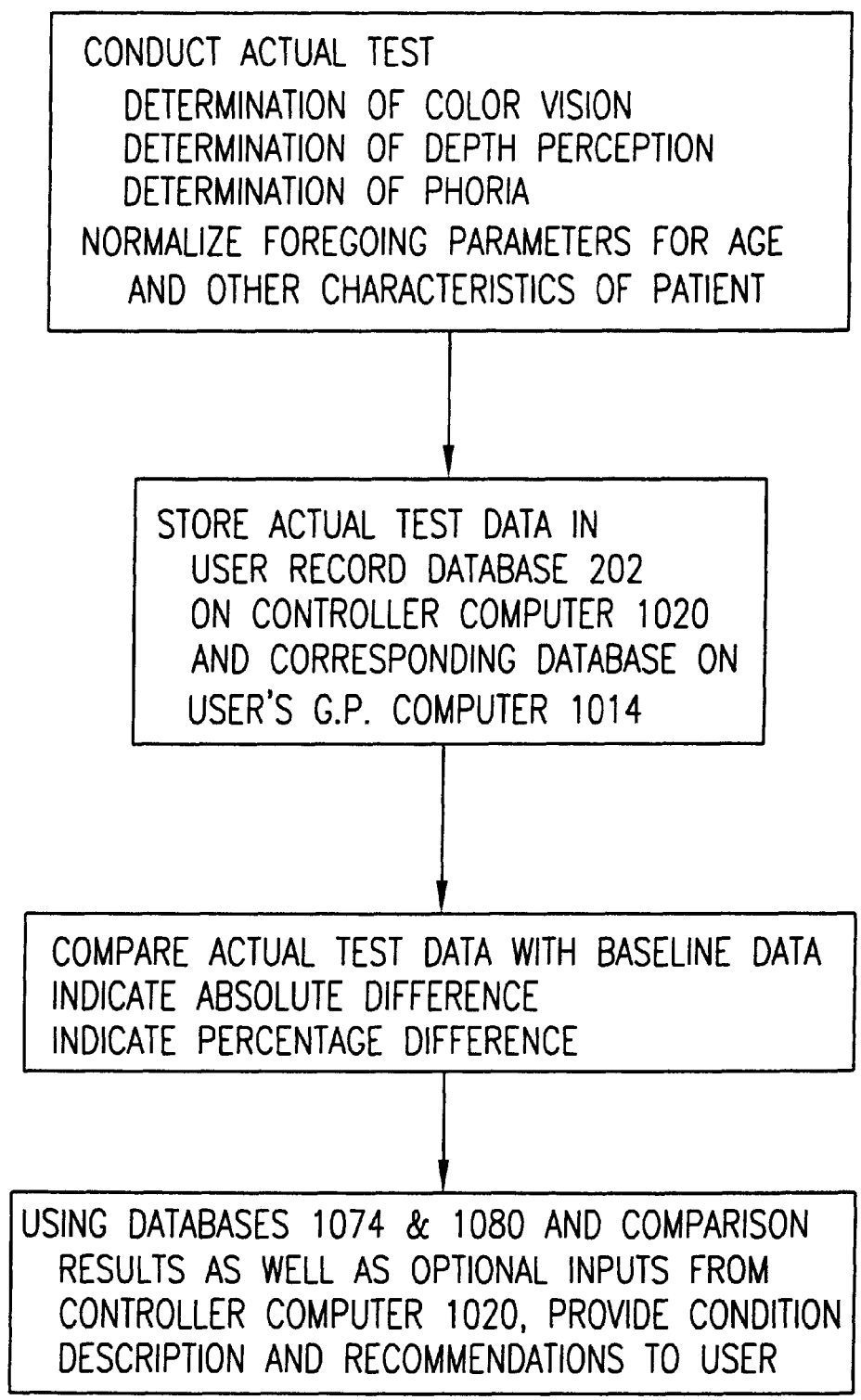

FIG. 7H(3)
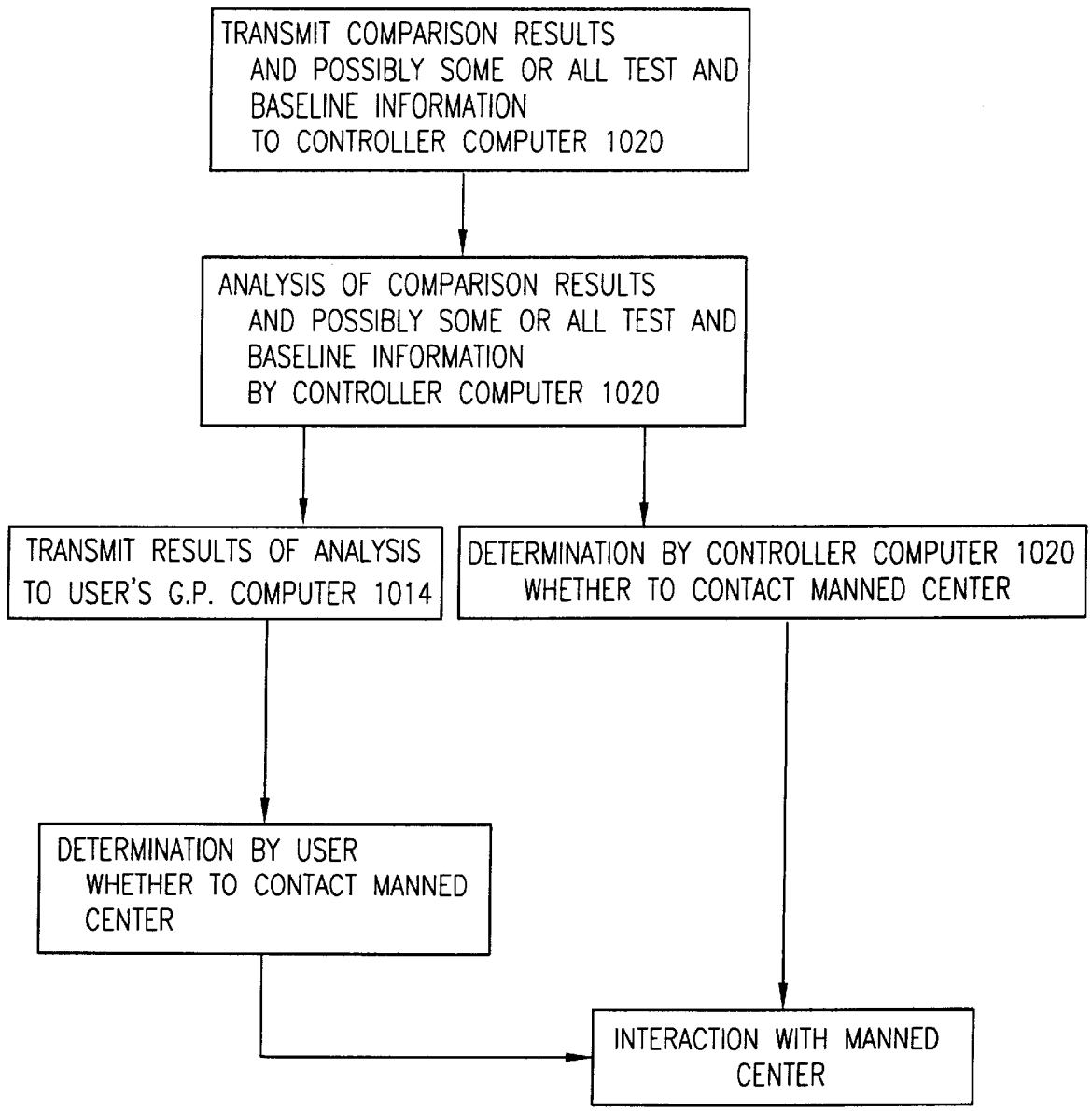

FIG. 8A

| PARAMETER | PREDICTED | BASE LINE DATE: | CURRENT EXAM DATE: | DIFFERENCE \|C-B\| | RATIO D/B |
|---|---|---|---|---|---|
| BREATHING RATE | 18 | 17 | 25 | 8 | 47 |
| INHALATION/ EXHALATION DURATION RATIO | 0.7 | 0.68 | 0.4 | 0.28 | 41 |
| WHEEZING PERCENTAGE DURING INHALATION | 0 | 0 | 5% | 5% | -- |
| WHEEZING PERCENTAGE DURING EXHALATION | 0 | 3% | 25% | 22% | -- |

| A | B | C | D |
|---|---|---|---|
| D/B<15% | D/B 15%-30% | D/B 30%-40% | D/B>40% |
| WEIGHTING=0 | WEIGHTING=1 | WEIGHTING=2 | WEIGHTING=4 |

TOTAL=9

HIGHLY SIGNIFICANT CHANGE IN LUNG SOUND/OBTAIN EMERGENCY TREATMENT IMMEDIATELY

DATE: 02/08/99 AT 18:27
AGE: 37 YEARS HEIGHT: 172 CM
SEX: MALE WEIGHT: 67 KG

| PARAMETER | PREDICTED | BASELINE | CURRENT | C/B% |
|---|---|---|---|---|
| FVC L/SEC | 4.60 | 4.43 | 3.50 | 21 |
| FEVI L/SEC | 3.83 | 3.52 | 2.60 | 26 |
| FEF 25%-75% | 4.45 | 3.81 | 2.00 | 48 |
| PF L/SEC | 9.13 | 10.38 | 6.50 | 37 |

| A | B | C | D |
|---|---|---|---|
| 20%>C/B | 20%≤C/B<35% | 35%≤C/B<50% | C/B>50% |
| WEIGHTING=0 | WEIGHTING=2 | WEIGHTING=4 | WEIGHTING=9 |

<u>TOTAL=12</u>

HIGHLY SIGNIFICANT CHANGE IN LUNG FUNCTIONS/OBTAIN
EMERGENCY TREATMENT IMMEDIATELY

FIG. 8C

DATE: 02/08/99 AT 18:27
AGE: 37 YEARS  HEIGHT: 172 CM
SEX: MALE  WEIGHT: 67 KG

| PARAMETER | NORMAL LIMITS | BASELINE | CURRRRENT | DIFFERENCE | D/B% | W.N.L |
|---|---|---|---|---|---|---|
| HEART RATE | 50-85 | 80 | 10100 | 20 | 25 | NO |
| P-R INTERVAL | 0.1-0.2 MSEC | 0.12 | 0.0.16 | 0.04 | 33 | YES |
| Q-S INTERVAL | 0.08-0.12 MSEC | 0.1 | 0.0.1 | 0 | 0 | YES |
| QRS AXIS | 20°-70° | 60° | 8030° | 20° | 25 | NO |
| T AXIS | 30°-90° | 60° | 12120° | 60° | 100 | NO |
| S-T SEGMENT HEIGHT | 2MM | +1.5MM | -1.1.0MM | 1.5MM | -- | NO |

| A | B | C | D |
|---|---|---|---|
| 20%>D/B | 20%<D/B<30% | D/)/B>30% | ANY PARAMETER WHICH EXCEEDS NORMAL LIMITS |
| WEIGHTING=0 | WEIGHTING=2 | WEIGIGHTING=4 | WEIGHTING=6 |

TOTAL=30
HIGHLY SIGNIFICANT CHANGE IN ELECTRO-
CARDIOGRAM/OBTAIN EMERGENCY
TREATMENT IMMEDIATELY

FIG. 8D

DATE: 02/08/99 AT 18:27
AGE: 37 YEARS  HEIGHT: 172 CM
SEX: MALE  WEIGHT: 67 KG

| PARAMETER | NORMAL LIMITS | BASELINE | CURRENT | D/B% AND/OR PMB | W.N.L |
|---|---|---|---|---|---|
| HEART RATE | 50-85 PER MIN. | 80 | 80 | 0 | YES |
| R-R INTERVAL | 300-800MSEC. UP TO 1 PMB PER MIN. | 450MSEC. NO PMB | 450 MSEC. 1 PMB PER MIN. | 0 1 PER MIN. | YES |
| P-P INTERVAL | 300-800MSEC. UP TO 1 PMB PER MIN. | 450 MSEC. 0 | 450MSEC. 1 PMB | 0 1 PER MIN. | YES |
| Q-T INTERVAL | 80-120MSEC. UP TO 1 PMB PER MIN. | 100 MSEC. 0 | 250 MSEC. 1 PER MIN. | 0 1 PER MIN. | YES |

| A | B | C | D |
|---|---|---|---|
| D/B<20% NO PMB | D/B 20%-30% PMB UP TO 1/min | D/B>30% PMB>3/min | ANY PARAMETER WHICH EXCEEDS NORMAL LIMITS |
| WEIGHTING=0 | WEIGHTING=4 | WEIGHTING=9 | WEIGHTING=4 |

TOTAL=17

SIGNIFICANT CHANGE IN ELECTRO-
CARDIOGRAM/ELECTROCARDIOGRAM DATA
BEING TRANSFERRED TO CONTROLLER
AND/OR MANNED CENTER FOR EVALUATION
OBTAIN EMERGENCY TREATMENT IMMEDIATELY

DATE: 02/08/99 AT 18:27
AGE: 37 YEARS  HEIGHT: 172 CM
SEX: MALE  WEIGHT: 67 KG

| PARAMETER | NORMAL LIMITS | BASELINE | CURRENT | D/B% | W.N.L |
|---|---|---|---|---|---|
| HEART RATE | 50-85 | 80 | 80 | 0 | YES |
| BLOOD PRESSURE | 100/60 TO 140/60 mmHg | 120/80 | 120/80 | 0 | YES |
| CARDIAC OUTPUT | 4.5-6 LIT./MIN. | 4.5 | 4.05 | 10 | NO |

| A | B | C | ANY PARAMETER WHICH EXCEEDS NORMAL LIMITS |
|---|---|---|---|
| WEIGHTING=0 | WEIGHTING=2 | WEIGHTING=4 | WEIGHTING=8 |

TOTAL= 8

SLIGHT CHANGE IN CARDIAC PARAMETERS/CONTACT PHYSICIAN/REPEAT TEST

DATE: 02/08/99 AT 18:27
AGE: 37 YEARS
SEX: MALE

| PARAMETER | NORMAL LIMITS | BASELINE | CURRENT | D/B% | W.N.L |
|---|---|---|---|---|---|
| AVERAGE 500-3000Hz | 0-20dB | 15dB | 20dB | 33 | YES |
| 4000-8000Hz | 0-25dB | 20dB | 40dB | 100 | NO |
| SLOPE | UP TO 25° | 25° | 50° | 100 | NO |

| A | B | C |
|---|---|---|
| D/B<25% | D/B>25% | PARAMETER EXCEEDS NORMAL LIMITS |
| WEIGHTING=0 | WEIGHTING=2 | WEIGHTING=6 |

TOTAL= 24

SIGNIFICANT CHANGE IN AUDIOGRAM/CONSULT PHYSICIAN

DATE: 02/08/99 AT 18:27
AGE: 37 YEARS
SEX: MALE

| PARAMETER | NORMAL LIMITS | BASELINE | CURRENT | D/B% | PATHOLOGICAL PATTERN |
|---|---|---|---|---|---|
| AREA | - | 1.2 CM² | 1.6 CM² | 33 | - |
| CIRCUM-FERENCE | - | 2.5 CM | 3.75 CM | 50 | - |
| UNIFORMITY | - | UNIFORM | PATCHY | - | NO |
| SHARPNESS OF BORDER | SHARP | SHARP | 20% OF BORDER-NOT SHARP | - | NO |

| A | B | C |
|---|---|---|
| D/B<20% | D/B>20% | PATHOLOGICAL PATTERN |
| WEIGHTING=0 | WEIGHTING=4 | WEIGHTING=6 |

TOTAL=20
SIGNIFICANT CHANGE IN SKIN LESIONS/CONSULT PHYSICIAN

FIG. 8H

DATE: 02/08/99 AT 18:27
AGE: 37 YEARS
SEX: MALE

| PARAMETER | NORMAL LIMITS | BASELINE | CURRENT | C/B | W.N.L |
|---|---|---|---|---|---|
| VISUAL ACUITY 40 CMS | 40 CM / 40 CM | 40 CM / 40 CM | 40 CM / 40 CM | — | YES |
| VISUAL ACUITY 600 CMS | 6M / 6M | 6 / 18 | 6 / 18 | — | NO |
| DEPTH PERCEPTION | 100%–70% | 80% | 60% | 20% | YES |

| A | B | C |
|---|---|---|
| C/B<30% | C/B>30% | PARAMETERS WHICH EXCEED NORMAL LIMITS |
| WEIGHTING=0 | WEIGHTING=8 | WEIGHTING=4 |

TOTAL=4

CHANGE IN VISION FROM PREVIOUS EXAMINATION OR VISION OUTSIDE NORMAL LIMITS/CONTACT VISION PROFESSIONAL/ REPEAT TEST

US 6,648,820 B1

MEDICAL CONDITION SENSING SYSTEM

FIELD OF THE INVENTION

The present invention to medical condition sensing and evaluation and more particularly to medical condition sensing and evaluation over computer networks.

BACKGROUND OF THE INVENTION

There exist in the patent literature various proposals for medical sensing and evaluation over computer networks. The following U.S. Patents are believed to represent the state of the art: U.S. Pat. Nos. 5,907,291; 5,906,208; 5,902,234; 5,897,493; 5,895,354; 5,892,570; 5,879,292; 5,873,369; 5,868,669; 5,868,135; 5,868,134; 5,865,733; 5,855,550; 5,848,975; 5,842,977; 5,842,975; 5,840,018; 5,827,180; 5,811,681; 5,79.1,908; 5,791,342; 5,769,074; 5,758,652; 5,677,979; 5,619,991.

SUMMARY OF THE INVENTION

The present invention seeks to provide a highly effective computer network based system for medical sensing and evaluation as well as interface elements useful in the system.

There is thus provided in accordance with a preferred embodiment of the present invention a medical condition sensing system including a multiplicity of general purpose computers disposed in user locations and being connected via a computer network to at least one controller computer remote from at least one of the user locations, personal parameter measuring software resident on at least one of the multiplicity of general purpose computers and the at least one controller computer for measuring at least one personal parameter of at least one user, personal parameter reference generating software resident on at least one of said multiplicity of general purpose computers and said at least one controller computer for establishing a reference for the at least one personal parameter, and personal parameter comparison software resident on at least one of the multiplicity of general purpose computers and the at least one controller computer for comparing at least one currently measured personal parameter with a corresponding reference and providing a comparison output.

Further in accordance with a preferred embodiment of the present invention the medical condition sensing system also includes alert indication software resident on at least one of the multiplicity of general purpose computers and the at least one controller computer for providing a generally real time alert indication to the user based at least partially on the comparison output. Preferably, the alert indication software is resident on the multiplicity of general purpose computers.

Still further in accordance with a preferred embodiment of the present invention the reference may be a personal parameter baseline constructed from pre-real time measurements of the personal parameter, a calibration reference employing a measurement of a personal parameter based on a calibration input, a calibration reference based on a calibration input, a calibration reference based on a calibration input supplied from another computer via the computer network, and/or a calibration reference employing a measurement of a personal parameter based on a calibration input supplied from another computer via the computer network. Preferably, the personal parameter comparison software is operative to compare at least one currently measured personal parameter with the calibration reference.

Additionally in accordance with a preferred embodiment of the present invention, the medical condition sensing system also includes notification software resident on at least one of the multiplicity of general purpose computers and the at least one controller for transmitting a notification from one of the at multiplicity of general purpose computers to at least one other computer based on the comparison output.

Further in accordance with a preferred embodiment of the present invention, the personal parameter includes a heart function parameter, a blood parameter, a electrocardiogram parameter, a hearing function parameter, a skin appearance parameter, a tissue appearance parameter, an optically sensible parameter, an electrically sensible parameter, a thermally sensible parameter, an audibly sensible parameter, and/or a chemically sensible parameter.

Still further in accordance with a preferred embodiment of the present invention the personal parameter comparison software is operative to compare optical images of at least one body region.

Additionally in accordance with a preferred embodiment of the present invention the personal parameter measuring software is operative to measure at least one personal parameter of at least one user in response to an input supplied to the user. The personal parameter measuring software also includes feedback software and feedback circuitry for calibrating the input supplied to the user. Preferably, the feedback software is operative to communicate between a general purpose computer and the controller computer over the computer network.

Additionally or alternatively the feedback circuitry is operative to communicate between a general purpose computer and the controller computer over the computer network.

Still further in accordance with a preferred embodiment of the present invention the personal parameter measuring software also includes feedback software for calibrating a measured personal parameter of a user.

Furthermore in accordance with a preferred embodiment of the present invention the medical condition sensing system also includes feedback circuitry for calibrating a measured personal parameter of a user. Additionally or alternatively the feedback software is operative to communicate between a general purpose computer and the controller computer over the computer network.

Moreover the feedback circuitry is operative to communicate between a general purpose computer and the controller computer over the computer network.

Further in accordance with a preferred embodiment of the present invention the medical condition sensing system also includes software utilizing the output of at least one of the personal parameter measuring software, the personal parameter reference generating software, and the personal parameter comparison software for providing at least one of recommendations and indications to a user.

Still further in accordance with a preferred embodiment of the present invention the medical condition sensing system also includes a manned center accessible at least via the computer network for receiving at least some of the output of at least one of the personal parameter measuring software, the personal parameter reference generating software the personal parameter comparison software and at least one of recommendations and indications to a user and providing health professional interaction with the user.

Preferably, the manned center is accessible at least via the computer network for receiving at least some of the output of at least one of the personal parameter measuring software, the personal parameter reference generating software the personal parameter comparison software and at least one of recommendations and indications to a user and providing health professional interaction with the user.

Additionally or preferably at least one of the recommendations and indications as well as the criteria therefor is determinable by a user's health professional by transmitting instructions to at least one of the controller computer and the general purpose computer via the computer network. Furthermore, at least one of the recommendations and indications as well as the criteria therefor is determinable by a user's health professional by transmitting instructions to at least one of the controller computer and the general purpose computer via the computer network.

Still further in accordance with a preferred embodiment of the present invention the manned center employs a personal physician of the user and communicates with him via through at least one of telephone and data links via at least one of wired and wireless communication media.

Moreover in accordance with a preferred embodiment of the present invention, the medical condition sensing system also includes personal parameter analysis software resident on at least one of the multiplicity of general purpose computers and the at least one controller computer for analyzing the at least one personal parameter of at least one user. The analysis of at least one personal parameter of at least one user takes place partially at a general purpose computer at at least one user location and partially at the at least one controller computer.

Additionally or alternatively the analysis of at least one personal parameter of at least one user at a general purpose computer at at least one user location provides an analysis output which determines whether further analysis of the at least one personal parameter is carried out at the at least one controller computer.

Still further in accordance with a preferred embodiment of the present invention, the at least one of the general purpose computer and the at least one controller computer serves as a backup for another one of the general purpose computer and the at least one controller computer.

There is also provided in accordance with yet another preferred embodiment of the present invention apparatus for collecting medical data including a user station connected to at least one computer remote from the user station via a computer network, a user interface connected to the user station, and a calibration system operative to calibrate the user interface which employs communication via the at least one computer network.

Further in accordance with a preferred embodiment of the present invention the said calibration system operates automatically without operator intervention.

Still further in accordance with a preferred embodiment of the present invention the apparatus for collecting medical data also includes personal parameter analysis software resident on at least one of the user station and the at least one computer for analyzing the at least one personal parameter of at least one user.

Preferably, analysis of at least one personal parameter of at least one user takes place partially at said user station and partially at the at least one computer.

The analysis of at least one personal parameter of at least one user provides an analysis output which determines whether further analysis of the at least one personal parameter is carried out at the at least one computer.

Additionally in accordance with a preferred embodiment of the present invention, the at least one of the user stations and the at least one computer serves as a backup for another one of the user stations and the at least one computer.

There is also provided in accordance with yet another preferred embodiment of the present invention apparatus for collecting medical data including a general purpose computer, a user interface connected to said computer, a recording and storage facility for recording and storing at least one baseline result received by the user station using the user interface from at least a first test taken at least a first time, and a comparison facility for receiving at least one subsequent result received by the user station using the user interface from at least a second test, similar to the first test, taken at at least a second time, later than the first time, comparing the at least second test with the at least first test, applying a threshold to a comparison result and providing an indication in response to exceedance of the threshold.

There is further provided in accordance with another preferred embodiment of the present invention a user interface assembly suitable for use in apparatus for collecting medical data including a user station connected to at least one computer remote from said user station via a computer network, the user interface assembly includes a user interface coupled to said user station for use in collecting medical data from a subject, software usable by the user station to control the operation of the user interface and to communicate via the computer network with the at least one computer remote from the user station.

Further in accordance with a preferred embodiment of the present invention the software is useful at least to communicate data required for calibration of at least one of the user interface and the user station.

There is provided in accordance with yet another preferred embodiment of the present invention a user interface assembly suitable for use in apparatus for collecting medical data including a general purpose computer, the user interface assembly includes a user interface coupled to the user station for use in collecting medical data from a subject, software usable by the general purpose computer and providing at least the following functionality a recording and storage functionality for recording and storing at least one baseline result received by the general purpose computer via the user interface from at least a first test taken at at least a first time, and a comparison facility for receiving at least one subsequent result received by the general purpose computer using the user interface from at least a second test, similar to the first test, taken at at least a second time, later than the first time, comparing the at least second test with the at least first test, applying a threshold to a comparison result and providing an indication in response to exceedance of the threshold.

There is further provided in accordance with yet another preferred embodiment of the present invention a medical condition sensing system including a multiplicity of general purpose computers disposed in user locations and being connected via a computer network to at least one controller computer remote from at least one of the user locations, personal parameter measuring software resident on at least one of the multiplicity of general purpose computers and the at least one controller computer for measuring at least one personal parameter of at least one user, personal parameter analysis software resident on at least one of the multiplicity of general purpose computers and the at least one controller computer for analyzing the at least one personal parameter of at least one user.

Further in accordance with a preferred embodiment of the present invention the analysis of at least one personal parameter of at least one user takes place partially at a general purpose computer at at least one user location and partially at the at least one controller computer.

Still further in accordance with a preferred embodiment of the present invention the analysis of at least one personal parameter of at least one user at a general purpose computer at at least one user location provides an analysis output which determines whether further analysis of the at least one personal parameter is carried out at the at least one controller computer.

Additionally in accordance with a preferred embodiment of the present invention at least one of the general purpose computer and the at least one controller computer serves as a backup for another one of the general purpose computer and the at least one controller computer.

There is also provided in accordance with a preferred embodiment of the present invention a medical condition sensing method including:

connecting a multiplicity of general purpose computers disposed in user locations via a computer network to at least one controller computer remote from at least one of the user locations;

employing personal parameter measuring software resident on at least one of the multiplicity of general purpose computers and the at least one controller computer for measuring at least one personal parameter of at least one user;

employing personal parameter reference generating software resident on at least one of the multiplicity of general purpose computers and the at least one controller computer for establishing a reference for the at least one personal parameter; and employing personal parameter comparison software resident on at least one of the multiplicity of general purpose computers and the at least one controller computer for comparing at least one currently measured personal parameter with a corresponding reference and providing a comparison output.

Preferably, the method also includes utilizing alert indication software resident on at least one of the multiplicity of general purpose computers and the at least one controller computer for providing a generally real time alert indication to the user based at least partially on the comparison output.

In accordance with a preferred embodiment of the present invention, the alert indication software is resident on the multiplicity of general purpose computers.

Preferably, the reference is a personal parameter baseline constructed from pre-real time measurements of the personal parameter.

Alternatively, the reference is a calibration reference employing a measurement of a personal parameter based on a calibration input.

In accordance with a preferred embodiment of the present invention, the reference is a calibration reference based on a calibration input.

In accordance with a preferred embodiment of the present invention the reference is a calibration reference based on a calibration input supplied from another computer via the computer network.

Preferably, the reference is a calibration reference employing a measurement of a personal parameter based on a calibration input supplied from another computer via the computer network.

In accordance with a preferred embodiment of the present invention the personal parameter comparison software is operative to compare at least one currently measured personal parameter with the calibration reference.

Preferably, the method includes comprising employing notification software resident on at least one of the multiplicity of general purpose computers and the at least one controller for transmitting a notification from one of the at multiplicity of general purpose computers to at least one other computer based on the comparison output.

In accordance with a preferred embodiment of the present invention the personal parameter comprises a heart function parameter.

In accordance with another preferred embodiment of the present invention the personal parameter comprises a blood parameter.

In accordance with yet another preferred embodiment of the present invention the personal parameter comprises a electrocardiogram parameter.

In accordance with still another preferred embodiment of the present invention the personal parameter comprises a hearing function parameter.

Alternatively the personal parameter comprises a skin appearance parameter, a tissue appearance parameter, an optically sensible parameter, an electrically sensible parameter, an thermally sensible parameter, an audibly sensible parameter, a chemically sensible parameter, Preferably, the personal parameter comparison software is operative to compare optical images of at least one body region.

In accordance with another preferred embodiment of the present invention the personal parameter measuring software is operative to measure at least one personal parameter of at least one user in response to an input supplied to the user.

Preferably, the personal parameter measuring software includes feedback software for calibrating the input supplied to the user.

In accordance with another preferred embodiment of the present invention the method includes employing feedback circuitry for calibrating the input supplied to the user.

Preferably, the feedback software is operative to communicate between a general purpose computer and the controller computer over the computer network.

Alternatively, the feedback circuitry is operative to communicate between a general purpose computer and the controller computer over the computer network.

Preferably, the personal parameter measuring software includes feedback software for calibrating a measured personal parameter of a user.

In accordance with another preferred embodiment of the present invention calibrating a measured personal parameter of a user.

Preferably, the method employs feedback software which is operative to communicate between a general purpose computer and the controller computer over the computer network.

In accordance with another preferred embodiment of the present invention, the feedback circuitry is operative to communicate between a general purpose computer and the controller computer over the computer network.

Preferably, the method employing software utilizing the output of at least one of the personal parameter measuring software, the personal parameter reference generating software, and the personal parameter comparison software for providing at least one of recommendations and indications to a user.

In accordance with another preferred embodiment of the present invention the method includes accessing a manned center at least via the computer network for receiving at least some of the output of at least one of the personal parameter measuring software, the personal parameter reference generating software, the personal parameter comparison software and at least one of recommendations and indications to a user and providing health professional interaction with the user.

Preferably, at least one of the recommendations and indications as well as the criteria therefor is determinable by a users health professional by transmitting instructions to at least one of the controller computer and the general purpose computer via the computer network.

In accordance with another preferred embodiment of the present invention, the manned center employs a personal physician of the user and communicates with him via through at least one of telephone and data links via at least one of wired and wireless communication media.

Preferably, the method employs personal parameter analysis software resident on at least one of the multiplicity of general purpose computers and the at least one controller computer for analyzing the at least one personal parameter of at least one user.

In accordance with another preferred embodiment of the present invention analysis of at least one personal parameter of at least one user takes place partially at a general purpose computer at at least one user location and partially at the at least one controller computer.

Preferably, analysis of at least one personal parameter of at least one user at a general purpose computer at at least one user location provides an analysis output which determines whether further analysis of the at least one personal parameter is carried out at the at least one controller computer.

In accordance with another preferred embodiment of the present invention at least one of the general purpose computer and the at least one controller computer serves as a backup for another one of the general purpose computer and the at least one controller computer.

There is additionally provided in accordance with a preferred embodiment of the present invention a method for collecting medical data including:
    connecting a user station to at least one computer remote from the user station via a computer network;
    connecting a user interface to the user station; and
    calibrating the user interface by employing communication via the at least one computer network.

Preferably, the calibrating step operates automatically without operator intervention.

The method preferably employs personal parameter analysis software resident on at least one of the user station and the at least one computer for analyzing the at least one personal parameter of at least one user.

In accordance with another preferred embodiment of the present invention, analysis of at least one personal parameter of at least one user takes place partially at the user station and partially at the at least one computer.

Preferably, analysis of at least one personal parameter of at least one user provides an analysis output which determines whether further analysis of the at least one personal parameter is carried out at the at least one computer.

In accordance with another preferred embodiment of the present invention at least one of the user station and the at least one computer serves as a backup for another one of the user station and the at least one computer.

There is additionally provided in accordance with a preferred embodiment of the present invention a method for collecting medical data including:
    providing a general purpose computer;
    connecting a user interface to the computer;
    recording and storing at least one baseline result received by the user station using the user interface from at least a first test taken at least a first time; and
    receiving at least one subsequent result received by the user station using the user interface from at least a second test, similar to the first test, taken at at least a second time, later than the first time, comparing the at least second test with the at least first test, applying a threshold to a comparison result and providing an indication in response to exceedance of the threshold.

There is also provided in accordance with a preferred embodiment of the present invention a user interface method suitable for use in apparatus for collecting medical data including a user station connected to at least one computer remote from the user station via a computer network, the user interface method comprising:
    coupling a user interface to the user station for use in collecting medical data from a subject;
    employing software to control the operation of the user interface and to communicate via the computer network with the at least one computer remote from the user station.

Preferably, the software is useful at least to communicate data required for calibration of at least one of the user interface and the user station.

There is additionally provided in accordance with a preferred embodiment of the present invention a user interface method suitable for use in apparatus for collecting medical data including a general purpose computer, the user interface method comprising:
    coupling a user interface to the user station for collecting medical data from a subject;
    employing software providing at least the following functionality:
        recording and storing at least one baseline result received by the general purpose computer via the user interface from at least a first test taken at at least a first time; and
        receiving at least one subsequent result using the user interface from at least a second test, similar to the first test, taken at at least a second time, later than the first time, comparing the at least second test with the at least first test, on at least one of multiplicity of general rose computers and the at least one controller computer for analyzing the at least one personal parameter of at least one user.

Preferably, analysis of at least one personal parameter of at least one user takes place partially at a general purpose computer at at least one user location and partially at the at least one controller computer.

In accordance with another preferred embodiment of the present invention analysis of at least one personal parameter of at least one user at a general purpose computer at at least one user location provides an analysis output which determines whether further analysis of the at least one personal parameter is carried out at the at least one controller computer.

Preferably, at least one of the general purpose computer and the at least one controller computer serves as a backup for another one of the general purpose computer and the at least one controller computer.

BRIEF DESCRIPTION OF THE DRAWINGS

The present invention will be understood and appreciated more fully from the following detailed description, taken in conjunction with the drawings in which:

FIG. 5C is a pictorial illustration of part of the medical condition sensing system of FIG. 1 being employed for electrocardiogram sensing;

FIG. 5F is a pictorial illustration of part of the medical condition sensing system of FIG. 1 being employed for hearing condition sensing;

FIG. 5H is a pictorial illustration of part of the medical condition sensing system of FIG. 1 being employed for vision testing;

FIG. 6A is a simplified functional block diagram of the system of FIG. 1 having the functionality shown in FIG. 5A;

FIG. 6E is a simplified functional block diagram of the system of FIG. 1 having the functionality shown in FIG. 5E;

FIG. 6G is a simplified functional block diagram of the system of FIG. 1 having the functionality shown in FIG. 5G;

FIG. 7A is a simplified flowchart illustrating the operation of the system of FIG. 1 in the operative environment of FIGS. 5A and 6A;

FIG. 7B is a simplified flowchart illustrating the operation of the system of FIG. 1 in the operative environment of FIGS. 5B and 6B;

FIG. 7C is a simplified flowchart illustrating the operation of the system of FIG. 1 in the operative environment of FIGS. 5C and 6C;

FIG. 7D is a simplified flowchart illustrating the operation of the system of FIG. 1 in the operative environment of FIGS. 5D and 6D;

FIG. 7E is a simplified flowchart illustrating the operation of the system of FIG. 1 in the operative environment of FIGS. 5E and 6E;

FIG. 7F is a simplified flowchart illustrating the operation of the system of FIG. 1 in the operative environment of FIGS. 5F and 6F;

FIG. 7G is a simplified flowchart illustrating the operation of the system of FIG. 1 in the operative environment of FIGS. 5G and 6G;

FIG. 7H is a simplified flowchart illustrating the operation of the system of FIG. 1 in the operative environment of FIGS. 5H and 6H;

FIG. 8A is an illustration of application of part of an exemplary decision table to personal parameters of a given person in the operative environment of FIG. 5A;

FIG. 8C is a an illustration of application of part of an exemplary decision table to personal parameters of a given person in the operative environment of FIG. 5C;

FIG. 8D is a an illustration of application of part of an exemplary decision table to personal parameters of a given person in the operative environment of FIG. 5D;

FIG. 8H is a an illustration of application of part of an exemplary decision table to personal parameters of a given person in the operative environment of FIG. 5H;

DETAILED DESCRIPTION OF PREFERRED EMBODIMENTS

Figure 1:
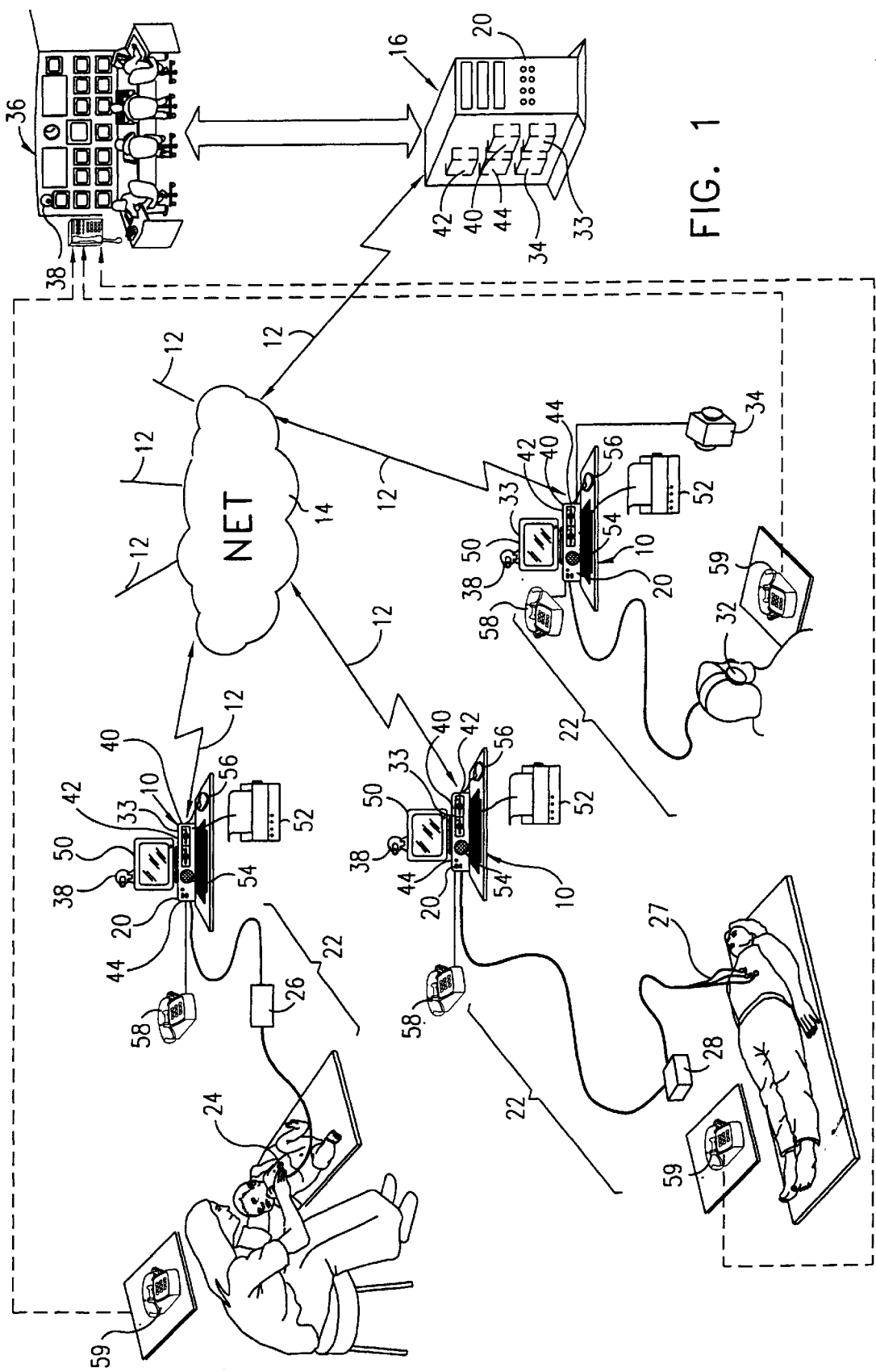
FIG. 1 is a simplified partially pictorial, partially block diagram illustration of a medical condition sensing system constructed and operative in accordance with a preferred embodiment of the present invention.

Reference is now made to FIG. 1, which is a simplified partially pictorial, partially block diagram illustration of a medical condition sensing system constructed and operative in accordance with a preferred embodiment of the present invention.

As seen in FIG. 1, the medical sensing system of the present invention comprises a multiplicity of general purpose computers 10, such as personal computers or communicators, disposed in user locations and connected via suitable wired or wireless connections 12 to a network 14, such as the Internet or other wide area network and via network 14 to at least one controller computer 16 remote from at least one of the user locations.

In accordance with a preferred embodiment of the invention, personal parameter measuring software 20 is resident on at least one of the general purpose computers 10 and/or on at least one controller computer 16 for measuring at least one personal parameter of at least one user of one of the general purpose computers. The personal parameters may be any suitable medical parameter, such as, for example, parameters relating to heart function, lung function, hearing, vision, alertness, physical appearance and perception as well as conventional medical indications such as weight, height, age, blood pressure, blood sugar level and other body fluid parameters, as well as various combinations of the foregoing.

Personal parameter measuring software 20 cooperates with personal parameter measuring equipment 22 which is preferably adapted to measure each type of personal parameter in association with a general purpose computer 10. Various types of personal parameter measuring equipment 22 may be provided to users of the system. For example, a stethoscope transducer 24 and lung sounds interface 26 may be provided for sensing lung sounds, electrocardiogram electrodes 27 and an electrocardiogram interface 28 may be provided for electrocardiogram measurements, and a hearing testing headset 32 and headset calibrator 34 may be provided for hearing testing.

It is appreciated that various calibration functionalities, which may be embodied in hardware, software or combinations thereof, may be provided as part of personal parameter measuring equipment 22 or for use therewith. The calibration functionalities may or may not involve communication with the controller computer 16 via the network 14. A given calibration functionality may operate automatically without operator intervention. Alternatively, a calibration functionality may require operator activity.

It is further appreciated that at every appropriate stage of operation, suitable instruction is provided to the user by the general purpose computer of the user. This instruction may be presented to the user in textual, audio or multi-media form and may be unidirectional or interactive. Preferably, suitable instruction is provided prior to calibration of personal parameter measuring equipment 22, prior to establishment of a baseline and prior to each test.

In accordance with a preferred embodiment of the present invention the medical condition sensing system of the present invention includes personal parameter reference generating software 33 resident on at least one of the general purpose computers or on at least one controller computer for establishing a reference for the at least one personal parameter. In this preferred embodiment, personal parameter comparison software, resident on at least one of the multiplicity of general purpose computers 10 and/or on at least one controller computer 16, compares at least one currently measured personal parameter with a corresponding reference and provides a comparison output.

The comparison output may be provided to the user by the general purpose computer 10 together with an action recommendation. Alternatively or additionally, it may be provided to a controller computer 16 for comparison with reference data stored on a central database 34 in order to provide additional information and recommendations to the user.

A manned center 36 may be associated with the controller computer 16 for providing a human interface and/or input as required. The manned center 36, which is preferably staffed by physicians or other health professionals, may be in direct telephone and preferably videophone contact with the user. To this end video cameras 38 are preferably provided both at the manned center 36 and at various user locations. Communication of outputs of the video cameras 38 may be effected via network connections 12 or alternatively in any other manner.

In accordance with a preferred embodiment of the present invention, acceptable ranges of values for various medical parameters used in present invention may be established by medical personnel in the manned center 36 in accordance with the personal characteristics of each given patient.

In accordance with one embodiment of the present invention, initial feedback to the user may be provided under certain conditions by a general purpose computer 10 without accessing the network 14 or the controller computer 16. In accordance with a preferred embodiment of the present invention, communication via the network 14 with the controller computer 16 may be actuated automatically by the system, for example in response to a sensed personal parameter or to the comparison output being beyond a certain threshold. Communication via the network with the controller computer 16 may also be initiated by a user, at the user's initiative.

In accordance with another preferred embodiment of the present invention, communication with the manned center may be actuated automatically by the system, for example in response to a sensed personal parameter or to the comparison output being beyond a given threshold. Communication with the manned center may also be initiated by a user, at the user's initiative. Communication between the user and the manned center may be via the network 14 and/or via conventional telephone or video-conference facilities.

Further in accordance with a preferred embodiment of the present invention, there is provided a recording and storage facility 40 for recording and storing sensed personal parameters. Facility 40 may be provided both at general purpose computers 10 and at controller computer 16.

There may also be provided for operation in the general purpose computer 10 or in the controller computer 16, software 42 providing a comparison facility for comparing personal parameters and a threshold facility for applying a threshold to a comparison result and providing an indication in response to exceedance of the threshold. Software 42 may include signal processing functionality, where appropriate.

Additionally in accordance with a preferred embodiment of the present invention, there is provided software 44 which controls measurement of the personal parameters and which may communicate via the network 14 with at least one remote computer. Software 44, which may reside both at general purpose computers 10 and at controller computer 16, preferably provides encryption encoding of information communicated between general purpose computers 10 and controller computer 16.

Preferably there is associated with each general purpose computer 10, at least one of a display 50, a printer 52 and an audio input/output transducer 54, as well as a user graphics interface such as a mouse 56 and an IP telephone 58. A conventional telephone 59 is preferably available at each user location.

In accordance with a preferred embodiment of the present invention communication between a general purpose computer 10 via the network 14 with another general purpose computer 10 or with a controller computer 16 is encoded or encrypted using conventional technology suitable for this purpose.

Preferably, the controller computer 16 is provided with access to medical databases which provide reference material for presentation to user as well as information which can be used by the controller computer 16 to evaluate measured personal parameters and to determine suitable courses of treatment therefor.

In accordance with a preferred embodiment of the present invention, the medical condition sensing system of the present invention includes:

a multiplicity of general purpose computers disposed in user locations and being connected via a computer network to at least one controller computer remote from at least one of the user locations;

personal parameter measuring software resident on at least one of the multiplicity of general purpose computers and at least one controller computer for measuring at least one personal parameter of at least one user; and personal parameter analysis software resident on at least one of the multiplicity of general purpose computers and the at least one controller computer for analyzing at least one personal parameter of at least one user.

The distributed processing thus provided has a number of advantages, including reduced communication load and increased speed of response. Furthermore, such processing enables medical confidentiality to be readily maintained in communications over the computer network.

Preferably, at least one of the general purpose computer and the at least one controller computer serves as a backup for another one of the general purpose computer and the at least one controller computer.

This backup functionality preferably enables the system to overcome computer failures at either a general purpose computer at a user location or a controller computer, by transferring computing functionality to another computer connected thereto via the computer network. This is extremely important for emergency situations. Should a network failure occur, but the general purpose computer at the user location is functioning, the user nevertheless can receive basic information as well as indications and recommendations as described hereinbelow from the general purpose computer. Additionally a bypass telephone connection may be employed to provide necessary communication with a user.

Figure 2:
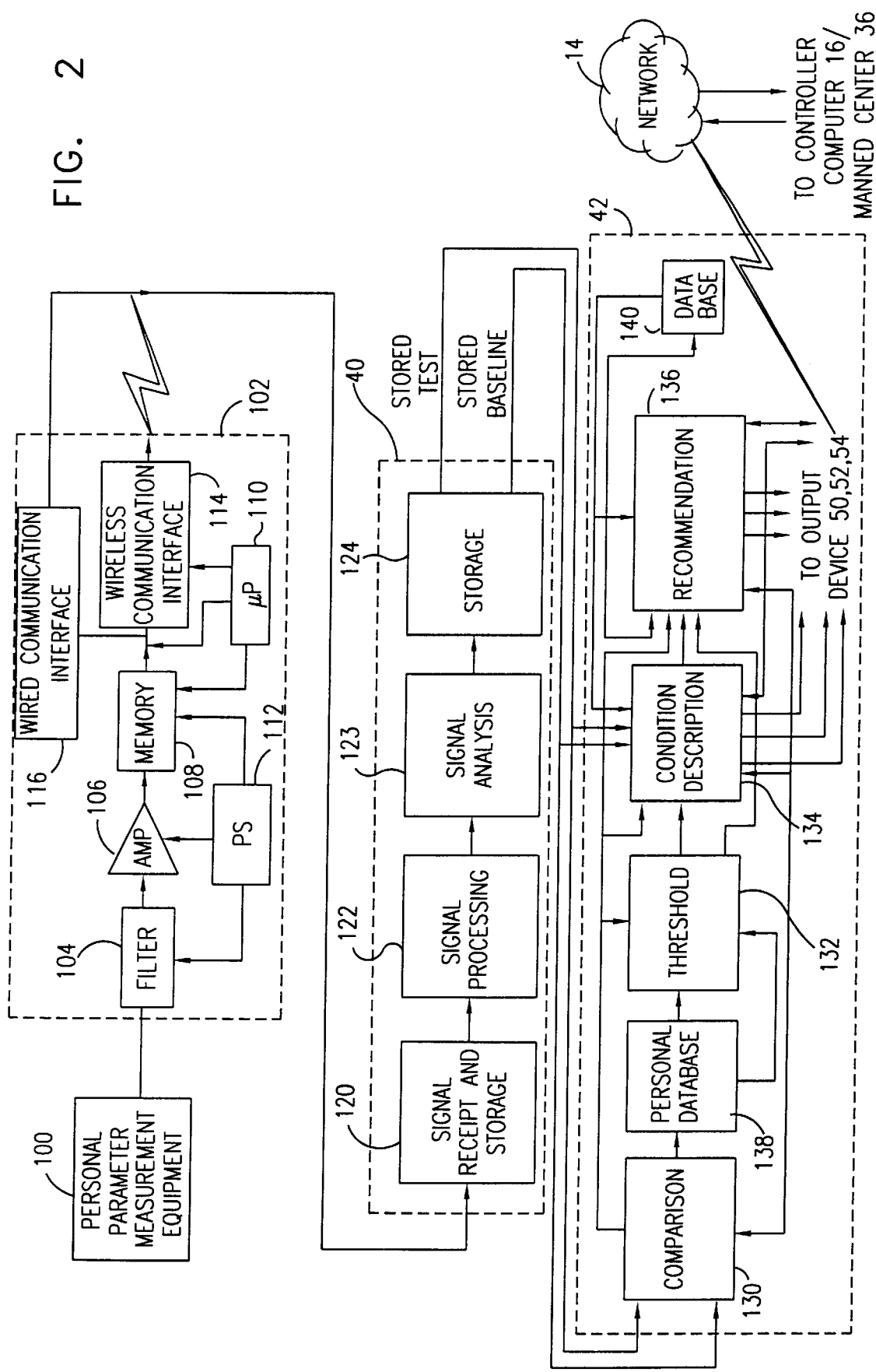
FIG. 2 is a simplified functional block diagram illustration of the general functionality of a general purpose computer and of a personal parameter transmitting interface, both forming part of the system of FIG. 1.

Reference is now made to FIG. 2, which is a simplified functional block diagram illustration of the general functionality of a general purpose computer and of an optional personal parameter transmitting interface, both forming part of the system of FIG. 1. It is appreciated that the personal parameter transmitting interface typically forms part of personal parameter measuring equipment 22 (FIG. 1) and may have different configurations depending on the personal parameter which is sought to be measured and, in certain cases, may be obviated. Examples of personal parameter transmitting interfaces that do include hardware are interfaces 26 and 28 shown in FIG. 1. An example where the interface may be obviated is the hearing testing equipment employing the headset 32 shown in FIG. 1, which may be connected directly to the general purpose computer and may employ the sound card thereof.

As seen in FIG. 2, personal parameter measurement equipment 100, such as stethoscope transducer 24 (FIG. 1), electrocardiogram electrodes 27 and headset 32, indicated generally at reference numeral 22 in FIG. 1, is coupled to optional personal parameter interface circuitry, designated generally by reference numeral 102. Circuitry 102 typically includes one or more of the following components: a filter 104, an amplifier 106, a memory 108, a microprocessor 110, a power supply 112, a wireless communications interface 114 and a wired communication interface 116. Where a memory 108 or a wireless interface 114 is provided, the interface circuitry 102 may be portable and thus particularly useful for emergency applications.

Typically the personal parameter interface circuitry 102 is coupled to a suitable port of a general purpose computer 10 (FIG. 1), such as a serial port, a sound or game port or a universal port and permits outputs to be supplied to the general purpose computer 10 for processing thereat.

Recording and storage facility 40 (FIG. 1) is provided preferably at general purpose computer 10 for recording and storing parameters received by the general purpose computer 10 during at least one test. Preferably, the recording and storage facility 40 comprises signal receipt and storage facility 120, a signal processing facility 122, a signal analysis facility 122 and an information storage facility 124. Optionally, any one or more of the foregoing functionalities may be obviated.

Software 42 (FIG. 1), which is preferably resident in general purpose computer 10, provides appropriate signal processing and comparison of parameters received by the general purpose computer 10 and may apply a threshold to a comparison result. Software 42 typically provides via the general purpose computer 10 an indication of exceedance or non-exceedance of the threshold along with suitable description of the situation which may be accompanied by recommendations for action.

Software 42 typically comprises a comparison functionality 130 which may receive information representing a stored baseline and/or a test and which may provide an output to a threshold functionality 132. A condition description functionality 134 preferably receives information relating to at least one of the stored baseline and the test and may also receive outputs of the comparison and threshold functionalities 130 and 132. The condition description functionality preferably provides outputs to one or more of output devices 50, 52 and 54 (FIG. 1) as well as optionally via network 14 to controller computer 16 and/or to manned center 36.

The condition description functionality may also provide an output to recommendation functionality 136, which preferably also receives inputs from comparison functionality 130 and threshold functionality 132.

In accordance with a preferred embodiment of the present invention the general purpose computer 10 may communicate with a remote computer, such as a controller computer 16 (FIG. 1), for obtaining additional reference data and possibly carrying out a comparison between the test data and reference data, thereby to provide further information to the user. Such further information may include a more detailed or precise description of the condition indicated by the test results which may be accompanied by a more detailed or precise recommendation for action. Information received via the network may be employed by the recommendation functionality 136 as well as by the condition description functionality 134.

Communication with a remote computer, such as a controller computer 16 may be initiated automatically by the general purpose computer 10 via the network 14, for example in response to a sensed personal parameter or a comparison output beyond a certain threshold. Communication via the network 14 with the controller computer may also be initiated by a user, at the user's initiative.

Software 42 preferably also includes a standard personal parameter database 138 which stores normal values of personal parameters for a given user or users. The information stored in database 138 is preferably employed by one or more of functionalities 130, 132, 134 and 136.

Condition description functionality 134 and recommendation functionality 136 preferably operate in association with a database 140 cm which stores acceptable ranges of outputs of comparison functionality 130, normalized for age, weight, height, sex and possibly other characteristics. This database may be used for normalizing sensed personal parameters as well as for determining whether a baseline value indicates a need for evaluation or even urgent medical attention. Database 140 is preferably employed to enable condition description functionality 134 and recommendation functionality 136 to take into account the variation in acceptable changes in various personal parameters due to variations in age, weight, height, sex and possibly other characteristics.

It is appreciated that any one or more of the functionalities and databases described hereinabove in the context of software 42 may be obviated in a given application.

Communication with a remote computer, such as a controller computer 16 (FIG. 1) via the network 14 may be actuated automatically in response to the output of comparison functionality 130, threshold functionality 132, condition description functionality 134 or recommendation functionality 136. Thus, when a sensed personal parameter or the comparison output lies beyond a certain threshold which may indicate either an emergency situation or a situation requiring controller intervention, communication is established immediately between the user's general purpose computer 10 and the controller computer 16 via the network.

Communication between the user and the manned center may be via the network 14 and/or via conventional telephone or video-conference facilities.

Figure 3:
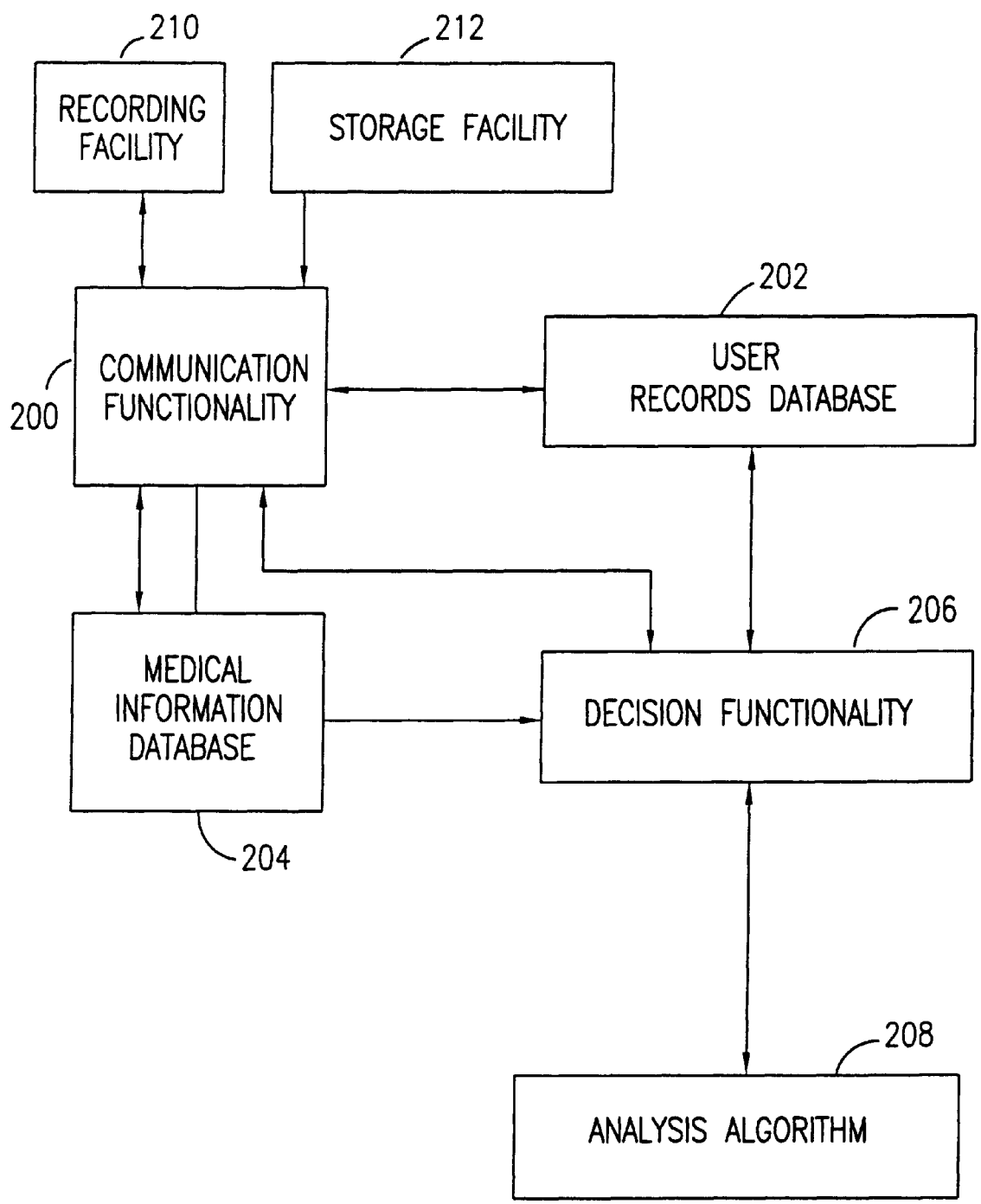
FIG. 3 is a simplified functional block diagram illustration of the general functionality of a controller computer forming part of the system of FIG. 1.

Reference is now made to FIG. 3, which is a simplified functional block diagram illustration of the general functionality of a controller computer forming part of the system of FIG. 1. The controller computer, such as controller computer 16 (FIG. 1) preferably includes a communications facility 200 which enables it to communicate with a user's general purpose computer 10 (FIG. 1) via the network 14 (FIG. 1). This communication may include receiving information from a user as to which parameter measurement functionality the user is implementing and downloading to the user suitable operating, reference and calibration software to carry out that functionality.

The controller computer also preferably includes a user records database 202, which interfaces with the communications facility 200 and maintains all relevant records of user information, and a medical information database 204 which stores medical reference information useful in making comparisons and recommendations. The user records database 202 stores personal details of each user, general medical information regarding each user and results of tests conducted by the user, using the medical condition sensing kits, which are transmitted to the controller computer 16. Normally, the personal details, general medical information and results of the tests conducted on the patient, which are stored in the user records database 202, are also stored in the personal database 138 of the user's general purpose computer 10.

The controller computer also preferably includes decision functionality 206 which enables it to make decisions based on patient parameter, comparison and threshold information received from a user's general purpose computer 10 via network 14, using an analysis algorithm 208, such may be specific to each medical information sensing functionality provided by the system. The decisions made by functionality 206 may include decisions whether to automatically connect the user to a manned center 36 (FIG. 1) and whether to automatically summon emergency assistance for the user.

As indicated above, the controller computer also stores software to be downloaded to a user's general purpose computer 10 in a software storage facility 212. The controller computer also preferably includes a recording facility 210 for recording all communications with a user.

Figure 4:
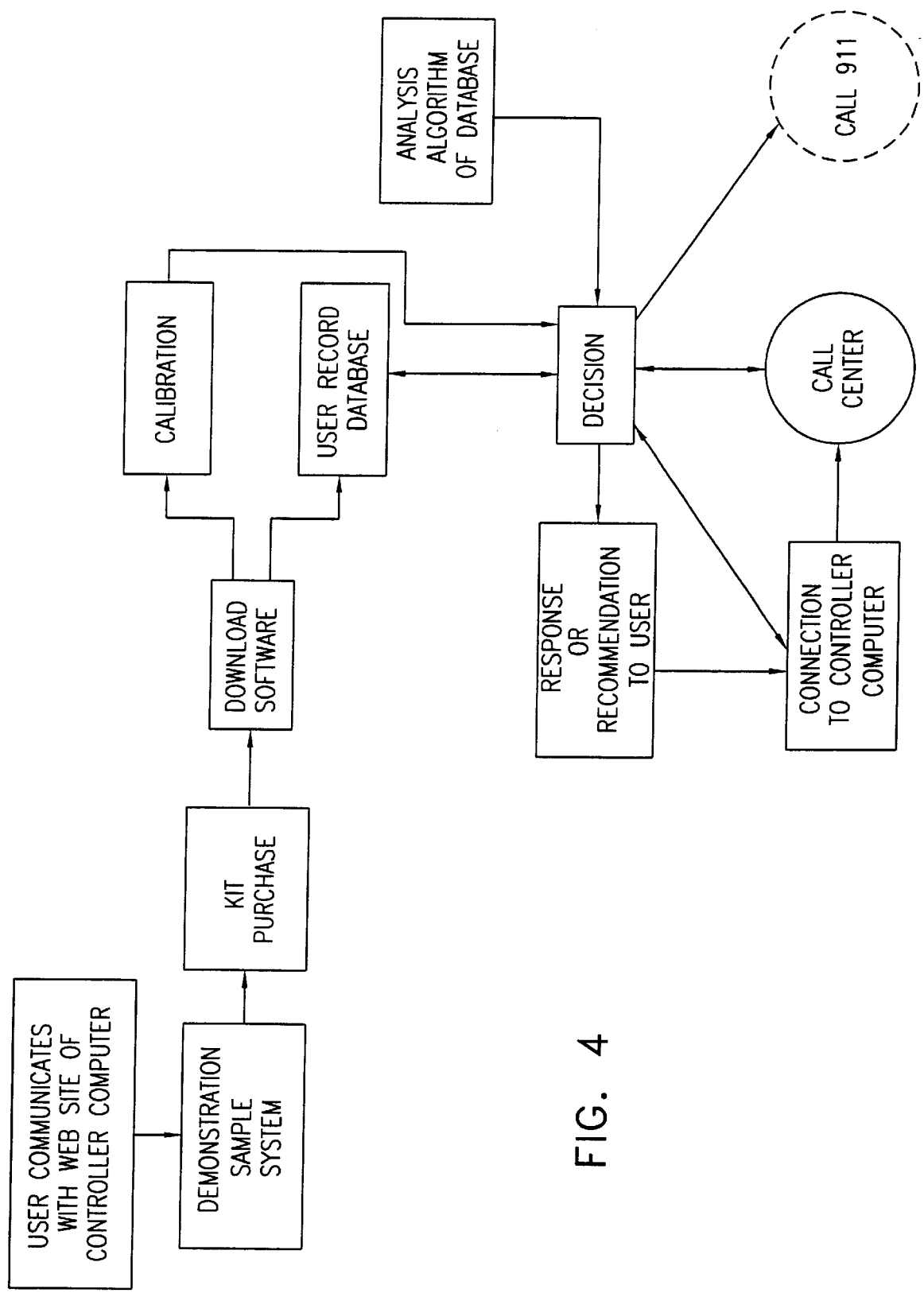
FIG. 4 is a simplified flow chart illustration of the general functionality of the controller computer forming part of the system of FIG. 1.

Reference is now made to FIG. 4, which is a simplified flow chart illustration of the general functionality of a controller computer forming part of the system of FIG. 1 and having the general structure described hereinabove with reference to FIG. 3.

Initial communication between a user's general purpose computer 10 (FIG. 1) and a controller computer, such as controller computer 16 (FIG. 1) preferably includes a user communicating with a web site of the controller computer 16, using communications functionality 200 (FIG. 3). In the course of this communications, the user may obtain demonstrations of various functionalities of system of the present invention and explanations regarding use of the system. The site may include transactional software enabling various medical condition sensing kits to be purchased by a user. Each such kit preferably includes all interfaces to be connected to the user's general purpose computer 10 and all necessary software to be installed by the user in the user's general purpose computer 10.

Alternatively or additionally the software may be downloaded by the user via the Internet or any other modality and the kit may be purchased or otherwise obtained not only from the web site but also from conventional retail sources.

Irrespective of the manner in which the kit is obtained by the user and the software is installed in the user's general purpose computer, the user is required to register with the user records database 202 (FIG. 3). As noted above, the user records database stores personal details of each user, general medical information regarding each user and results of tests conducted by the user, using the medical condition sensing kits, which are transmitted to the controller computer.

When the user wishes to use the medical condition sensing kit in communication with the controller computer, following current use registration, in many cases an appropriate calibration protocol is followed, preferably using software installed at the controller computer. Following calibration, as and when appropriate, a baseline determination is carried out, as needed.

Once any and all calibration and baseline determination steps have been followed, a test may be conducted using the medical condition sensing kit in cooperation with the user's general purpose computer 10 which is in communication with the controller computer 16. In the course of the test or thereafter, the test results may be processed by decision functionality 206 in accordance with an analysis algorithm 208, which is typically kit specific. The processing typically employs stored in the user records database 202, such as calibration data and baseline data, and may also employ general (i.e. not patient specific) medical data stored in the medical information database 204.

Following processing of the test results as described hereinabove, decisions and recommendations are preferably provided to the user, preferably via the web site and the Internet. Additionally or alternatively, responsive to the test results and their relationship with established thresholds for the specific patient or for the type of test generally, an automatic connection may be established between the user and the manned center 36 (FIG. 1), via the web site of the controller computer and/or other media such as a telephone or video conference connection. Additionally, where appropriate, emergency assistance may be summoned to the user automatically or with human intervention. Preferably, all communications with the user and other parties as well as the entire decision making record are recorded for archival purposes.

Figure 5A:
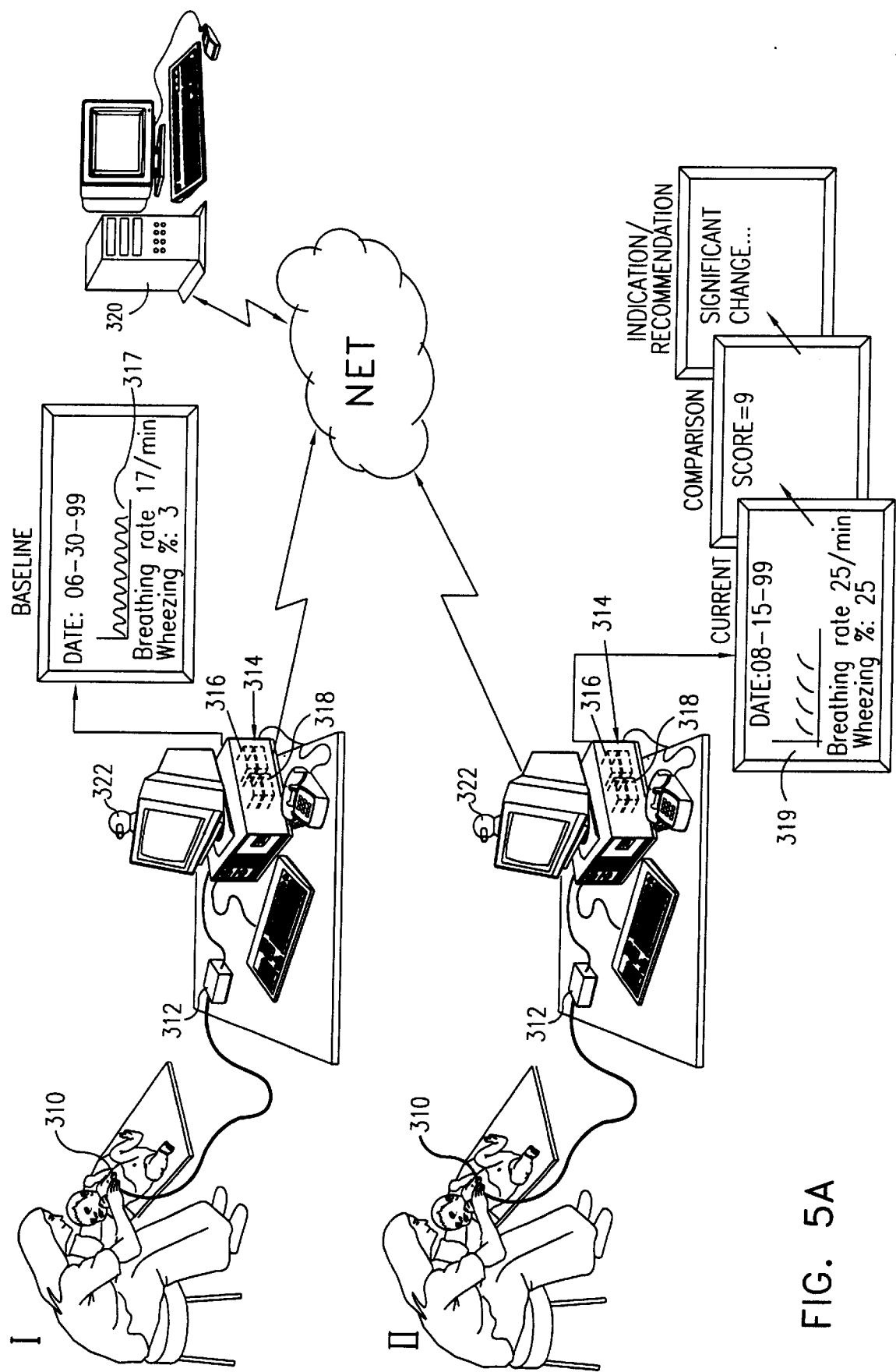
FIG. 5A is a pictorial illustration of part of the medical condition sensing system of FIG. 1 being employed for lung sounds condition sensing.

Reference is now made to FIG. 5A, which is a pictorial illustration of part of the medical condition sensing system of FIG. 1 being employed for lung sounds condition sensing. FIG. 5A shows two stages in lung sounds condition sensing, a first stage, indicated by designation I, at which a baseline reference is generated, and a second stage, indicated by designation II, at which an actual test is conducted. The context of FIG. 5A is typically a situation wherein a person, such as a child, has a possible respiration condition which is evidenced in lung sounds emitted during breathing.

In the environment of FIG. 5A, a user interface is provided which preferably includes a stethoscope transducer 310, such as transducer commercially available from Karmel Medical Acoustic Technologies Ltd. of Yokneam Illit, Israel. The stethoscope transducer 310 provides an electrical output typically via interface circuitry 312 to a suitable interface of a general purpose computer 10 (FIG. 1), here designated by reference numeral 314.

A recording and storage facility 40 (FIG. 1), here designated by reference numeral 316, at general purpose computer 314 is operative for recording and storing at least one baseline plot of lung sounds received by the general purpose computer 314 from stethoscope transducer 310 during at least one first test taken at least a first time, such as on Jun. 30, 1999. This first test is preferably carried out when the child is in apparent good health and shows no symptoms of respiratory distress and is employed to establish a baseline. The baseline result may be visualized by the waveform 317.

Software 42 (FIG. 1) here designated by reference numeral 318, which is preferably resident in general purpose computer 314, provides appropriate signal processing and comparison of lung sounds received by the general purpose computer 314 from stethoscope transducer 310 during a subsequent test taken at a a subsequent time, such as on Aug. 15, 1999. This second test is preferably carried out when the person shows symptoms of respiratory distress and may require attention. It is seen that waveform 319 differs from baseline waveform 317.

Software 318 compares the lung sounds received during the second test with the baseline established by at least one earlier test and may apply a threshold to the comparison result. Software 318 typically provides via the general purpose computer 314 an indication of exceedance or nonexceedance of the threshold along with suitable description of the situation which may be accompanied by recommendations for action.

Software 318 typically compares various breathing parameters such as the slope of the waveform, the area under the waveform and the relationship between various portions of the waveform.

A controller computer 16 (FIG. 1), here designated by reference numeral 320, preferably communicates, via the network 14 (FIG. 1), with software 318 for assisting in providing recommendations for action. Where a manned center 36 (FIG. 1) is provided, a human interface or human evaluation of the lung sounds may also be provided to the user. To enhance the efficacy of interface between the user and personnel in the manned center 36 (FIG. 1) a video camera 38 (FIG. 1), here designated by reference numeral 322, may be located at the user location to enable personnel in the manned center 36 to view the patient who is experiencing apparent breathing distress.

In accordance with another preferred embodiment of the present invention, communication with the manned center may be actuated automatically by the system, normally through the action of the controller computer 320, for example in response to lung sounds of a certain type or the output of a comparison of the currently sensed lung sounds with a baseline or with a standard reference which exceeds a threshold indicating a possibly critical condition or possibly improper use of the kit.

Reference is now made to FIG. 6A, which is a simplified functional block diagram of the system of FIG. 1 having the functionality of FIG. 5A, namely lung sounds condition sensing, typically in an environment wherein a person, such as a child, has a possible respiration condition which is evidenced in the lung sounds emitted during breathing.

In the environment of FIG. 5A, as illustrated in FIG. 6A, stethoscope transducer 310 provides a lung sounds waveform via interface circuitry 312 (FIG. 5A) to recording and storage facility 316 (FIG. 5A) of general purpose computer 314 (FIG. 5A). As noted above with reference to FIG. 5A, preferably a baseline is initially established by a test conducted in an environment wherein a person, such as a child, is apparently breathing normally. Thereafter, a further test may be conducted when the person has a possible respiration condition which is evidenced in the lung sounds emitted during breathing. In both cases, the resulting waveform received from stethoscope transducer 310 is processed using the functionality described hereinabove with reference to FIGS. 2, 3 and 4.

In the embodiment of FIG. 6A, interface circuitry 312 is preferably portable'so as to be readily brought to the location of the patient and preferably employs a band pass filter 344 which filters out sounds picked up by the stethoscope transducer 310 outside a desired band, typically 80–4000 Hz, which includes both lung sounds and wheezing noises. The output of filter 344 is amplified by an amplifier 346 and preferably supplied to a memory 348. A portable power supply 352 preferably supplies power to the foregoing components as well as to a wireless communication interface 354 and/or a wired communication interface 356 which output to general purpose computer 314 (FIG. 5A).

In the embodiment of FIG. 6A, preferably, the recording and storage facility 316 stores both a baseline lung sounds waveform and an actual test lung sounds waveform. A lung sounds signal receipt and storage facility 360 receives and stores the signal received from interface 312. A signal processing facility 362 removes unwanted signal artifacts, such as wheezing signals having a duration less than 150 msecs, and generally prepares the signal for analysis.

A signal analysis functionality 364 preferably performs the following functions on the lung sounds signals:

Determination of the breathing rate;

Determination of the time relationship between durations of inhalation and exhalation;

Derivation of the slopes of the waveform at various stages during inhalation and exhalation;

Sensing the frequency pattern of the lung sounds;

Determination of the percentage of the duration of both inhalation and exhalation that wheezing occurs;

Sensing the presence of noises and other characteristic sound patterns in the lung sounds;

Normalization of the above parameters for the age and height of the patient, using patient data from a personal database, typically forming part of software 318.

The outputs of the signal analysis functionality 364 for the signal is preferably stored in storage facility 366.

The above-described functionality provided by software 316 is applied initially to a baseline signal and thereafter to an actual test signal. The stored results for both the baseline signal and for the test signal are supplied to software 318.

Comparison functionality 130 (FIG. 2), here designated by reference numeral 370, which is included in software 318 (FIG. 5A), compares the lung sounds waveform and analysis data relating thereto stored by recording and storage facility 316 with a baseline lung sounds waveform and analysis data relating thereto, also stored by facility 316. Comparison functionality 370 preferably applies sensed differences therebetween to thresholding functionality 132 (FIG. 2), here designated by reference numeral 372, which may apply a threshold to the comparison result indicating whether the currently sensed lung sounds substantially different from the baseline. Threshold functionality may employ data received from a personal database 374, which may also provide data to signal analysis functionality 364 of software 316 for use in normalizing analysis data for given patient parameters.

Outputs of comparison functionality 370 and thresholding functionality 372 are preferably provided to condition description functionality 134 (FIG. 2) here designated by reference numeral 375, which provides a description of the sensed respiratory condition via an output device, such as a display 50, printer 52 and audio transducer 54 (FIG. 1). Outputs provided by comparison functionality 370, thresholding functionality 372 and condition description functionality 375 may be further processed by recommendation functionality 136 (FIG. 2) here designated by reference numeral 376, which may provide indications/recommendations to the user via any one or more of display 50, printer 52 or transducer 54.

Preferably, both condition description functionality 375 and recommendation functionality 376 receive reference data from a database 140 (FIG. 2), designated by reference numeral 380, which stores acceptable ranges of outputs of comparison functionality 370, normalized for age, weight, height, sex and possibly other characteristics. Database 380 is preferably employed to enable condition description functionality 375 and recommendation functionality 376 to take into account the variation in acceptable changes in various personal parameters due to variations in age, weight, height, sex and possibly other characteristics.

Communication with a remote computer, such as a controller computer 16 (FIG. 1) may be initiated automatically by the general purpose computer 314 via the network 14, for example in response to the output of comparison functionality 370, threshold functionality 372, condition description functionality 375 or recommendation functionality 376, indicating, for example a possibly acute respiratory condition or a suspected misuse of the kit.

Thus, when a sensed personal parameter or the comparison output lies beyond a certain threshold which may indicate either an emergency situation or a situation requiring controller intervention, communication is established immediately between the user's general purpose computer 314 and the controller computer 16 (FIG. 1) via the network 14 (FIG. 1). As noted above, communication via the network 14 with the controller computer 16 may also be initiated by a user, at the user's initiative.

Reference is now made to FIG. 7A, which is a simplified flowchart illustrating the operation of the system of FIG. 1 in the operative environment of FIGS. 5A and 6A.

Initially the user accesses a system web site and carries out the initial communications and actions described hereinabove with respect to FIG. 4, which include the acquisition of a lung sound test kit including a stethoscope transducer and download of operating baseline establishment software to the user's general purpose computer 314 (FIG. 5A) from the controller computer 320 (FIG. 5A) or otherwise. The user registers with the user records database 202 of the controller computer (FIG. 3). As noted above, the user records database stores personal details of each patient for which the lung sounds sensing kit is to be used as well as general medical information regarding each such patient and results of tests conducted on that patient, using the lung sounds sensing kit, to the extent that such results are transmitted to the controller computer. Preferably, the information entered by the user into the user records database 202 of the controller computer 320. Thus, the personal details, general medical information and the results of the tests conducted on the patient, which are stored in the user records database 202, are also stored in the personal database 374 of the user's general purpose computer 314.

When the user is ready to perform a baseline establishing lung sounds test, following current use registration, a baseline determination is carried out typically in the following manner:

The lung sounds waveform is recorded at the user's general purpose computer 314.

The breathing rate is derived at the user's general purpose computer 314.

The time relationship between durations of inhalation and exhalation is derived at the user's general purpose computer 314.

The slopes of the waveform at various stages during inhalation and exhalation are derived at the user's general purpose computer 314.

The frequency pattern of the lung sounds is sensed at the user's general purpose computer 314.

The presence of noises and other characteristic sound patterns in the lung sounds is sensed at the user's general purpose computer 314. These noises and other characteristic sound patterns are preferably analyzed automatically to provide an output indication of frequency and amplitude.

Some of the above parameters are preferably normalized for the age and height of the patient.

It is appreciated that should one or more baseline values differ from expected values to a medically significant extent, such as that described hereinbelow with reference to FIG. 8A, appropriate indications/recommendations may be provided immediately to the user and the controller computer and the manned center may be employed as appropriate.

At a later time, when a test is carried out on the same patient who may be experiencing apparent respiratory distress, preferably all of the above listed parameters are measured and analyses are performed. Some of the above parameters are preferably normalized for the age and height of the patient.

At least some of the foregoing parameters as well as possibly other parameters are employed by operating software installed at the user's general purpose computer 314. Some or all of the parameters are preferably stored both at the user's general purpose computer 314 and in user records database 202 at the controller computer 320.

The general purpose computer 314 preferably determines the differences between the baseline values and the current test values for the various parameters and analysis results and preferably indicates both the absolute difference and the percentage difference.

Based on the calculated differences between the baseline and the current test results, and using the information contained in databases 374 and 380, the operating software installed at the user's general purpose computer 314 is preferably operative to provide a condition description and recommendations to the user via the user's general purpose computer. The user's general purpose computer 314 may also employ inputs from the controller computer 320 in providing the condition description and recommendations to the user.

Depending on the comparison results and the recommendations, the user's computer may provide to the controller computer 320 the comparison results and possibly some or all of the test and baseline information.

The controller computer may analyze the comparison results and possibly some or all of the test and baseline information and provide results of the analysis to the user via the user's general purpose computer.

Preferably, the controller computer 320 makes a determination as to whether to contact a manned center 36. The user may make an independent determination whether to contact the manned center 36. A user's decision to utilize the services of the manned center which is not supported by the decision of the controller computer 320 may incur an additional charge, depending on the financial arrangements with the user.

Preferably, the condition description and recommendations are provided in accordance with a decision table, an example of which is provided in FIG. 8A.

The decision table of FIG. 8A is merely exemplary and illustrates the application of typical decision and recommendation functionality to a typical patient, a 10 year child of height 140 cm.

As noted above, based on the application of the decision and indication/recommendations functionality, an indication/recommendations such as "INSIGNIFICANT CHANGE IN LUNG SOUNDS/NO ACTION REQUIRED", "POSSIBLY SIGNIFICANT CHANGE IN LUNG SOUNDS/CONTACT PHYSICIAN/REPEAT TEST", "SIGNIFICANT CHANGE IN LUNG SOUNDS I IMMEDIATELY INITIATE PHYSICIAN ORDERED TREATMENT/CONTACT PHYSICIAN IMMEDIATELY" and "HIGHLY SIGNIFICANT CHANGE IN LUNG SOUNDS/OBTAIN EMERGENCY TREATMENT IMMEDIATELY" may be made. In certain cases where the computer is unable to provide a reliable indication/ recommendation due to technical difficulties with the test, an indication such as "BECAUSE OF TECHNICAL PROBLEMS RECOMMENDATION UNAVAILABLE/ CONTACT YOUR PHYSICIAN/REPEAT TEST" may be provided.

Additionally or alternatively, an automatic connection may be made to the controller computer 320 which may apply decision functionality similar to that used by the user's general purpose computer, but preferably including additional informational resources, such as breathing pattern analysis and lung noise analysis. The controller computer may also make any of the above-listed recommendations to the user. Alternatively or additionally, an automatic connection may be made to the manned center 36 (FIG. 1) wherein a human operator, such as a physician may review all of the personal parameters, analyses thereof and additional available medical information and make appropriate recommendations for action.

As noted above, complete records of all communications between the user and both the controller computer 120 and the manned center are maintained at the controller computer for future reference.

Turning to FIG. 8A, it is seen that for each of a plurality of relevant parameters, such as breathing rate, the ratio of durations of inhalation and exhalation, the percentage of the duration of inhalation at which wheezing noises are heard and the percentage of the duration of exhalation at which wheezing noises are heard, predicted, baseline and current test values are provided. Ratios and differences are calculated, as well as the ratio of the difference between the current test and the baseline to the baseline (D/B). Additionally or alternatively, the differences between a current test and previous tests and/or predicted values, as from databases 138 and 140 (FIG. 2), for the same patient may be determined and used.

The differences are preferably categorized as to their significance and the number of parameters falling within each category are noted. It is appreciated that various parameters may be given different weighting. All of the relevant parameters are taken into account with their respective weighting and a total, suitably weighted, value is used to determine which indications/recommendations are provided to the user and whether to utilize the analysis of the controller computer 320 and/or to engage the services of the manned center 36 (FIG. 1).

In the specific example shown in FIG. 8A, four categories, each having a different weighting, are defined. Category A includes parameters having a current to baseline difference or (D/B) ratio less than 15% and is given a weight of 0. Category B includes parameters having a current to baseline difference or (D/B) ration between 15% and 30% and is given a weight of 1. Category C includes parameters having a current to baseline difference or (D/B) ratio of between 30% and 40% and is given a weight of 2. Category D includes parameters having a current to baseline difference or (D/B) ratio exceeding 40% and is given a weight of 4.

It is appreciated that differences in different parameters may be measured in different ways, as most appropriate. For example in FIG. 8A, the differences in the breathing rate and the inhalation/exhalation duration ratio are measured as the ratio of current to baseline values. The differences in the wheezing percentage during both inhalation and exhalation are measured by subtracting the baseline value from the current value.

Thus it is seen in FIG. 8A that one parameter, namely wheezing percentage during inhalation, falls within Category A and one parameter, namely wheezing percentage during exhalation, falls within Category B. No parameters fall within Category C. Two parameters, breathing rate and inhalation/exhalation duration ratio fall within Category D. The resulting total weighted score is thus 9.

The relationship between weighted scores and indications/recommendations for the example shown in FIG. BA, is typically as follows:

| Weighted Score | Indication/Recommendation |
| --- | --- |
| 0–2 | "INSIGNIFICANT CHANGE IN LUNG SOUNDS/ NO ACTION REQUIRED" |
| 3–4 | "POSSIBLY SIGNIFICANT CHANGE IN LUNG SOUNDS/ CONTACT PHYSICIAN/REPEAT TEST" |
| 5–8 | "SIGNIFICANT CHANGE IN LUNG SOUNDS/ IMMEDIATELY INITIATE PHYSICIAN ORDERED TREATMENT/CONTACT PHYSICIAN IMMEDIATELY" |
| 9+ | "HIGHLY SIGNIFICANT CHANGE IN LUNG SOUNDS/ OBTAIN EMERGENCY TREATMENT IMMEDIATELY" |

Accordingly, the recommendation in the example of FIG. 8A is "HIGHLY SIGNIFICANT CHANGE IN LUNG SOUNDS/OBTAIN EMERGENCY TREATMENT IMMEDIATELY".

It is a particular feature of the present invention that multiple levels of detail and analysis may be provided. The initial and lowest level of detail and analysis, such as that described hereinabove, may be provided by the user's general purpose computer. A higher level of detail and analysis may be provided by the controller computer which employs resources, including both information and analysis tools, which may not be available to the user's general purpose computer, and the manned center 36 (FIG. 1) which adds a real time human health professional input, which may be interactive with the user and/or the patient using both audio and video communication facilities.

It is appreciated that when a particularly extreme difference is sensed in even one parameter, an emergency recommendation may be provided, irrespective of the status of the remaining parameters.

Preferably a full test and analysis report is prepared by the user's general purpose computer, which may incorporate inputs from the controller computer and the manned center as appropriate. This report may be printed out at the user location and may also be communicated via the network to any appropriate medical personnel or facility.

Figure 5B:
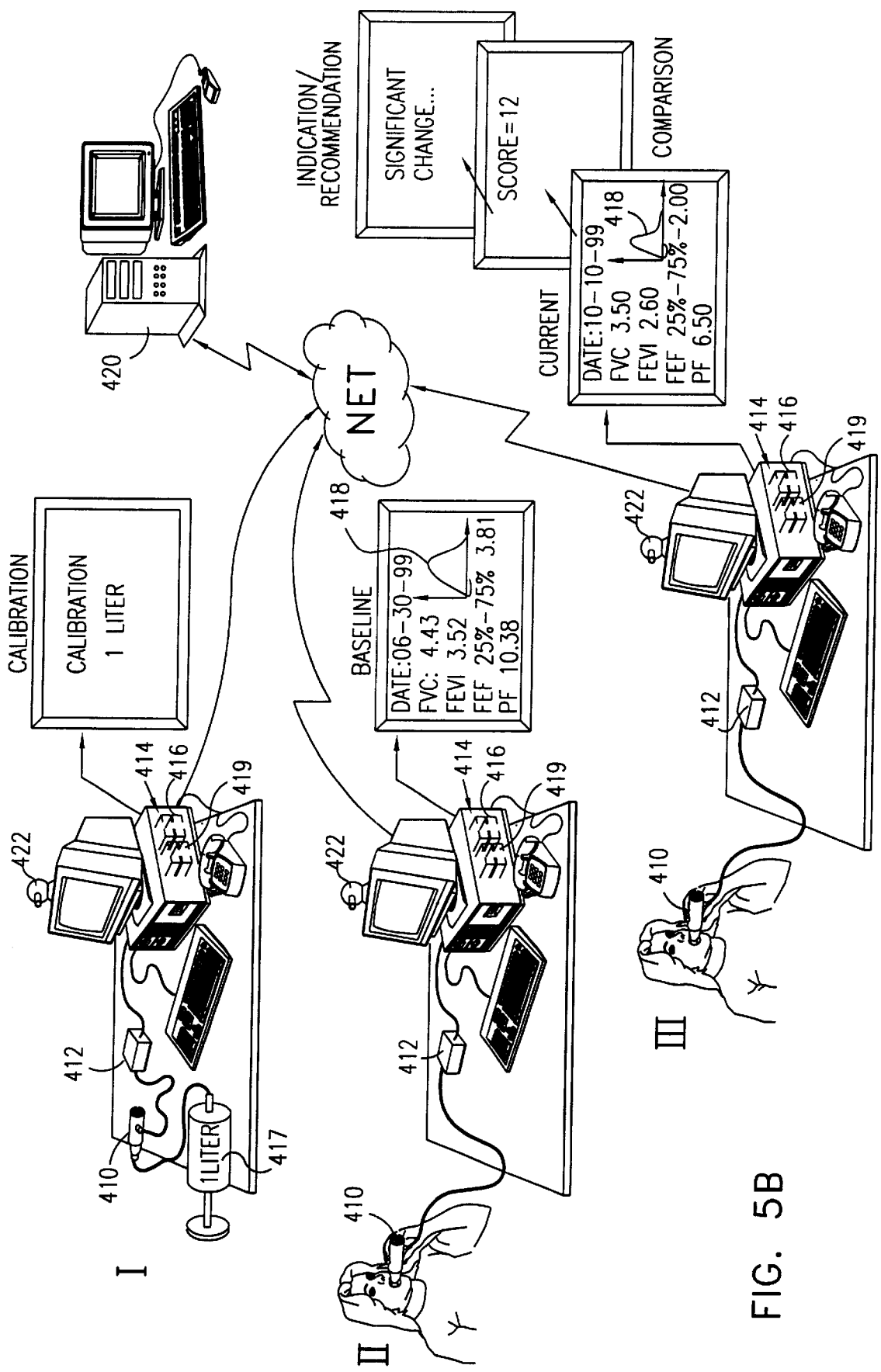
FIG. 5B is a pictorial illustration of part of the medical condition sensing system of FIG. 1 being employed for lung function condition sensing.

Reference is now made to FIG. 5B, which is a pictorial illustration of part of the medical condition sensing system of FIG. 1 being employed for lung function testing. FIG. 5B shows three stages in lung function testing, a first stage, indicated by designation I, at which calibration takes place; an optional second stage, indicated by designation II, at which a baseline reference is generated and a third stage, indicated by designation III, at which an actual test is conducted. The context of FIG. 5B is typically a situation wherein a person has a possible respiration condition which is evidenced in shortness of breath.

In the environment of FIG. 5B, a user interface is provided which preferably includes a flowmeter transducer 410, such as a Spirolyser SPL-10 flowmeter commercially available from F.I.M. SA of Lyon, France. The flowmeter transducer 410 typically provides an electrical output typically via interface circuitry 412, typically incorporated therein, to a suitable interface of a general purpose computer 10 (FIG. 1), here designated by reference numeral 414. Preferably, interface circuitry 412 is incorporated within a housing which also encloses flowmeter transducer 410.

A recording and storage facility 40 (FIG. 1), here designated by reference numeral 416, at general purpose computer 414 is operative for recording and storing calibration data and at least one baseline plot of lung function, typically a plot of forced expirium, received by the general purpose computer 414 from flowmeter transducer 410.

Prior to generating a baseline plot of lung function, the flowmeter transducer 410 is calibrated, as indicated at I in FIG. 5B. A syringe 417 containing a known amount of air, typically one liter, is employed to supply the known quantity to the flowmeter transducer 410. The software contained in the user's general purpose computer automatically calibrates the sensed output of the flowmeter transducer 410 to the fixed volume.

Following calibration of the flowmeter transducer 410, the baseline plot is generated by carrying out a baseline test, as seen at II in FIG. 5B. This baseline test is preferably carried out when the person is in apparent good health and shows no symptoms of respiratory distress.

Software 42 (FIG. 1), here designated by reference numeral 419, which is preferably resident in general purpose computer 414, provides appropriate signal processing and comparison of lung function indications received by the general purpose computer 414 from flowmeter transducer 410. Software 419 preferably provides an indication of average expiration flow rate during that portion of the expirium at which between 25% and 75% of the air in the lungs has been expelled.

Following establishment of the baseline reference, an actual test is carried out at a subsequent time, as indicated at III in FIG. 5B. The actual test is preferably carried out when the person shows symptoms of respiratory distress and may require attention. It is seen that the test results for the actual test, shown at III, differ from the test results for the baseline reference, shown at II.

Software 419 compares the lung function received during the actual test with the baseline established by at least one earlier test and may apply a threshold to the comparison result. Software 419 typically provides via the general purpose computer 414 an indication of exceedance or non-exceedance of the threshold along with suitable description of the situation which may be accompanied by recommendations for action.

Software 419 typically compares various breathing parameters such as the forced expirium waveform 418, the Forced Vital Capacity (FVC), the Forced Expiratory Volume during the first second of the forced expirium and the peak flow rate (PF) and the average expiration flow rate during that portion of the expirium at which between 25% and 75% of the air in the lungs has been expelled (FEF 25%–75%).

As described hereinabove, a controller computer 16 (FIG. 1), here designated by reference numeral 420, preferably communicates with software 419 for assisting in providing recommendations for action. Where a manned center 36 (FIG. 1) is provided, a human interface or human evaluation of the lung function may also be provided to the user. To enhance the efficacy of interface between a user and personnel in the manned center 36 (FIG. 1) a video camera 38 (FIG. 1), here designated by reference numeral 422, may be located at the user location to enable personnel in the manned center 36 to view the patient who is experiencing apparent breathing distress.

In accordance with another preferred embodiment of the present invention, communication with the manned center may be actuated automatically by the system, normally through the action of the controller computer 420, for example in response to lung function of a certain type or the output of a comparison of the currently sensed lung function with a baseline or with a standard reference which exceeds a threshold indicating a possibly critical condition or possibly improper use of the kit.

Figure 6B:
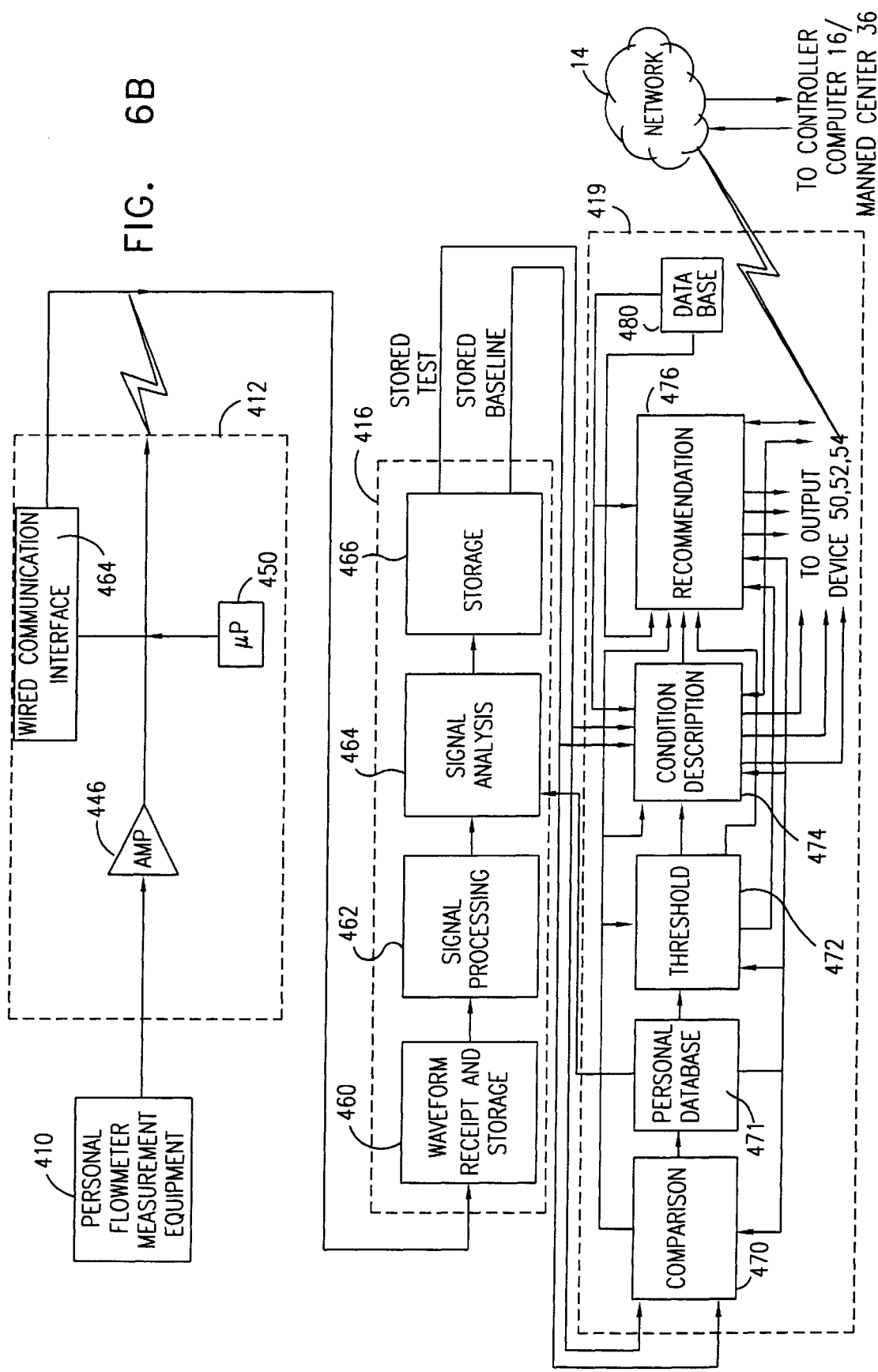
FIG. 6B is a simplified functional block diagram of the system of FIG. 1 having the functionality shown in FIG. 5B.

Reference is now made to FIG. 6B, which is a simplified functional block diagram of the system of FIG. 1 having the functionality of FIG. 5B, namely lung function testing, typically in an environment wherein a person has a possible respiration condition which is evidenced in the lung function indications sensed during breathing.

In the environment of FIG. 5B, as illustrated in FIG. 6B, flowmeter transducer 410 provides a lung function waveform via interface circuitry 412 (FIG. 5B) to recording and storage facility 416 (FIG. 5B) of general purpose computer 414 (FIG. 5B). As noted above with reference to FIG. 5B, preferably a baseline is initially established by a test conducted in an environment wherein a person is apparently breathing normally. Thereafter, a further test may be conducted when the person has a possible respiration condition which is evidenced in the lung function parameters sensed during breathing. In both cases, the resulting waveform received from flowmeter transducer 410 is processed using the functionality described hereinabove with reference to FIGS. 2, 3 and 4.

In the embodiment of FIG. 6B, interface circuitry 412 preferably employs an amplifier 446 which outputs via a wired communication interface 464 which is coupled to general purpose computer 414 (FIG. 5B). A microprocessor 450 may be provided to govern the operation of the flowmeter transducer 410 and to perform other functions.

In the embodiment of FIG. 6B, preferably the recording and storage facility 416 stores both baseline lung function data and actual test lung function data. A lung function waveform receipt and storage facility 460 receives and stores data received from interface 412. A signal processing facility 462 removes unwanted data artifacts and generally prepares the data for analysis.

A signal analysis functionality 464 preferably performs the following functions on the lung function data:

For both the baseline and the actual test data, determination of various breathing parameters such as the forced expirium waveform 418 (FIG. 5B), the Forced Vital Capacity (FVC), the Forced Expiratory Volume during the first second of the forced expirium (FEV1) as well as the peak flow rate (PF) and the average expiration flow rate during that portion of the expirium at which between 25% and 75% of the air in the lungs has been expelled (FEF 25%–75%).

The outputs of the signal analysis functionality 464 are preferably stored in storage facility 466.

The above-described functionality provided by software 416 is applied initially to a baseline signal and thereafter to an actual test signal. The stored results for both the baseline signal and for the test signal are supplied to software 419.

Software 419 preferably comprises comparison functionality 130 (FIG. 2), here designated by reference numeral 470, which compares the lung function analysis data relating to an actual test, stored by recording and storage facility 466 with baseline lung function analysis data also stored by facility 466 and preferably also with expected values for such lung functional analysis data which may be received from personal database 140 (FIG. 2) here designated by reference numeral 471.

The comparison functionality 470 preferably provides comparison of measured, predicted and baseline values of various breathing parameters such as the forced expirium waveform 418 (FIG. 5B), the Forced Vital Capacity (FVC), the Forced Expiratory Volume during the first second of the forced expirium (FEV1) as well as the peak flow rate (PF) and the average expiration flow rate during that portion of the expirium at which between 25% and 75% of the air in the lungs has been expelled (FEF 25%–75%).

The comparison functionality 470 preferably applies sensed differences therebetween to thresholding functionality 132 (FIG. 2), here designated by reference numeral 472, which may apply a threshold to the comparison result indicating whether the currently sensed lung function substantially different from the baseline and/or from the expected values therefor. Threshold functionality 472 may employ data received from a personal database 471, which may also provide data to signal analysis functionality 464 of software 416 for use in normalizing analysis data for given patient parameters.

Outputs of comparison functionality 470 and thresholding functionality 472 are preferably provided to condition description functionality 134 (FIG. 2) here designated by reference numeral 474, which provides a description of the sensed respiratory condition via an output device, such as a display 50, printer 52 and audio transducer 54 (FIG. 1). Outputs provided by comparison functionality 470, thresholding functionality 472 and condition description functionality 474 may be further processed by recommendation functionality 136 (FIG. 2) here designated by reference numeral 476, which may provide indications/recommendations to the user via any one or more of display 50, printer 52 or transducer 54.

Preferably, both condition description functionality 474 and recommendation functionality 476 also receive reference data from database 471.

Preferably, both condition description functionality 474 and recommendation functionality 476 receive reference data from a database 140 (FIG. 2), here designated by reference numeral 480, which stores acceptable ranges of outputs of comparison functionality 470, normalized for age, weight, height, sex and possibly other characteristics. Database 480 is preferably employed to enable condition description functionality 474 and recommendation functionality 476 to take into account the variation in acceptable changes in various personal parameters due to variations in age, weight, height, sex and possibly other characteristics.

Communication with a remote computer, such as a controller computer 16 (FIG. 1) may be initiated automatically by the general purpose computer 414 via the network 14, for example in response to the output of comparison functionality 470, threshold functionality 472, condition description functionality 474 or recommendation functionality 476, indicating, for example a possibly acute respiratory condition or a suspected misuse or malfunction of the kit.

Thus, when one or more sensed lung function parameters or the comparison output lies beyond a certain threshold which may indicate either an emergency situation or a situation requiring controller intervention, communication is established immediately between the user's general purpose computer 414 and the controller computer 16 (FIG. 1) via the network 14 (FIG. 1). Communication via the network 14 with the controller computer 16 may also be initiated by a user, at the user's initiative.

Where a manned center 36 (FIG. 1) is provided, a human interface or human evaluation may also be provided to the user. It is thus possible for medical personnel in the manned center 36 to directly view the patient while hearing the lung function directly and speaking with the user.

Reference is now made to FIG. 7B, which is a simplified flowchart illustrating the operation of the system of FIG. 1 in the operative environment of FIGS. 5A and 6A.

Initially the user accesses a system web site and carries out the initial communications and actions described hereinabove with respect to FIG. 4, which include the acquisition of a lung function test kit including flowmeter transducer 410, interface 412 and calibration syringe 417 (FIG. 5B) and download of operating baseline establishment software to the user's general purpose computer 414 (FIG. 5B) from the controller computer 420 (FIG. 5B) or otherwise.

The user registers with the user records database 202 of the controller computer (FIG. 3). As noted above, the user records database stores personal details of each patient for which the lung function sensing kit is to be used as well as general medical information regarding each such patient and results of tests conducted on that patient, using the lung function sensing kit, to the extent that such results are transmitted to the controller computer. Preferably, the information entered by the user into the user records database of the controller computer 420 and the results of the tests conducted on the patient, which are stored in the user records database 202, are also stored in the personal database 471 of the user's general purpose computer 414.

Calibration of the flowmeter 410 is preferably carried out by using syringe 417 to cause a measured amount of air, typically 1 liter, to pass through the flowmeter 410. The output of the flowmeter 410 is adjusted, as necessary, to provide an output indicating the measured amount of air.

When the user is ready to perform a baseline establishing lung function test, following current use registration and calibration of the flowmeter 410, a baseline test is carried out as seen at II in FIG. 5B. This baseline test is preferably carried out when the person is in apparent good health and shows no symptoms of respiratory distress.

Software 419 provides appropriate signal processing and comparison of lung function parameters received by the general purpose computer 414 from flowmeter transducer 410. Software 419 preferably provides an indication of average expiration flow rate during that portion of the expirium at which between 25% and 75% of the air in the lungs has been expelled.

It is appreciated that should one or more baseline values differ from expected values to a medically significant extent, such as that described hereinbelow with reference to FIG. 8B, appropriate indications/recommendations may be provided immediately to the user and the controller computer and the manned center may be employed as appropriate.

Following establishment of the baseline reference, an actual test is carried out at a subsequent time, as indicated at III in FIG. 5B. The actual test is preferably carried out when the person shows symptoms of respiratory distress and may require attention. Some or all of the parameters are preferably stored both at the user's general purpose computer 414 and in user records database 202 at the controller computer 420. Some of the above parameters are preferably normalized for the age and height of the patient.

Software 419 compares the lung function received during the actual test with the baseline established by at least one earlier test and may apply a threshold to the comparison result. Software 419 typically provides via the general purpose computer 414 an indication of exceedance or non-exceedance of the threshold along with suitable description of the situation which may be accompanied by recommendations for action.

Software 419 typically compares various breathing parameters such as the forced expirium waveform 418, the Forced Vital Capacity (FVC), the Forced Expiratory Volume during the first second of the forced expirium and the peak flow rate (PF) and the average expiration flow rate during that portion of the expirium at which between 25% and 75% of the air in the lungs has been expelled (FEF 25%–75%).

At least some of the foregoing parameters as well as possibly other parameters are employed by operating software installed at the user's general purpose computer 414.

At a later time, when a test is carried out on the same patient who may be experiencing apparent respiratory distress, preferably all of the above listed parameters are measured and analyses are performed.

The general purpose computer 414 preferably determines the differences between the baseline values and the current test values for the various parameters and analysis results and preferably indicates both the absolute difference and the percentage difference.

Based on the calculated differences between the baseline and the current test results, and using the information contained in databases 471 and 480, the operating software installed at the user's general purpose computer 414 is preferably operative to provide a condition description and recommendations to the user via the user's general purpose computer. The user's general purpose computer 414 may also employ inputs from the controller computer 420 in providing the condition description and recommendations to the user.

Depending on the comparison results and the recommendations, the user's computer may provide to the controller computer 420 the comparison results and possibly some or all of the test and baseline information.

The controller computer may analyze the comparison results and possibly some or all of the test and baseline information and provide results of the analysis to the user via the user's general purpose computer.

Preferably, the controller computer 420 makes a determination as to whether to contact a manned center 36. The user may make an independent determination whether to contact the manned center 36. A user's decision to utilize the services of the manned center which is not supported by the decision of the controller computer 420 may incur an additional charge, depending on the financial arrangements with the user.

Figure 8B:
FIG. 8B is a an illustration of application of part of an exemplary decision table to personal parameters of a given person in the operative environment of FIG. 5B.

Preferably, the condition description and recommendations are provided in accordance with a decision table, an example of which is provided in FIG. 8B.

The decision table of FIG. 8B is merely exemplary and illustrates the application of typical decision and recommendation functionality to a typical patient, a 37 year male of height 172 cm and weight 67 kg.

Based on the application of the decision and indication/recommendation functionality, an indication/recommendation such as "INSIGNIFICANT CHANGE IN LUNG FUNCTIONS/NO ACTION REQUIRED", "POSSIBLY SIGNIFICANT CHANGE IN LUNG FUNCTIONS/CONTACT PHYSICIAN/REPEAT TEST", "SIGNIFICANT CHANGE IN LUNG FUNCTIONS/IMMEDIATELY INITIATE PHYSICIAN ORDERED TREATMENT/CONTACT PHYSICIAN IMMEDIATELY" and "HIGHLY SIGNIFICANT CHANGE IN LUNG FUNCTIONS/OBTAIN EMERGENCY TREATMENT IMMEDIATELY" may be made. In certain cases where the computer is unable to provide a reliable indication/recommendation due to technical difficulties with the test, an indication such as "BECAUSE OF TECHNICAL PROBLEMS RECOMMENDATION UNAVAILABLE/CONTACT YOUR PHYSICIAN/REPEAT TEST" may be provided.

Additionally or alternatively, an automatic connection may be made to the controller computer 420 which may apply decision functionality similar to that used by the user's general purpose computer, but preferably including additional informational resources, such as breathing pattern analysis and lung noise analysis. The controller computer may also make any of the above-listed recommendations to the user. Alternatively or additionally, an automatic connection may be made to the manned center 36 (FIG. 1) wherein a human operator, such as a physician may review all of the personal parameters, analyses thereof and additional available medical information and make appropriate recommendations for action.

As noted above, complete records of all communications between the user and both the controller computer 420 and the manned center are maintained at the controller computer 420 for future reference.

Turning to FIG. 8B, it is seen that for each of a plurality of relevant parameters, such as the forced expirium waveform 418, the Forced Vital Capacity (FVC), the Forced Expiratory Volume during the first second of the forced expirium (FEV1) and the peak flow rate (PF) and the average expiration flow rate during that portion of the expirium at which between 25% and 75% of the air in the lungs has been expelled (FEF 25%–75%), predicted, baseline and current test values are provided. Ratios may be calculated. Additionally or alternatively, the differences between a current test and previous tests and/or predicted values, as from databases 138 and 140 (FIG. 2), for the same patient may be determined and used.

The differences are preferably categorized as to their significance and the number of parameters falling within each category are noted. It is appreciated that various parameters may be given different weighting. All of the relevant parameters are taken into account with their respective weighting and a total, suitably weighted, value is used to determine which indications/recommendations are provided to the user and whether to utilize the analysis of the controller computer 420 and/or to engage the services of the manned center 36 (FIG. 1).

In the specific example shown in FIG. 8B, four categories, each having a different weighting, are defined. Category A includes parameters having a current to baseline (C/B) difference less than 20% and is given a weight of 0. Category B includes parameters having a current to baseline (C/B) difference between 20% and 35% and is given a weight of 2. Category C includes parameters having a C/B difference of between 35% and 50% and is given a weight of 4. Category D includes parameters having a C/B difference exceeding 50% and is given a weight of 9.

It is appreciated that differences in different parameters may be measured in different ways, as most appropriate. In the example of FIG. 8B, however, the differences in the forced expirium waveform 418, the Forced Vital Capacity (FVC), the Forced Expiratory Volume (FEV1) during the first second of the forced expirium and the peak flow rate (PF) and the average expiration flow rate during that portion of the expirium at which between 25% and 75% of the air in the lungs has been expelled (FEF 25%–75%) are all measured as the ratio of current to baseline values.

Thus it is seen in FIG. 8B that no parameter falls within Category A and two parameters, namely FVC and FEV1, fall within Category B. Two parameters, FEF 25%–75% and PF fall within Category C. No parameters fall within Category D. The resulting total weighted score is thus 12.

The relationship between weighted scores and indications/recommendations for the example shown in FIG. 8B, is typically as follows:

| Weighted Score | Indication/Recommendation |
| --- | --- |
| 0–2 | "INSIGNIFICANT CHANGE IN LUNG FUNCTIONS/ NO ACTION REQUIRED" |
| 3–4 | "POSSIBLY SIGNIFICANT CHANGE IN LUNG FUNCTIONS/CONTACT PHYSICIAN/ REPEAT TEST" |
| 5–8 | "SIGNIFICANT CHANGE IN LUNG FUNCTIONS/IMMEDIATELY INITIATE PHYSICIAN ORDERED TREATMENT/CONTACT PHYSICIAN IMMEDIATELY" |
| 9+ | "HIGHLY SIGNIFICANT CHANGE IN LUNG FUNCTIONS/OBTAIN EMERGENCY TREATMENT IMMEDIATELY" |

Accordingly, the recommendation in the example of FIG. 8B is "HIGHLY SIGNIFICANT CHANGE IN LUNG FUNCTIONS/OBTAIN EMERGENCY TREATMENT IMMEDIATELY".

Reference is now made to FIG. 5C, which is a pictorial illustration of part of the medical condition sensing system of FIG. 1 being employed for electrocardiogram testing. FIG. 5C shows three stages in electrocardiogram testing, a first stage, indicated by designation I, at which calibration takes place; a second stage, indicated by designation II, at which a baseline reference is generated and a third stage, indicated by designation III, at which an actual test is conducted. The context of FIG. 5C is typically a situation wherein a person has an interest in determining possible changes in his electrocardiogram, such as following aerobic exercise or when experiencing shortness of breath or chest pains.

In the environment of FIG. 5C, a user interface is provided which preferably includes a 12 lead ECG recorder/transmitter 510, such as a HEARTVIEW R ECG recorder/transmitter commercially available from Aerotel Ltd. of Holon, Israel. The 12 lead ECG recorder/transmitter 510 typically provides an electrical output directly or via a suitable audio coupler to a suitable interface of a general purpose computer 10 (FIG. 1), here designated by reference numeral 514.

A recording and storage facility 40 (FIG. 1), here designated by reference numeral 516, at general purpose computer 514 is operative for recording and storing calibration data and at least one baseline electrocardiogram received by the general purpose computer 514 from 12 lead ECG recorder/transmitter 510.

Prior to generating a baseline electrocardiogram, the 12 lead ECG recorder/transmitter 510 is calibrated, as indicated at I in FIG. 5C. Typically a 1 mV signal generator 518 is employed to apply a 1 mV signal to the interface of the general purpose computer to which the recorder/transmitter 510 is connected. The general purpose computer is typically calibrated such that the amplitude of the 1 mV signal appears as 10 mm in the Y direction. The software contained in the user's general purpose computer automatically carries out this calibration.

Following calibration of the 12 lead ECG recorder/transmitter 510, a baseline electrocardiogram is generated by carrying out a baseline test, as seen at II in FIG. 5C. This baseline test is preferably carried out when the person is in apparent good health and shows no symptoms of stress or distress.

Software 42 (FIG. 1), here designated by reference numeral 519, which is preferably resident in general purpose computer 514, provides appropriate signal processing and comparison of electrocardiogram indications received by the general purpose computer 514 from 12 lead ECG recorder/transmitter 510.

Following establishment of the baseline reference, an actual test is carried out at a subsequent time, as indicated at III in FIG. 5C. The actual test is preferably carried out when the person shows symptoms of stress or distress and may require attention. It is seen that the test results for the actual test, shown at III, differ from the test results for the baseline reference, shown at II.

Software 519 compares the electrocardiogram received during the actual test with the baseline established by at least one earlier test and may apply a threshold to the comparison result. Software 519 typically provides via the general purpose computer 514 an indication of exceedance or non-exceedance of the threshold along with suitable description of the situation which may be accompanied by recommendations for action.

Software 519 typically compares various measured ECG parameters for each lead, such as the heart rate, R-R interval, P-R interval, Q-S-interval, Q-T interval, and the height of the S-T segment as compared with the height of the P-Q segment and the T-P segment. Software 519 may also compare various calculated ECG parameters, such as the following parameters: Q/R ratio for each lead and the overall axes for all leads of the QRS, P and T waves.

A controller computer 16 (FIG. 1), here designated by reference numeral 520, preferably communicates with software 519 for assisting in providing recommendations for action. Where a manned center 36 (FIG. 1) is provided, a human interface or human evaluation of the electrocardiogram may also be provided to the user. To enhance the efficacy of interface between the user and personnel in the manned center 36 (FIG. 1) a video camera 38 (FIG. 1), here designated by reference numeral 522, may be located at the user location to enable personnel in the manned center 36 to view the patient whose electrocardiogram is being taken.

In accordance with another preferred embodiment of the present invention, communication with the manned center may be actuated automatically by the system, normally through the action of the controller computer 520, for example in response to electrocardiogram of a given configuration or the output of a comparison of the currently sensed electrocardiogram with a baseline or with a standard reference which exceeds a threshold indicating a possibly critical condition or possibly improper use of the kit.

Figure 6C:
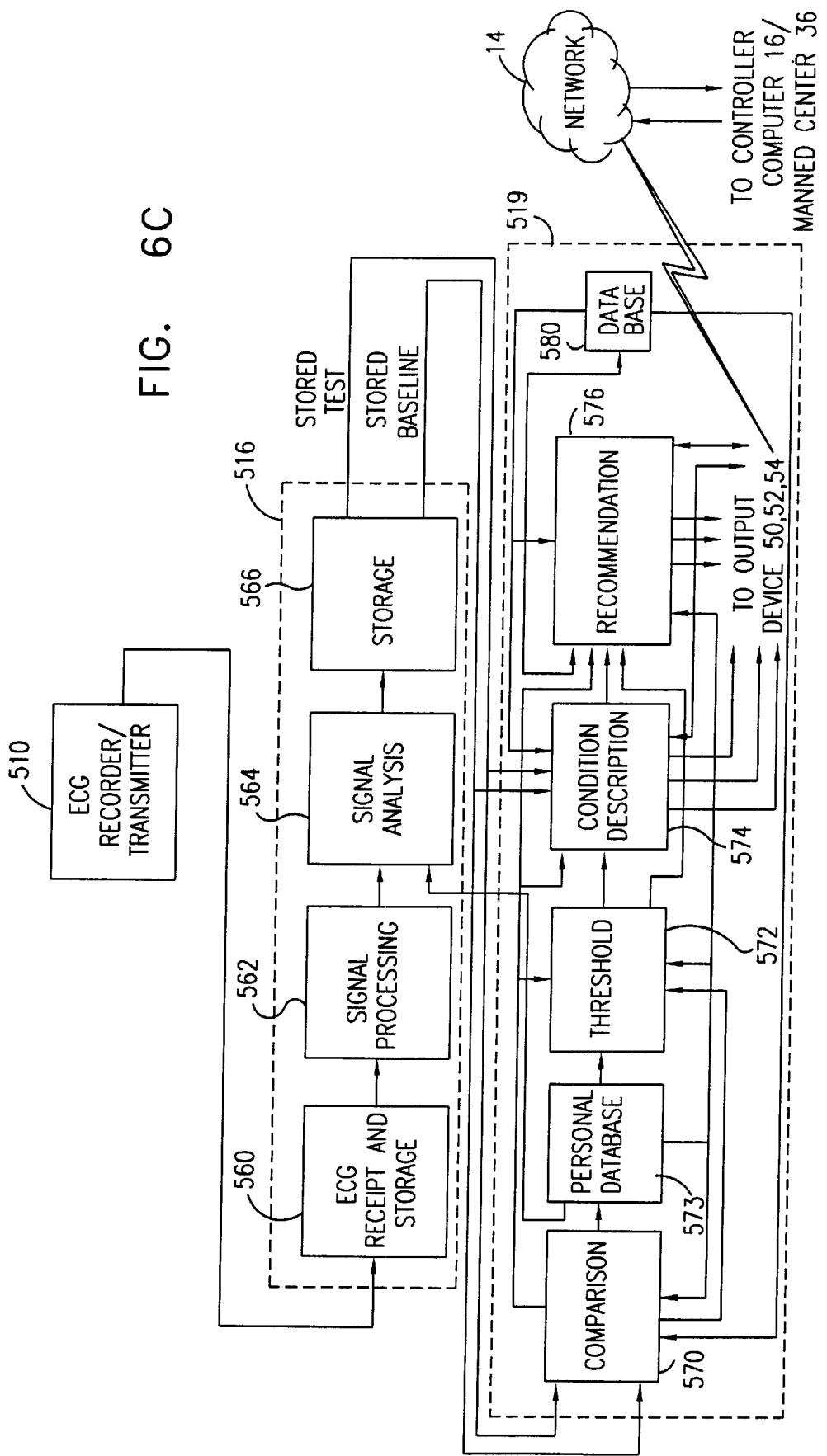
FIG. 6C is a simplified functional block diagram of the system of FIG. 1 having the functionality shown in FIG. 5C.

Reference is now made to FIG. 6C, which is a simplified functional block diagram of the system of FIG. 1 having the functionality of FIG. 5C, namely electrocardiogram testing, typically in an environment wherein a person has an interest in determining possible changes in his electrocardiogram, such as following aerobic exercise or when experiencing shortness of breath or chest pains.

In the environment of FIG. 5C, as illustrated in FIG. 6C, 12 lead ECG recorder/transmitter 510 provides a electrocardiogram output to recording and storage facility 516 (FIG. 5C) of general purpose computer 514 (FIG. 5C). As noted above with reference to FIG. 5C, preferably a baseline is initially established by a test conducted in an environment wherein a person is relaxed. Thereafter, a further test may be conducted when the person experiences stress or distress. In both cases, the resulting signals received from 12 lead ECG recorder/transmitter 510 are processed using the functionality described hereinabove with reference to FIGS. 2, 3 and 4.

In the embodiment of FIG. 6C, preferably the recording and storage facility 516 stores both baseline electrocardiogram data and actual test electrocardiogram data. A electrocardiogram receipt and storage facility 560 receives and stores data received from recorder/transmitter 510. A signal processing facility 562 removes unwanted data artifacts and generally prepares the data for analysis.

A signal analysis functionality 564 preferably performs the following functions on the electrocardiogram data:

Measurement of ECG parameters for each lead, such as the heart rate, Q/R ratio, R-R interval, P-R interval, Q-S interval, Q-T interval, and the height of the S-T segment as compared with the height of the P-Q segment and the T-P segment;

Calculation of various ECG parameters, such as the following parameters: Q/R ratio for each lead and the overall axes for all leads of the QRS, P and T waves.

The outputs of the signal analysis functionality 564 are preferably stored in storage facility 566.

The above-described functionality provided by software 516 is applied initially to a baseline electrocardiogram and thereafter to an actual test electrocardiogram. The stored results for both the baseline signal and for the test signal are supplied to software 519.

Software 519 preferably comprises comparison functionality 130 (FIG. 2), here designated by reference numeral 570, which compares the electrocardiogram analysis data relating to an actual test, stored by recording and storage facility 560 with baseline electrocardiogram analysis data also stored by facility 560 and preferably also with expected values for such electrocardiogram analysis data which may be received from database 140 (FIG. 2) here designated by reference numeral 571.

The comparison functionality 570 preferably provides comparison of measured, predicted and baseline values of various electrocardiogram parameters such as measured ECG parameters for each lead, such as the heart rate, R-R interval, P-R interval, Q-S interval, Q-T interval, and the height of the S-T segment as compared with the height of the P-Q segment and the T-P segment as well as various calculated ECG parameters, such as the following parameters: Q/R ratio for each lead and the overall axes for all leads of the QRS, P and T waves. The predicted values fall within known normal limits for each parameter.

The comparison functionality 570 preferably applies sensed differences therebetween to thresholding functionality 132 (FIG. 2), here designated by reference numeral 572, which may apply a threshold to the comparison result indicating whether the currently sensed electrocardiogram parameters are substantially different from the baseline and/or from the expected values therefor. Threshold functionality may employ data received from a personal database 573, which may also provide data to signal analysis functionality 564 of software 516 for use in normalizing analysis data for given patient parameters.

Outputs of comparison functionality 570 and thresholding functionality 572 are preferably provided to condition description functionality 134 (FIG. 2) here designated by reference numeral 574, which provides a description of the sensed electrocardiogram indications via an output device, such as a display 50, printer 52 and audio transducer 54 (FIG. 1).

Outputs provided by comparison functionality 570, thresholding functionality 572 and condition description functionality 574 may be further processed by recommendation functionality 136 (FIG. 2) here designated by reference numeral 576, which may provide indications/recommendations to the user via any one or more of display 50, printer 52 or transducer 54.

Preferably, both condition description functionality 574 and recommendation functionality 576 also receive reference data from database 571.

Preferably, both condition description functionality 574 and recommendation functionality 576 receive reference data from a database 140, here designated by reference numeral 580, which stores acceptable ranges of outputs of comparison functionality 570, normalized for age and possibly other characteristics. Database 580 is preferably employed to enable condition description functionality 574 and recommendation functionality 576 to take into account the variation in acceptable changes in various personal parameters due to variations in age and possibly other characteristics.

Communication with a remote computer, such as a controller computer 16 (FIG. 1) may be initiated automatically by the general purpose computer 514 via the network 14, for example in response to the output of comparison functionality 570, threshold functionality 572, condition description functionality 574 or recommendation functionality 576, indicating, for example a possibly acute cardiac condition or a suspected misuse or malfunction of the kit.

Thus, when one or more sensed electrocardiogram parameters or the comparison output lies beyond a certain threshold which may indicate either an emergency situation or a situation requiring controller intervention, communication is established immediately between the user's general purpose computer 514 and the controller computer 16 (FIG. 1) via the network 14 (FIG. 1). Communication via the network 14 with the controller computer 16 may also be initiated by a user, at the user's initiative.

Where a manned center 36 (FIG. 1) is provided, a human interface or human evaluation may also be provided to the user. It is thus possible for medical personnel in the manned center 36 to directly view the patient while viewing the electrocardiogram directly and speaking with the user.

Reference is now made to FIG. 7C, which is a simplified flowchart illustrating the operation of the system of FIG. 1 in the operative environment of FIGS. 5C and 6C.

Initially the user accesses a system web site and carries out the initial communications and actions described hereinabove with respect to FIG. 4, which include the acquisition of a electrocardiogram test kit including 12 lead ECG recorder/transmitter 510 and 1 mV generator 518 for calibration (FIG. 5C) and download of operating baseline establishment software to the user's general purpose computer 514 (FIG. 5C) from the controller computer 520 (FIG. 5C) or otherwise.

The user registers with the user records database 202 of the controller computer (FIG. 3). As noted above, the user records database 202 stores personal details of each patient for which the electrocardiogram kit is to be used as well as general medical information regarding each such patient and results of tests conducted on that patient, using the electrocardiogram sensing kit, to the extent that such results are transmitted to the controller computer. Preferably, the information entered by the user into the user records database 202 of the controller computer 520 such as personal details and general medical information as well as results of the tests conducted on the patient, which are also stored in the personal database 573 of the user's general purpose computer 514.

Calibration of the recorder/transmitter 410 is preferably carried out by using 1 mV generator 518.

When the user is ready to perform a baseline electrocardiogram test, following current use registration and calibration of the recorder/transmitter 510, a baseline test is carried out as seen at II in FIG. 5C. This baseline test is preferably carried out when the person is relaxed and in apparent good health.

Software 519 provides appropriate signal processing and comparison of electrocardiogram indications received by the general purpose computer 514 from 12 lead ECG recorder/transmitter 510. Software 519 preferably provides the following parameters:

Measured ECG parameters for each lead, such as the heart rate, R-R interval, P-R interval, Q-S interval, Q-T interval, and the height of the S-T segment as compared with the height of the P-Q segment and the T-P segment;

Calculated ECG parameters, such as the following parameters: Q/R ratio for each lead and the overall axes for all leads of the QRS, P and T waves.

It is appreciated that should one or more baseline values differ from expected values to a medically significant extent, such as that described hereinbelow with reference to FIG. 8C, appropriate indications/recommendations may be provided immediately to the user and the controller computer and the manned center may be employed as appropriate.

At least some of the foregoing parameters as well as possibly other parameters are employed by operating software installed at the user's general purpose computer 514. Some or all of the parameters are preferably stored both at the user's general purpose computer 514 and in user records database 202 at the controller computer 520.

At a later time, when a test is carried out on the same patient who may be experiencing stress or distress, preferably all of the above listed parameters are measured and analyses are considered. Some of the above parameters are preferably normalized for the age of the patient.

The general purpose computer 514 preferably determines the differences between the baseline values and the current test values for the various parameters and analysis results and preferably indicates both the absolute difference and the percentage difference.

Based on the calculated differences between the baseline and the current test results, and using the information contained in databases 574 and 580, the operating software installed at the user's general purpose computer 514 is preferably operative to provide a condition description and recommendations to the user via the user's general purpose computer. The user's general purpose computer 514 may also employ inputs from the controller computer 520 in providing the condition description and recommendations to the user.

Depending on the comparison results and the recommendations, the user's computer may provide to the controller computer 520 the comparison results and possibly some or all of the test and baseline information.

The controller computer may analyze the comparison results and possibly some or all of the test and baseline information and provide results of the analysis to the user via the user's general purpose computer.

Preferably, the controller computer 520 makes a determination as to whether to contact a manned center 36. The user may make an independent determination whether to contact the manned center 36. A user's decision to utilize the services of the manned center which is not supported by the decision of the controller computer 520 may incur an additional charge, depending on the financial arrangements with the user.

Preferably, the condition description and recommendations are provided in accordance with a decision table, an example of which is provided in FIG. 8C.

The decision table of FIG. 8C is merely exemplary and illustrates the application of typical decision and recommendation functionality to a typical patient, a 40 year male.

As noted above, based on the application of the decision and indication/recommendation functionality, an indication/recommendation such as "INSIGNIFICANT CHANGE IN ELECTROCARDIOGRAM/NO ACTION REQUIRED", "POSSIBLY SIGNIFICANT CHANGE IN ELECTROCARDIOGRAM/CONTACT PHYSICIAN/REPEAT TEST", and "SIGNIFICANT CHANGE IN ELECTROCARDIOGRAM/OBTAIN EMERGENCY TREATMENT IMMEDIATELY" may be made. In certain cases where the computer is unable to provide a reliable indication/recommendation due to technical difficulties with the test, an indication such as "BECAUSE OF TECHNICAL PROBLEMS RECOMMENDATION UNAVAILABLE/CONTACT YOUR PHYSICIAN/REPEAT TEST" may be provided.

Additionally or alternatively, an automatic connection may be made to the controller computer 420 which may apply decision functionality similar to that used by the user's general purpose computer, but preferably including additional informational resources, such as pattern analysis, measuring P-P intervals and comparison thereof to R-R intervals. The controller computer may also make any of the above-listed recommendations to the user. Alternatively or additionally, an automatic connection may be made to the manned center 36 (FIG. 1) wherein a human operator, such as a physician, may review all of the personal parameters, analyses thereof and additional available medical information and make appropriate recommendations for action.

As noted above, complete records of all communications between the user and both the controller computer 520 and the manned center are maintained at the controller computer 520 for future reference.

Turning to FIG. 8C, it is seen that for each of a plurality of relevant parameters, such as heart rate, Q/R ratio, P-R interval, Q-S interval, QRS axis, T axis, S-T segment height, normal limits as well as baseline and current test values are provided. Ratios may be calculated. Additionally or alternatively, the differences between a current test and previbus tests and/or normal limits, as from databases 573 and 580, for the same patient may be determined and used.

In this case independent weighting is preferably given both to the difference between current test values and baseline values and to the relationship between current test values and normal limits for such values. The differences and the relationships are preferably categorized as to their significance and the number of parameters falling within each category are noted. It is appreciated that various parameters may be given different weighting. All of the relevant parameters are taken into account with their respective weighting and a total, suitably weighted, value is used to determine which indications/recommendations are provided to the user and whether to utilize the analysis of the controller computer 520 and/or to engage the services of the manned center 36 (FIG. 1).

In the specific example shown in FIG. 8C, four categories, each having a different weighting, are defined. Category A includes parameters having a ratio of current to baseline difference to baseline (D/B) than 20% and is given a weight of 0. Category B includes parameters having a ratio of current to baseline difference to baseline (D/B) between 20% and 30% and is given a weight of 2. Category C includes parameters having a ratio of current to baseline difference to baseline (D/B) greater than 30% and is given a weight of 4. Category D includes parameters which exceed normal limits, preferably according to physician's decision, and is giving a weight of 6.

It is appreciated that differences in different parameters may be measured in different ways, as most appropriate. In the example of FIG. 8C, however, differences in the heart rate, the P-R interval, the Q-S interval, the QRS Axis, The T Axis and the S-T segment height are all measured as the ratio of current to baseline values.

Thus it is seen in FIG. 8C that the Q-S interval falls within Category A and the heart rate and QRS Axis fall within Category B. Two parameters, the P-R interval and the T Axis fall within Category C. Three parameters, the heart rate, the Q-S interval, and the S-T segment height are outside their normal limits and thus fall within Category D. The resulting total weighted score is thus 30.

The relationship between weighted scores and indications/recommendations for the example shown in FIG. 8C, is typically as follows:

| Weighted Score | Indication/Recommendation |
| --- | --- |
| 0–2 | "INSIGNIFICANT CHANGE IN ELECTROCARDIOGRAM/NO ACTION REQUIRED" |
| 3–8 | "POSSIBLY SIGNIFICANT CHANGE IN ELECTROCARDIOGRAM/CONTACT PHYSICIAN/ REPEAT TEST" |
| 9+ | "SIGNIFICANT CHANGE IN ELECTROCARDIOGRAM/ OBTAIN EMERGENCY TREATMENT IMMEDIATELY" |

Accordingly, the recommendation in the example of FIG. 8C is "SIGNIFICANT CHANGE IN ELECTROCARDIOGRAM/OBTAIN EMERGENCY TREATMENT IMMEDIATELY".

In this example, if the total exceeds typically 16, the manned center 36 is immediately invoked.

Figure 5D:
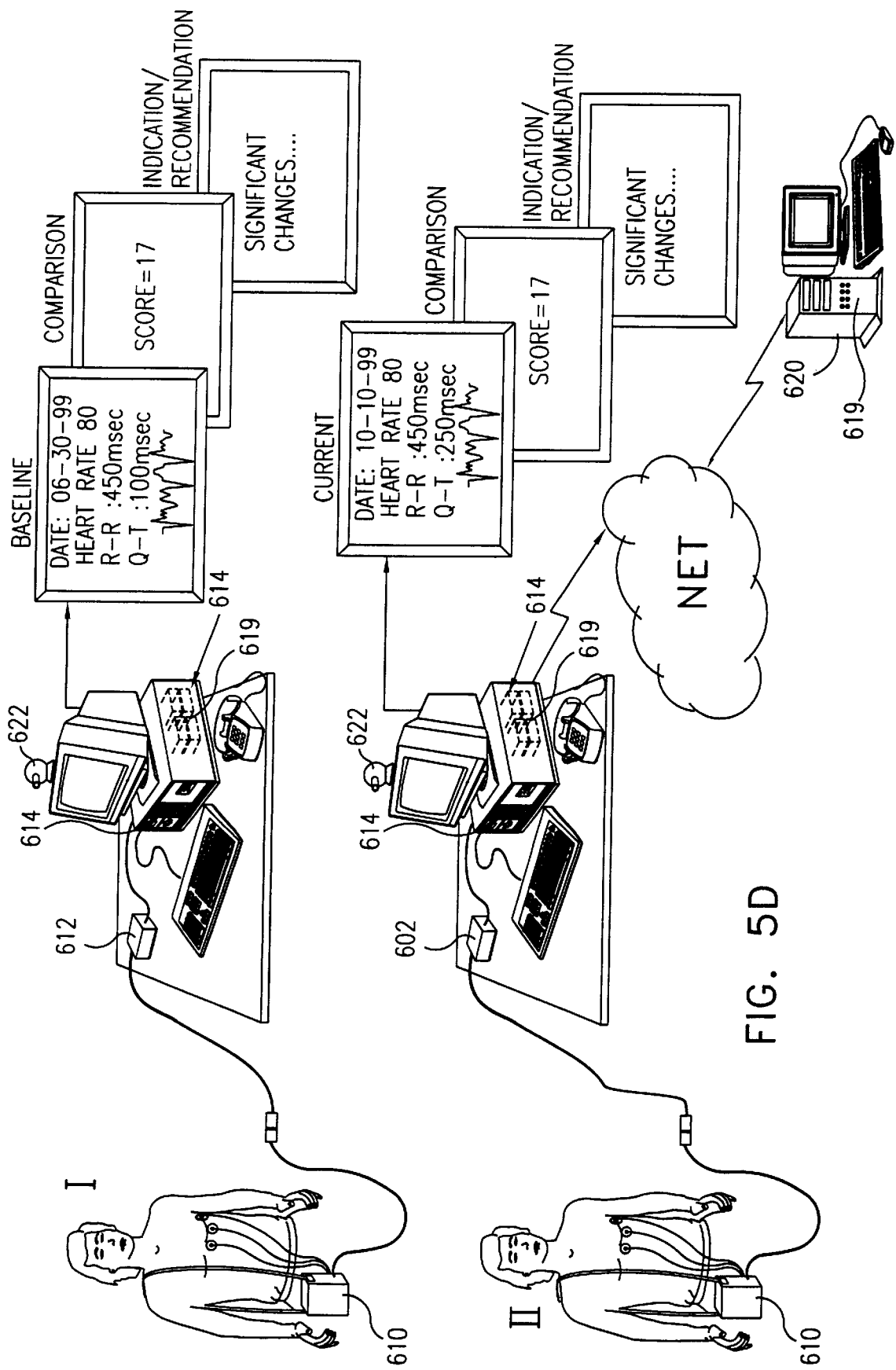
FIG. 5D is a pictorial illustration of part of the medical condition sensing system of FIG. 1 being employed for cardiac rhythm monitoring.

Reference is now made to FIG. 5D, which is a pictorial illustration of part of the medical condition sensing system of FIG. 1 being employed for prolonged electrocardiogram testing, otherwise known as Holter monitoring. FIG. 5D shows a single stage in prolonged electrocardiogram testing. The context of FIG. 5D is typically a situation wherein a person wishes to monitor his heart rate and to determine whether and to what extent there exists disrhythmia.

In the environment of FIG. 5D, a user interface 612 is provided which preferably includes a 3–4 lead ECG recorder/transmitter 610, such as a HEARTVIEW R ECG recorder/transmitter commercially available from Aerotel Ltd. of Holon, Israel. The ECG recorder/transmitter 610 typically provides an electrical output directly or via a suitable audio coupler or other interface 612 to a suitable interface of a general purpose computer 10 (FIG. 1), here designated by reference numeral 614.

A recording and storage facility 40 (FIG. 1), here designated by reference numeral 616, at general purpose computer 614 is operative for recording and storing data received by the general purpose computer 614 from ECG recorder/transmitter 610. An actual test is preferably carried out whenever appropriate.

Software 619, preferably resident in general purpose computer 614, compares electrocardiogram derived data received during the actual test with electrocardiogram derived data produced during at least one earlier test and may apply a threshold to the comparison result. Software 619 typically provides via the general purpose computer 614 an indication of exceedance or nonexceedance of the threshold along with suitable description of the situation which may be accompanied by recommendations for action.

Software 619 also includes a Holter monitoring software (24 hrs. ECG recording and monitoring) which is commercially available from many sources, such as Schiller AG, CH-6340 Baar, Switzerland.

Software 619 also typically compares various measured ECG parameters for each lead, such as the heart rate, R-R interval, P-P interval, P-R interval and Q-S interval. Software 619 may also compare various calculated ECG parameters related to disrhythmia including frequency of premature beats (PMB).

A controller computer 16 (FIG. 1), here designated by reference numeral 620, preferably communicates with software 619 for assisting in providing recommendations for action. Where a manned center 36 (FIG. 1) is provided, a human interface or human evaluation of the electrocardiogram may also be provided to the user. To enhance the efficacy of interface between a user and personnel in the manned center 36 (FIG. 1) a video camera 38 (FIG. 1), here designated by reference numeral 622, may be located at the user location to enable personnel in the manned center 36 to view the patient whose electrocardiogram is being taken.

In accordance with another preferred embodiment of the present invention, communication with the manned center may be actuated automatically by the system, normally through the action of the controller computer 620, for example in response to electrocardiogram derived data or the output of a comparison of the currently sensed electrocardiogram derived data with corresponding data from a previous electrocardiogram or with a standard reference which exceeds a threshold indicating a possibly critical condition or possibly improper use of the kit.

Figure 6D:
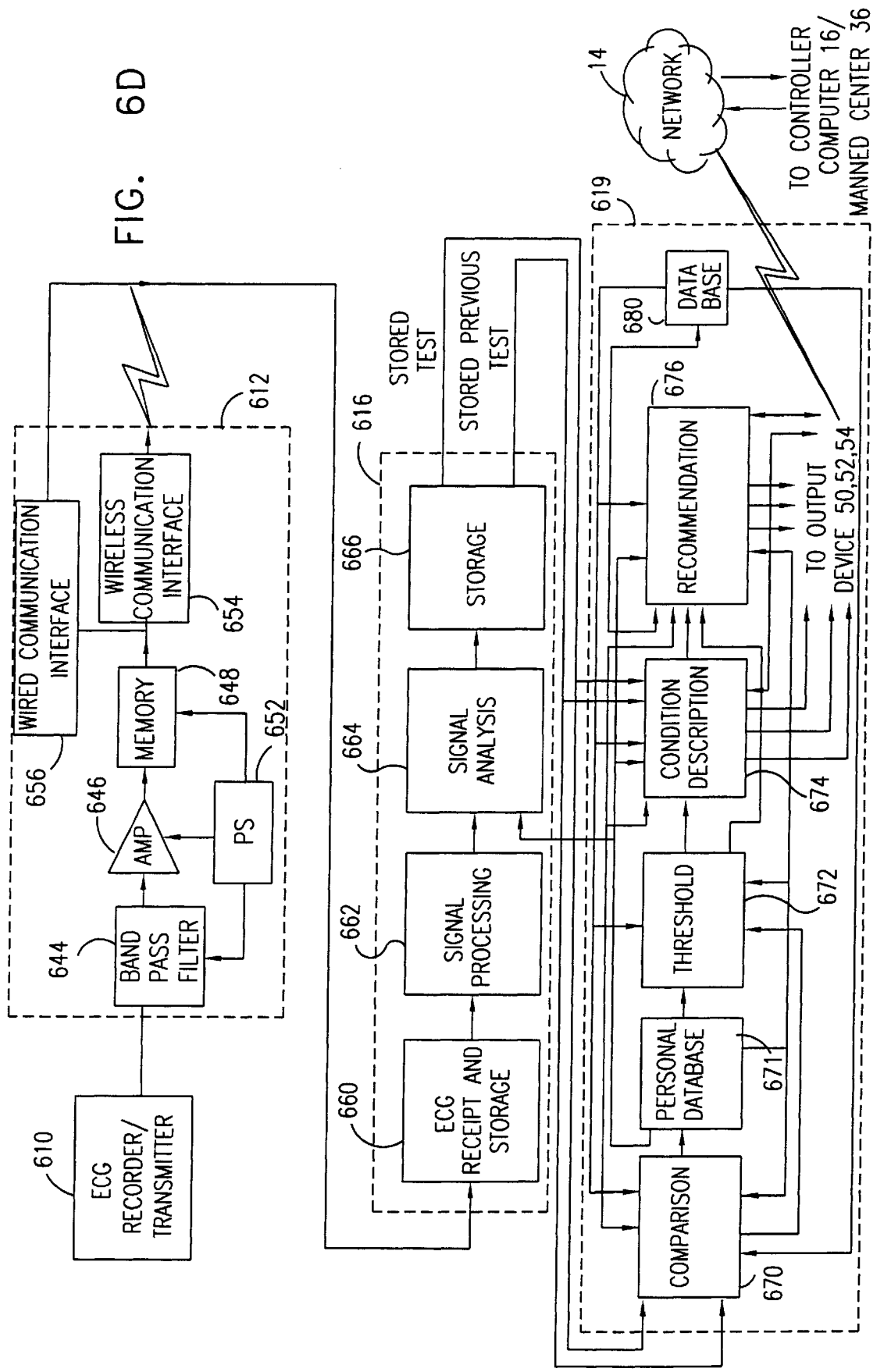
FIG. 6D is a simplified functional block diagram of the system of FIG. 1 having the functionality shown in FIG. 5D.

Reference is now made to FIG. 6D, which is a simplified functional block diagram of the system of FIG. 1 having the functionality of FIG. 5D, namely prolonged electrocardiogram testing, typically in an environment wherein a person wishes to monitor his heart rate and to determine whether and to what extent there exists disrhythmia.

In the environment of FIG. 5D, as illustrated in FIG. 6D, ECG recorder/transmitter 610 provides a electrocardiogram output via interface 612 to recording and storage facility 616 (FIG. 5D) of general purpose computer 614 (FIG. 5D). As noted above with reference to FIG. 5D, preferably multiple tests are conducted at different times. The resulting signals received from ECG recorder/transmitter 610 are processed using the functionality described hereinabove with reference to FIGS. 2, 3 and 4.

In the embodiment of FIG. 6D, interface circuitry 612 is preferably portable so as to be carried by the patient and preferably employs a band pass filter 644 which filters out spurious and extraneous noise outside a desired band, centered on about 1900 Hz. The output of filter 644 is amplified by an amplifier 646 and preferably supplied to a memory 648. A portable power supply 652 preferably supplies power to the foregoing components as well as to a wireless communication interface 654 and/or a wired communication interface 656 which output to general purpose computer 614 (FIG. 5D).

In the embodiment of FIG. 6D, preferably the recording and storage facility 616 stores both previously derived electrocardiogram data and current test electrocardiogram data. A electrocardiogram receipt and storage facility 660 receives and stores data received from recorder/transmitter 610. A signal processing facility 662 removes unwanted data artifacts and generally prepares the data for analysis.

A signal analysis functionality 664 preferably performs the following functions on the electrocardiogram data:

Measurement of ECG parameters for each lead, such as the heart rate, Q/R ratio, R-R interval, P-P interval, P-R interval and Q-S interval.

Calculation of various ECG parameters relevant to disrhythmia.

The outputs of the signal analysis functionality 664 are preferably stored in storage facility 666.

The above-described functionality provided by software 616 is applied to an earlier electrocardiogram and thereafter to an later test electrocardiogram. The stored results for both of the test signals are supplied to software 619.

Software 619 preferably comprises comparison functionality 130 (FIG. 2), here designated by reference numeral 670, which compares the electrocardiogram analysis data relating to an actual test, stored by recording and storage facility 660 with earlier derived electrocardiogram analysis data also stored by facility 660 and preferably also with expected values for such electrocardiogram analysis data which may be received from database 138 (FIG. 2) here designated by reference numeral 671.

The comparison functionality 670 preferably provides comparison of measured and predicted values of various electrocardiogram parameters such as measured ECG parameters for each lead, typically including the heart rate, the R-R interval, P-P interval, P-R interval and Q-S interval as well as various relevant calculated ECG parameters The comparison functionality 670 preferably applies sensed differences therebetween to thresholding functionality 132 which may apply a threshold to the comparison result indicating whether the currently sensed electrocardiogram parameters are substantially different from the previous or otherwise expected values therefor. Threshold functionality may employ data received from a personal database 671, which may also provide data to signal analysis functionality 664 of software 616 for use in normalizing analysis data for given patient parameters.

Outputs of comparison functionality 670 and thresholding functionality 672 are preferably provided to condition description functionality 134 (FIG. 2) here designated by reference numeral 674, which provides a description of the sensed electrocardiogram indications via an output device, such as a display 50, printer 52 and audio transducer 54 (FIG. 1).

Outputs provided by comparison functionality 670, thresholding functionality 672 and condition description functionality 674 may be further processed by recommendation functionality 136 (FIG. 2) here designated by reference numeral 676, which may provide indications/recommendations to the user via any one or more of display 50, printer 52 or transducer 54.

Preferably, both condition description functionality 674 and recommendation functionality 676 also receive reference data from database 671.

Preferably, both condition description functionality 674 and recommendation functionality 676 receive reference data from a database 140, here designated by reference numeral 680, which stores acceptable ranges of outputs of comparison functionality 670, normalized for age and possibly other characteristics. Database 680 is preferably employed to enable condition description functionality 674 and recommendation functionality 676 to take into account the variation in acceptable changes in various personal parameters due to variations in age and possibly other characteristics.

Communication with a remote computer, such as a controller computer 16 (FIG. 1) may be initiated automatically by the general purpose computer 614 via the network 14, for example in response to the output of comparison functionality 670, threshold functionality 672, condition description functionality 674 or recommendation functionality 676, indicating, for example a possibly acute cardiac condition or a suspected misuse or malfunction of the kit.

Thus, when one or more sensed electrocardiogram parameters or the comparison output lies beyond a certain threshold which may indicate either an emergency situation or a situation requiring controller intervention, communication is established immediately between the user's general purpose computer 614 and the controller computer 620 via the network 14 (FIG. 1). Communication via the network 14 with the controller computer 620 may also be initiated by a user, at the user's initiative.

Where a manned center 36 (FIG. 1) is provided, a human interface or human evaluation may also be provided to the user. It may be possible for medical personnel in the manned center 36 to directly view the patient while viewing the electrocardiogram directly and speaking with the user.

In accordance with a preferred embodiment of the present invention, the normal limits used in the threshold and condition description functionality may be established by medical personnel in the manned center 36 in accordance with the personal characteristics of each given patient.

Reference is now made to FIG. 7D, which is a simplified flowchart illustrating the operation of the system of FIG. 1 in the operative environment of FIGS. 5D and 6D.

Initially the user accesses a system web site and carries out the initial communications and actions described hereinabove with respect to FIG. 4, which include the acquisition of a electrocardiogram test kit including a 3–4 lead ECG recorder/transmitter 610 and download of operating software to the user's general purpose computer 614 (FIG. 5D) from the controller computer 620 (FIG. 5D) or otherwise.

The user registers with the user records database 202 of the controller computer (FIG. 3). As noted above, the user records database 202 stores personal details of each patient for which the electrocardiogram kit is to be used as well as general medical information regarding each such patient and results of tests conducted on that patient, using the electrocardiogram sensing kit, to the extent that such results are transmitted to the controller computer 620. Preferably, the information entered by the user into the user records database 202 of the controller computer 620 as well as personal details and general medical information such as results of the tests conducted on the patient, are stored in the personal database 671 of the user's general purpose computer 614.

When the user is ready to perform an electrocardiogram test, following current use registration and calibration of the recorder/transmitter 610, a test is carried out as seen in FIG. 5D.

Software 619 provides appropriate signal processing and comparison of electrocardiogram indications received by the general purpose computer 614 from ECG recorder/transmitter 610. Software 619 preferably provides the following parameters:

Measured ECG parameters for each lead, such as the heart rate, R-R interval, P-P interval, P-R interval and Q-S interval.

Calculated ECG parameters which are relevant to disrhythmia.

It is appreciated that should one or more values differ from expected values to a medically significant extent, such as that described hereinbelow with reference to FIG. 8D, appropriate indications/recommendations may be provided immediately to the user and the controller computer and the manned center may be employed as appropriate.

At least some of the foregoing parameters as well as possibly other parameters are employed by operating software installed at the user's general purpose computer 614. Some or all of the parameters are preferably stored both at the user's general purpose computer 614 and in user records database 202 at the controller computer 620.

At a later time, when a test is carried out on the same patient all of the above listed parameters are analyzed and considered. Some of the above parameters are preferably normalized for the age of the patient.

The general purpose computer 614 preferably determines the differences between the earlier test values and the current test values for the various parameters and analysis results and preferably indicates both the absolute difference and the percentage difference.

Based on the calculated differences between the earlier and the current test results, and using the information contained in databases 671 and 680, the operating software installed at the user's general purpose computer 614 is preferably operative to provide a condition description and recommendations to the user via the user's general purpose computer. The user's general purpose computer 614 may also employ inputs from the controller computer 620 in providing the condition description and recommendations to the user.

Depending on the comparison results and the recommendations, the user's computer may provide to the controller computer 620 the comparison results and possibly some or all of the test information.

The controller computer may analyze the comparison results and possibly some or all of the test information and provide results of the analysis to the user via the user's general purpose computer.

Preferably, the controller computer 620 makes a determination as to whether to contact a manned center 36. The user may make an independent determination whether to contact the manned center 36. A user's decision to utilize the services of the manned center which is not supported by the decision of the controller computer 620 may incur an additional charge, depending on the financial arrangements with the user.

Preferably, the condition description and recommendations are provided in accordance with a decision table, an example of which is provided in FIG. 8D.

The decision table of FIG. 8D is merely exemplary and illustrates the application of typical decision and recommendation functionality to a typical patient, a 40 year male.

As noted above, based on the application of the decision and indication/recommendation functionality, an indication/recommendation such as "INSIGNIFICANT CHANGE IN ELECTROCARDIOGRAM/NO ACTION REQUIRED", "POSSIBLY SIGNIFICANT CHANGE IN ELECTROCARDIOGRAM I ELECTROCARDIOGRAM DATA BEING TRANSFERRED TO CONTROLLER COMPUTER AND/OR MANNED CENTER FOR EVALUATION" and "SIGNIFICANT CHANGE IN ELECTROCARDIOGRAM/ELECTROCARDIOGRAM DATA BEING TRANSFERRED TO CONTROLLER COMPUTER AND/OR MANNED CENTER FOR EVALUATION/OBTAIN EMERGENCY TREATMENT IMMEDIATELY" may be made. In certain cases where the computer is unable to provide a reliable indication/recommendation due to technical difficulties with the test, an indication such as "BECAUSE OF TECHNICAL PROBLEMS RECOMMENDATION UNAVAILABLE/CONTACT YOUR PHYSICIAN/REPEAT TEST" may be provided.

Additionally or alternatively, an automatic connection may be made to the controller computer 620 which may apply decision functionality similar to that used by the user's general purpose computer, but preferably including additional informational resources, such as pattern analysis, measuring P-P intervals and comparison thereof to R-R intervals. The controller computer may also make any of the above-listed recommendations to the user. Alternatively or additionally, an automatic connection may be made to the manned center 36 (FIG. 1) wherein a human operator, such as a physician, may review all of the personal parameters, analyses thereof and additional available medical information and make appropriate recommendations for action.

As noted above, complete records of all communications between the user and both the controller computer 620 and the manned center are maintained at the controller computer 620 for future reference.

Turning to FIG. 5D, it is seen that for each of a plurality of relevant parameters, such as heart rate, R-R interval, Q/R ratio, P-P interval, P-R interval and Q-S interval normal limits as well as past and current test values are provided. Ratios may be calculated. Additionally or alternatively, the differences between a current test and previous tests and/or normal limits, as from databases 671 and 680, for the same patient may be determined and used. Software 619 (FIG. 5D) also includes a Holter monitoring software (24 hrs. ECG recording and monitoring) which analyses various parameters concerning disrhythmia such as concerning frequency of premature beats (PMB).

In this case independent weighting is preferably given both to the difference between current test values and baseline values and to the relationship between current test values and normal limits for such values. The differences and the relationships are preferably categorized as to their significance and the number of parameters falling within each category are noted. It is appreciated that various parameters may be given different weighting. All of the relevant parameters are taken into account with their respective weighting and a total, suitably weighted, value is used to determine which indications/recommendations are provided to the user and whether to utilize the analysis of the controller computer 620 and/or to engage the services of the manned center 36 (FIG. 1).

In the specific example shown in FIG. 8D, four categories, each having a different weighting, are defined. Category A includes parameters typically having the ratio of the difference of current and baseline to the baseline measurements (D/B) of less than 20% and/or no premature beat (PMB), and is given a weight of 0. Category B includes parameters typically having a ratio of the difference of current and baseline to the baseline measurements (D/B) between 20% to 30% and/or up to 1 premature beat per minute (PMB) and is given a weight of 4. Category C includes parameters typically having the ratio of the difference of current and baseline to the baseline measurements (D/B) of more than 30% and/or more than 1 premature beat per minute (PMB) and is given a weight of 9. Category D includes situations wherein any of the parameters exceed normal limits or frequency of premature beats preferably according to physician's decision, and is given a weight of 4.

It is appreciated that in this example, an important criterion is the number of premature heart beats that occur in a unit of time.

Thus it is seen in FIG. 8D that the Heart Rate falls within Category A and the P-P interval and P-R the interval fall within Category B. The Q-T interval falls within Category D. No parameters fall within Category C. The resulting total weighted score is thus 17.

The relationship between weighted scores and indications/recommendations for the example shown in FIG. 8D, is typically as follows:

| Weighted Score | Indication/Recommendation |
|---|---|
| 0–2 | "INSIGNIFICANT CHANGE IN ELECTROCARDIOGRAM/NO ACTION REQUIRED" |
| 3–8 | "POSSIBLY SIGNIFICANT CHANGE IN ELECTROCARDIOGRAM/ ELECTROCARDIOGRAM DATA BEING TRANSFERRED TO CONTROLLER COMPUTER AND/OR MANNED CENTER FOR EVALUATION" |
| 9+ | "SIGNIFICANT CHANGE IN ELECTROCARDIOGRAM/ ELECTROCARDIOGRAM DATA BEING TRANSFERRED TO CONTROLLER COMPUTER AND/OR MANNED CENTER FOR EVALUATION/ OBTAIN EMERGENCY TREATMENT IMMEDIATELY" |

Accordingly, the recommendation in the example of FIG. 8D is "SIGNIFICANT CHANGE IN ELECTROCARDIOGRAM/ELECTROCARDIOGRAM DATA BEING TRANSFERRED TO CONTROLLER COMPUTER AND/OR MANNED CENTER FOR EVALUATION/OBTAIN EMERGENCY TREATMENT IMMEDIATELY".

In this example, if the total exceeds typically 17, the manned center 36 is immediately invoked.

Figure 5E:
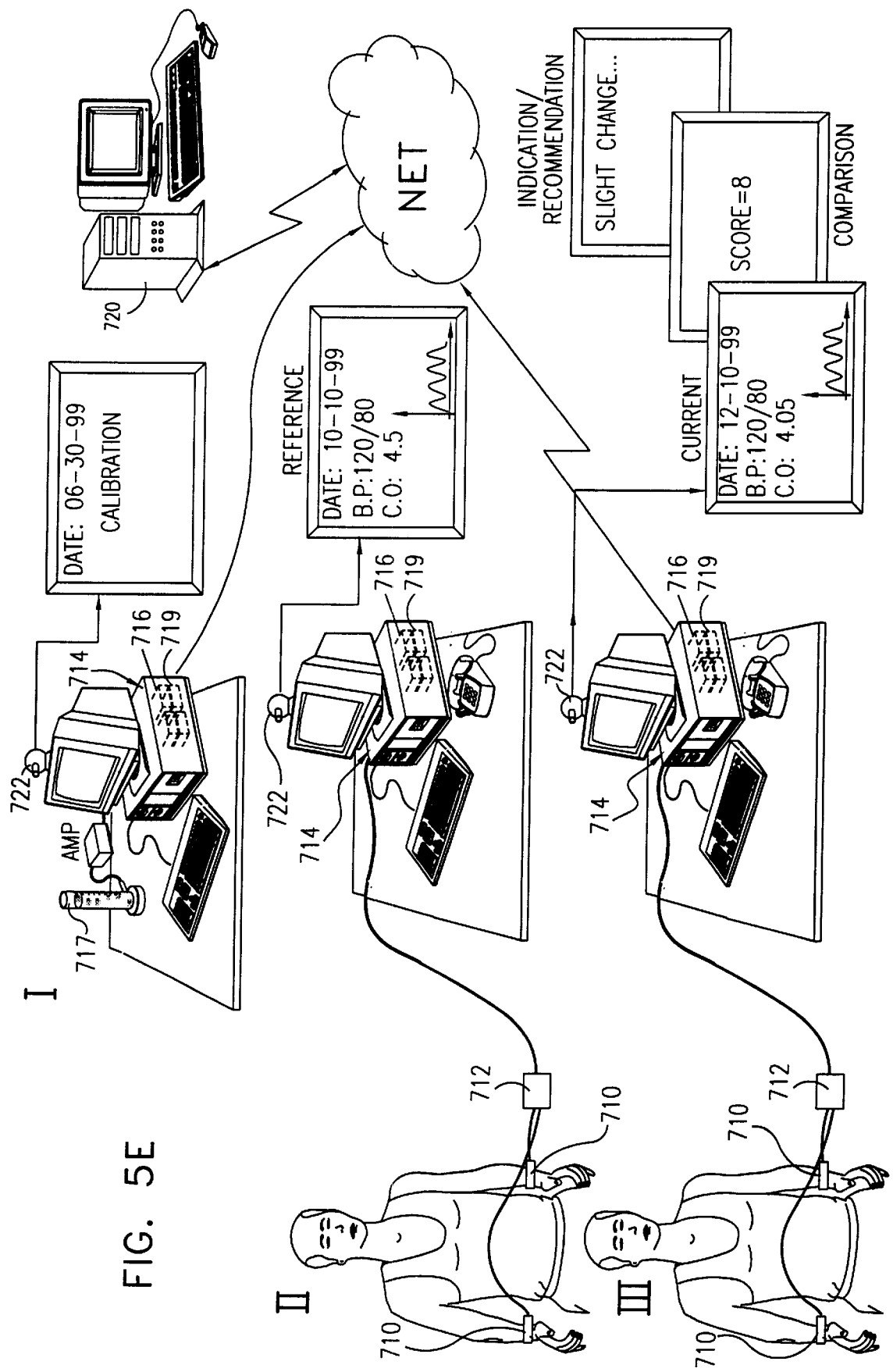
FIG. 5E is a pictorial illustration of part of the medical condition sensing system of FIG. 1 being employed for cardiac output condition sensing.

Reference is now made to FIG. 5E, which is a pictorial illustration of part of the medical condition sensing system of FIG. 1 being employed for cardiac output measurement. FIG. 5E shows three stages in cardiac output measurement, a first stage, indicated by designation I, at which calibration takes place; an optional second stage, indicated by designation II, at which a baseline reference is generated and a third stage, indicated by designation III, at which an actual test is conducted. The context of FIG. 5E is typically a situation wherein a person has a heart condition and wishes to monitor any changes in his cardiac output.

In the environment of FIG. 5E, a user interface is provided which preferably includes a pair of wrist sensors 710, such as optical sensors commercially available from Triphase Medical Ltd. of Herzlia, Israel. The wrist sensors 710 typically provides an electrical output typically via interface circuitry 712 to a suitable interface of a general purpose computer 10 (FIG. 1), here designated by reference numeral 714. Alternatively sensors 710 may be sensors which receive biometric inputs from locations other than the wrist.

A recording and storage facility 40 (FIG. 1), here designated by reference numeral 716, at general purpose computer 714 is operative for recording and storing calibration data and at least one baseline plot of cardiac output received by the general purpose computer 714 from wrist sensors 710.

Prior to generating a baseline plot of cardiac output, the wrist sensors 710 are calibrated, as indicated at I in FIG. 5E. A container 717, typically containing a column of water of a known height, typically 40 cm., is employed to calibrate software contained in the user's general purpose computer 714. The altitude at which the test takes place is normally not considered, up to altitudes of 1500 meters. Alternatively or additionally, calibration may be provided without the use of a column of water, by means of sensing biometric inputs. Such calibration functionality may be incorporated in either or both of sensors 710 and interface circuitry 712.

Following calibration of the output of the wrist sensors. 710, a baseline plot may be generated by carrying out a baseline test, as seen at II in FIG. 5E. This baseline test is preferably carried out when the person shows no symptoms of cardiac distress. The baseline result may include measured blood oxygen saturation and calculated blood pressure and cardiac output volume. Preferably both the baseline test and all subsequent tests are carried out under identical conditions of cardiac stress. Most preferably, all tests are carried out when the subject is in a state of complete rest following at least 10 minutes of no activity.

Software 42 (FIG. 1), here designated by reference numeral 719, which is preferably resident in general purpose computer 714, provides appropriate signal processing and comparison of cardiac output indications received by the general purpose computer 714 from wrist sensors 710. Software 719 preferably provides an indication of calculated blood pressure and cardiac output volume.

Following establishment of the baseline reference, an actual test is carried out at a subsequent time, as indicated at III in FIG. 5E. The actual test is preferably carried out when the person senses that his cardiac output may have changed. It is seen that the test results for the actual test, shown at III, differ from the test results for the baseline reference, shown at II.

Software 719 compares the cardiac output received during the actual test with the baseline established by at least one earlier test and may apply a threshold to the comparison result. Software 719 typically provides, via the general purpose computer 714, an indication of exceedance or non-exceedance of the threshold along with a suitable description of the situation which may be accompanied by recommendations for action.

Software 719 typically compares calculated blood pressure and cardiac output volume.

A controller computer 16 (FIG. 1), here designated by reference numeral 720, preferably communicates with software 719 for assisting in providing recommendations for action. Where a manned center 36 (FIG. 1) is provided, a human interface or human evaluation of the cardiac output may also be provided to the user. To enhance the efficacy of interface between the user and personnel in the manned center 36 (FIG. 1) a video camera 38 (FIG. 1), here designated by reference numeral 722, may be located at the user location to enable personnel in the manned center 36 to view the patient who may be experiencing cardiac distress.

In accordance with another preferred embodiment of the present invention, communication with the manned center may be actuated automatically by the system, normally through the action of the controller computer 720, for example in response to cardiac output of a certain type or the output of a comparison of the currently sensed cardiac output with a baseline or with a standard reference which exceeds a threshold indicating a possibly critical condition or possibly improper use of the kit.

Reference is now made to FIG. 6E, which is a simplified functional block diagram of the system of FIG. 1 having the functionality of FIG. 5E, namely cardiac output measurement, typically in an environment wherein a person wishes to monitor his cardiac output.

In the environment of FIG. 5E, as illustrated in FIG. 6E, wrist sensors 710 provides a pulse volume waveform via interface circuitry 712 (FIG. 5E) to recording and storage facility 716 (FIG. 5E) of general purpose computer 714 (FIG. 5E). As noted above with reference to FIG. 5E, preferably a baseline is initially established by a test conducted in an environment wherein a person is not in apparent cardiac distress. Thereafter, a further test may be conducted when the person has possible cardiac distress which is evidenced in the cardiac output parameters sensed during breathing. In both cases, the resulting waveform received from wrist sensors 710 is processed using the functionality described hereinabove with reference to FIGS. 2, 3 and 4.

In the embodiment of FIG. 6E, interface circuitry 712 may be portable so as to be readily brought to the location of the patient and preferably employs a band pass filter 744 which filters out sounds picked up by the sensors 710 outside a desired band. The output of filter 744 is amplified by an amplifier 746 and preferably supplied to a memory 748. A portable power supply 752 preferably supplies power to the foregoing components as well as to a wireless communication interface 754 and/or a wired communication interface 756 which output to general purpose computer 714 (FIG. 5E).

In the embodiment of FIG. 6E, preferably the recording and storage facility 716 stores both baseline cardiac output data and actual test cardiac output data. A cardiac output waveform receipt and storage facility 760 receives and stores data received from interface 712. A signal processing facility 762 removes unwanted data artifacts and generally prepares the data for analysis.

A signal analysis functionality 764 preferably performs the following functions on the cardiac output data:

For both the baseline and the actual test data, blood pressure and cardiac output volume are calculated.

The outputs of the signal analysis functionality 764 are preferably stored in storage facility 766.

The above-described functionality provided by software 716 is applied initially to a baseline signal and thereafter to an actual test signal. The stored results for both the baseline signal and for the test signal are supplied to software 719.

Software 719 preferably comprises comparison functionality 130 (FIG. 2), here designated by reference numeral 770, which compares the cardiac output analysis data relating to an actual test, stored by recording and storage facility 766, with baseline cardiac output analysis data also stored by facility 766 and preferably also with expected values for such cardiac output analysis data which may be received from database 138 (FIG. 2) here designated by reference numeral 771.

The comparison functionality 770 preferably provides comparison of blood pressure and cardiac output volume. It is appreciated that the functionality of FIGS. 5E, 6E, 7E and 8E, using an non-invasive light sensor, is applicable as well to blood analysis such as determination of the hemoglobin level, blood sugar level, creatinine level and blood cholesterol level.

The comparison functionality 770 preferably applies sensed differences therebetween to thresholding functionality 132 (FIG. 2), here designated by reference numeral 772, which may apply a threshold to the comparison result indicating whether the currently sensed cardiac output substantially different from the baseline and/or from the expected values therefor. Threshold functionality 772 may employ data received from a personal database 773, which may also provide data to signal analysis functionality 764 of software 716 for use in normalizing analysis data for given patient parameters.

Outputs of comparison functionality 770 and thresholding functionality 772 are preferably provided to condition description functionality 134 (FIG. 2) here designated by reference numeral 774, which provides a description of the sensed cardiac condition via an output device, such as a display 50, printer 52 and audio transducer 54 (FIG. 1).

Outputs provided by comparison functionality 770, thresholding functionality 772 and condition description functionality 774 may be further processed by recommendation functionality 136 (FIG. 2) here designated by reference numeral 776, which may provide indications/recommendations to the user via any one or more of display 50, printer 52 or transducer 54.

It is appreciated that inasmuch as the functionality of FIGS. 5E, 6E, 7E and 8E, using an non-invasive light sensor, is applicable to blood pressure and cardiac output as well to blood analysis such as determination of the hemoglobin level, blood sugar level, creatinine level and blood cholesterol level for healthy people as well as people having heart conditions, an appropriate set of recommendations may also be provided for normally healthy people. An example of application of this functionality to healthy people is that of fitness monitoring.

In certain cases where the computer is unable to provide a reliable indication/recommendation due to technical difficulties with the test, an indication such as "BECAUSE OF TECHNICAL PROBLEMS RECOMMENDATION UNAVAILABLE/CONTACT YOUR PHYSICIAN/REPEAT TEST" may be provided.

Preferably, both condition description functionality 774 and recommendation functionality 776 also receive reference data from database 771.

Preferably, both condition description functionality 774 and recommendation functionality 776 receive reference data from a database 140 (FIG. 2), here designated by reference numeral 780, which stores acceptable ranges of outputs of comparison functionality 770, normalized for age, weight, height, sex and possibly other characteristics. Database 780 is preferably employed to enable condition description functionality 774 and recommendation functionality 776 to take into account the variation in acceptable changes in various personal parameters due to variations in age, weight, height, sex and possibly other characteristics.

Communication with a remote computer, such as a controller computer 16 (FIG. 1) may be initiated automatically by the general purpose computer 714 via the network 14, for example in response to the output of comparison functionality 770, threshold functionality 772, condition description functionality 774 or recommendation functionality 776, indicating, for example a possibly acute respiratory condition or a suspected misuse or malfunction of the kit.

Thus, when one or more sensed cardiac output parameters or the comparison output lies beyond a certain threshold which may indicate either an emergency situation or a situation requiring controller intervention, communication is established immediately between the user's general purpose computer 714 and the controller computer 16 (FIG. 1) via the network 14 (FIG. 1). Communication via the network 14 with the controller computer 16 may also be initiated by a user, at the user's initiative.

Where a manned center 36 (FIG. 1) is provided, a human interface or human evaluation may also be provided to the user. It may be possible for medical personnel in the manned center 36 to directly view the patient while hearing the cardiac output directly and speaking with the user.

Reference is now made to FIG. 7E, which is a simplified flowchart illustrating the operation of the system of FIG. 1 in the operative environment of FIGS. 5E and 6E.

Initially the user accesses a system web site and carries out the initial communications and actions described hereinabove with respect to FIG. 4, which include the acquisition of a cardiac output test kit including wrist sensors 710, interface 712 and calibration container 717 (FIG. 5E) and download of operating baseline establishment software to the user's general purpose computer 714 (FIG. 5B) from the controller computer 720 (FIG. 5E) or otherwise.

The user registers with the user records database 202 of the controller computer (FIG. 3). As noted above, the user records database stores personal details of each patient for which the cardiac output sensing kit is to be used as well as general medical information regarding each such patient and results of tests conducted on that patient, using the cardiac output sensing kit, to the extent that such results are transmitted to the controller computer. Preferably, the information entered by the user into the user records database 202 of the controller computer 720 such as personal details and general medical information as well as results of the tests conducted on the patient, are stored in the personal database 771 of the user's general purpose computer 714.

Calibration of the software in the user's general purpose computer 714 is preferably carried out by using container 717 to provide a calibrated pressure reference.

When the user is ready to perform a baseline establishing cardiac output test, following current use registration and calibration of the sensors 710, a baseline test may be carried out as seen at II in FIG. 5E.

Software 719 provides appropriate signal processing and comparison of cardiac output indications received by the general purpose computer 714 from wrist sensors 710. Software 719 preferably provides an indication of blood pressure and cardiac output as well possibly blood analysis information such as determination of the hemoglobin level, blood sugar level, creatinine level and blood cholesterol level for healthy people as well as people having heart conditions.

It is appreciated that should one or more baseline values differ from expected values to a medically significant extent, such as that described hereinbelow with reference to FIG. 8E, appropriate indications/recommendations may be provided immediately to the user and the controller computer and the manned center may be employed as appropriate.

At least some of the foregoing parameters as well as possibly other parameters are employed by operating software installed at the user's general purpose computer 714.

At a later time, when a test is carried out on the same patient, preferably all of the above listed parameters are measured and analyses are performed.

The general purpose computer 714 preferably determines the differences between the baseline values and the current test values for the various parameters and analysis results and preferably indicates both the absolute difference and the percentage difference.

Based on the calculated differences between the baseline and the current test results, and using the information contained in databases 771 and 780, the operating software installed at the user's general purpose computer 714 is preferably operative to provide a condition description and recommendations to the user via the user's general purpose computer. The user's general purpose computer 714 may also employ inputs from the controller computer 720 in providing the condition description and recommendations to the user.

Depending on the comparison results and the recommendations, the user's computer may provide to the controller computer 720 the comparison results and possibly some or all of the test and baseline information.

The controller computer may analyze the comparison results and possibly some or all of the test and baseline information and provide results of the analysis to the user via the user's general purpose computer.

Preferably, the controller computer 720 makes a determination as to whether to contact a manned center 36. The user may make an independent determination whether to contact the manned center 36. A user's decision to utilize the services of the manned center which is not supported by the decision of the controller computer 720 may incur an additional charge, depending on the financial arrangements with the user.

Figure 8E:
FIG. 8E is a an illustration of application of part of an exemplary decision table to personal parameters of a given person in the operative environment of FIG. 5E.

Preferably, the condition description and recommendations are provided in accordance with a decision table, an example of which is provided in FIG. 8E.

The decision table of FIG. 8E is merely exemplary and illustrates the application of typical decision and recommendation functionality to a typical patient, a 37 year male of height 172 cm and weight 67 kg.

As noted above, based on the application of the decision and indication/recommendation functionality, an indication/recommendation such as "INSIGNIFICANT CHANGE IN CARDIAC PARAMETERS/NO ACTION REQUIRED", "SLIGHT CHANGE IN CARDIAC PARAMETER/ CONTACT PHYSICIAN/REPEAT TEST", "SIGNIFICANT CHANGE IN CARDIAC PARAMETERS/ CONTACT PHYSICIAN IMMEDIATELY" may be made.

In certain cases where the computer is unable to provide a reliable indication/recommendation due to technical difficulties with the test, an indication such as "BECAUSE OF TECHNICAL PROBLEMS RECOMMENDATION UNAVAILABLE/CONTACT YOUR PHYSICIAN/ REPEAT TEST" may be provided.

Additionally or alternatively, an automatic connection may be made to the controller computer 720 which may apply decision functionality similar to that used by the user's general purpose computer, but preferably including additional informational resources. The controller computer may also make any of the above-listed recommendations to the user. Alternatively or additionally, an automatic connection may be made to the manned center 36 (FIG. 1) wherein a human operator, such as a physician may review all of the personal parameters, analyses thereof and additional available medical information and make appropriate recommendations for action.

As noted above, complete records of all communications between the user and both the controller computer 720 and the manned center are maintained at the controller computer 720 for future reference.

Turning to FIG. 8E, it is seen that a plurality of relevant parameters, such as blood pressure and cardiac output may be measured and possibly also blood analysis information such as the hemoglobin level, blood sugar level, creatinine level and blood cholesterol level, may be determined. Additionally or alternatively, the differences between a current test and previous tests and/or predicted values, as from databases 771 and 780, for the same patient may be determined and used.

The differences are preferably categorized as to their significance and the number of parameters falling within each category are noted. It is appreciated that various parameters may be given different weighting. All of the relevant parameters are taken into account with their respective weighting and a total, suitably weighted, value is used to determine which indications/recommendations are provided to the user and whether to utilize the analysis of the controller computer 720 and/or to engage the services of the manned center 36 (FIG. 1).

In the specific example shown in FIG. 8E, four categories, each having a different weighting, are defined. Category A includes parameters having a ratio of the difference of current and baseline to the baseline measurements (D/B) typically less than 10% and is given a weight of 0. Category B includes D/B ratio typically having a variation of more than 10% and less than 20% and is given a weight of 2. Category C includes parameters typically having a D/B ratio of more than 20% and is given a weight of 4. Category D includes situations wherein any of the parameters exceed normal limits, preferably according to physician's decision, and is given a weight of 8.

Thus it is seen in FIG. 8E that the heart rate falls within Category A and the blood pressure also falls within Category A. The cardiac output falls within Category D. No parameters fall within Category C. The resulting total weighted score is thus 8.

The relationship between weighted scores and indications/recommendations for the example shown in FIG. 8E, is typically as follows:

| Weighted Score | Indication/Recommendation |
| --- | --- |
| 0–3 | "INSIGNIFICANT CHANGE IN CARDIAC OUTPUT/NO ACTION REQUIRED" |
| 4–8 | "SLIGHT CHANGE IN CARDIAC PARAMETERS/ CONTACT PHYSICIAN/REPEAT TEST" |
| 9+ | "SIGNIFICANT CHANGE IN CARDIAC PARAMETERS/ CONTACT PHYSICIAN IMMEDIATELY" |

Accordingly, the recommendation in the example of FIG. 8E is "SLIGHT CHANGE IN CARDIAC PARAMETERS/ CONTACT PHYSICIAN/REPEAT TEST".

Reference is now made to FIG. 5F, which is a pictorial illustration of part of the medical condition sensing system of FIG. 1 being employed for hearing testing, referred to hereinafter as audiometry. FIG. 5F shows three stages in audiometry, a first stage, indicated by designation I, at which calibration takes place; an optional second stage, indicated by designation II, at which a baseline reference is generated and a third stage, indicated by designation III, at which an actual test is conducted.

The context of FIG. 5F is typically a situation wherein a person wishes to test his hearing. In the environment of FIG. 5F, a user interface is provided which preferably includes a headset 810 and an optional response button 811, shown at stage I. A calibrator 812, such as a Model BA-201 or a Model BA 201-25 Bio-Acoustic Simulator, commercially available from Quest Technologies of Oconomowoc, U.S.A., which responds to predetermined sound amplitudes at predetermined frequencies is preferably provided. The headset 810 may be coupled directly to a conventional sound card of a general purpose computer 10 (FIG. 1), here designated by reference numeral 814. The calibrator 812 is operative to calibrate the sound card.

Preferably, the optional response button 811 is coupled to a serial port of computer 814. The response button may be obviated, such as by use of an Enter key. The response button 811 typically provides an electrical output to general purpose computer 814 which is preferably loaded with audiometry software 815, preferably ASAM 101, which is commercially available from Bar Advanced Control Systems Ltd. of Even Yehuda, Israel. This software provides much of the functionality described hereinbelow.

A recording and storage facility 40 (FIG. 1), here designated by reference numeral 816, at general purpose computer 814 is preferably provided by the audiometry software 815 and is operative for recording and storing calibration data and at least one baseline audiogram, typically a plot of a person's hearing threshold at various frequencies, such as 500 Hz, 1000 Hz, 2000 Hz, 3000 Hz, 4000 Hz and 8000 Hz.

Prior to generating a baseline audiogram, the sound card is calibrated, as indicated at I in FIG. 5F for the specific headset 810 which is employed.

Following calibration of the sound card, a baseline audiogram is generated by carrying out a baseline test, as seen at II in FIG. 5F. The baseline result is a plot of a person's hearing threshold at various frequencies, such as 500 Hz, 1000 Hz, 2000 Hz, 3000 Hz, 4000 Hz and 8000 Hz as well as a calculated value of the average hearing threshold of a person within the frequency range of human speech, typically 500 Hz–3000 Hz.

Software 42 (FIG. 1), here designated by reference numeral 819, which is preferably part of the audiometry software 815 resident in general purpose computer 814, provides appropriate signal processing and comparison of audiogram data received by the general purpose computer 814. Software 819 preferably provides an indication of the average hearing threshold of a person within the frequency range of human speech, typically 500 Hz–3000 Hz.

Following establishment of the baseline reference, an actual test-is carried out at a subsequent time, as indicated at III in FIG. 5F. It is seen that the test results for the actual test, shown at III, differ from the test results for the baseline reference, shown at II.

Software 819 compares the audiogram received during the actual test with the baseline established by at least one earlier test and may apply a threshold to the comparison result. Software 819 typically provides, via the general purpose computer 814, an indication of exceedance or non-exceedance of the threshold along with a suitable description of the situation which may be accompanied by recommendations for action.

Software 819 typically indicates changes the hearing threshold of a person, typically expressed in dB, as a function of the frequency of an audio input as indicated by tests taken at different times.

A controller computer 16 (FIG. 1), here designated by reference numeral 820, preferably communicates with software 819 for assisting in providing recommendations for action. Where a manned center 36 (FIG. 1) is provided, a human interface or human evaluation of the audiogram also be provided to the user. To enhance the efficacy of interface between the user and personnel in the manned center 36 (FIG. 1) a video camera 38 (FIG. 1), here designated by reference numeral 822, may be located at the user location to enable personnel in the manned center 36 to view the person undergoing testing.

In accordance with another preferred embodiment of the present invention, communication with the manned center may be actuated automatically by the system, normally through the action of the controller computer 820, for example in response to audiogram of a certain type or the output of a comparison of the currently sensed audiogram with a baseline or with a standard reference which exceeds a threshold indicating a serious problem or possibly improper use of the kit.

Figure 6F:
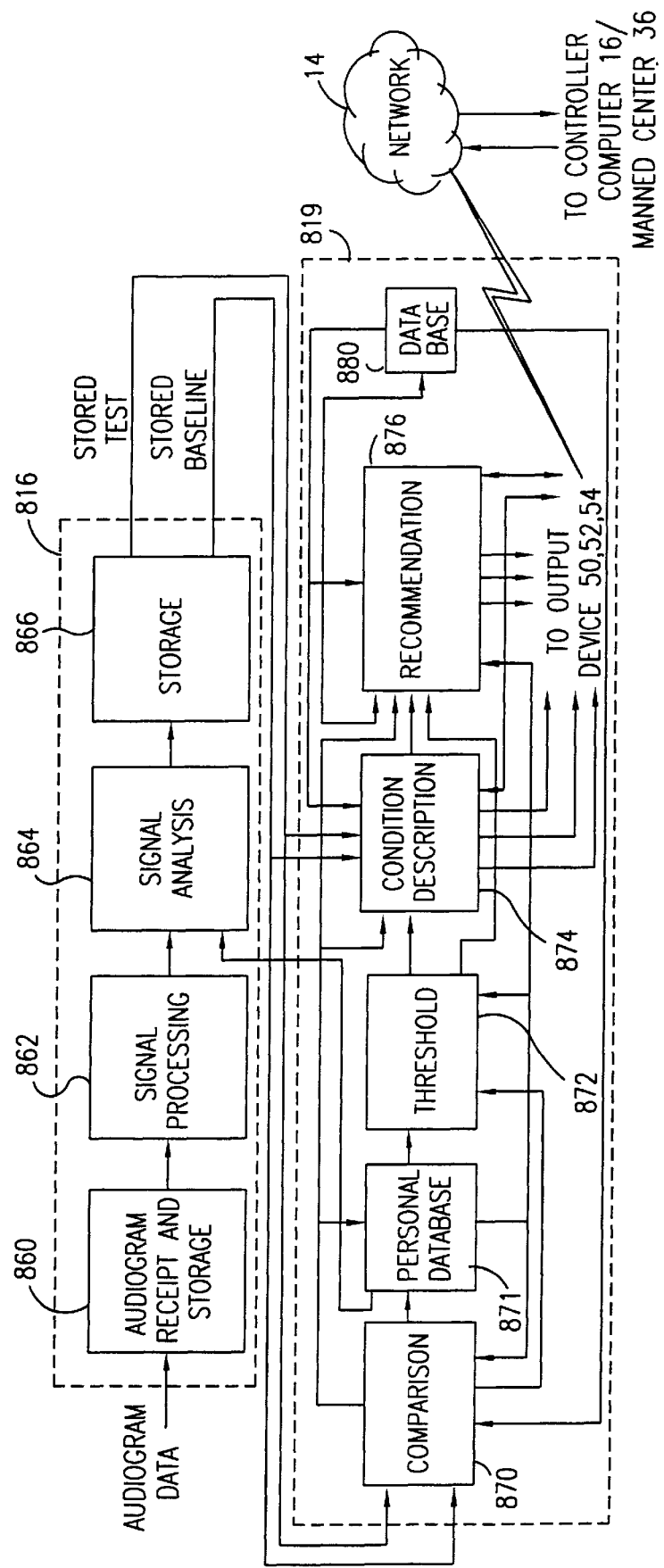
FIG. 6F is a simplified functional block diagram of the system of FIG. 1 having the functionality shown in FIG. 5F.

Reference is now made to FIG. 6F, which is a simplified functional block diagram of the system of FIG. 1 having the functionality of FIG. 5F, namely audiometry.

In the environment of FIG. 5F, as illustrated in FIG. 6F, an audiogram is provided to recording and storage facility 816 (FIG. 5F) of general purpose computer 814 (FIG. 5F). As noted above with reference to FIG. 5F, preferably a baseline is initially established. Thereafter, a further test is conducted. In both cases, the resulting audiogram is processed using the functionality described hereinabove with reference to FIGS. 2, 3 and 4.

In the embodiment of FIG. 6F, preferably the recording and storage facility 816 stores both baseline audiogram data and actual test audiogram data. A audiogram receipt and storage facility 860 receives and stores audiogram data. A signal processing facility 862 removes unwanted data artifacts and generally prepares the data for analysis.

A signal analysis functionality 864 preferably performs the following functions on the audiogram data:
calculation of the average hearing threshold of a person within the frequency range of human speech, typically 500 Hz 3000 Hz;
calculation of the average hearing threshold of a person within the frequency range of human speech, typically 4000 Hz–8000 Hz;
indication of the difference, if any, between the aforesaid two average hearing thresholds; and
indication of the rate of change in the hearing threshold as a function of frequency between 2000 Hz and 4000 Hz.

The outputs of the signal analysis functionality 864 are preferably stored in storage facility 866.

The above-described functionality provided by software 816 is applied initially to a baseline signal and thereafter to an actual test signal. The stored results for both the baseline signal and for the test signal are supplied to software 819.

Software 819 preferably comprises comparison functionality 130 (FIG. 2), here designated by reference numeral 870, which compares the audiogram analysis data relating to an actual test, stored by recording and storage facility 866 with baseline audiogram analysis data also stored by facility 866 and preferably also with expected values for such audiogram analysis data which may be received from database 138 (FIG. 2) here designated by reference numeral 871.

The comparison functionality 870 preferably provides comparison of measured, predicted and baseline values of various audiogram parameters such as:
the hearing threshold at each of a plurality of frequencies;
the average hearing threshold at each of a plurality of frequency ranges; and
the rate of change of the hearing threshold as a function of frequency.

The comparison functionality 870 preferably applies sensed differences therebetween to thresholding functionality 132 (FIG. 2), here designated by reference numeral 872, which may apply a threshold to the comparison result indicating whether the currently sensed audiogram is substantially different from the baseline and/or from the expected values therefor. Threshold functionality 872 may employ data received from personal database 871, which may also provide data to signal analysis functionality 864 of software 816 for use in normalizing analysis data for given parameters of various persons.

Outputs of comparison functionality 870 and thresholding functionality 872 are preferably provided to condition description functionality 134 (FIG. 2) here designated by reference numeral 874, which provides a description of the audiometry condition via an output device, such as a display 50, printer 52 and audio transducer 54 (FIG. 1). Outputs provided by comparison functionality 870, thresholding functionality 872 and condition description functionality 874 may be further processed by recommendation functionality 136 (FIG. 2) here designated by reference numeral 876, which may provide indications/recommendations to the user via any one or more of display 50, printer 52 or transducer 54.

Preferably, both condition description functionality 874 and recommendation functionality 876 also receive reference data from database 880.

Preferably both condition description functionality 874 and recommendation functionality 876 receive reference data from a database 140 (FIG. 2), here designated by reference numeral 880, which stores acceptable ranges of outputs of comparison functionality 870, normalized for age and possibly other characteristics. Database 880 is preferably employed to enable condition description functionality 874 and recommendation functionality 876 to take into account the variation in acceptable changes in various personal parameters due to variations in age and possibly other characteristics.

Communication with a remote computer, such as a controller computer 820, may be initiated automatically by the general purpose computer 814 via the network 14, for example in response to the output of comparison functionality 870, threshold functionality 872, condition description functionality 874 or recommendation functionality 876, indicating, for example a possibly acute auditory condition or a suspected misuse or malfunction of the kit.

Thus, when one or more sensed audiogram parameters or the comparison output lies beyond a certain threshold which may indicate a situation requiring controller intervention, communication is established between the user's general purpose computer 814 and the controller computer 820 via the network 14 (FIG. 1). Communication via the network 14 with the controller computer 16 may also be initiated by a user, at the user's initiative.

The controller computer 820 typically compares the audiogram to various known reference audiograms, including, for example reference audiograms indicating phonal trauma.

Where a manned center 36 (FIG. 1) is provided, a human interface or human evaluation may also be provided to the user. It may be possible for medical personnel in the manned center 36 to directly view the patient while hearing the audiogram directly and speaking with the user.

Reference is now made to FIG. 7F, which is a simplified flowchart illustrating the operation of the system of FIG. 1 in the operative environment of FIGS. 5F and 6F.

Initially the user accesses a system web site and carries out the initial communications and actions described hereinabove with respect to FIG. 4, which include the acquisition of a audiogram test kit including headset 810, response button 811 and calibrator 812 (FIG. 5F) and download of operating audiometry software 815 to the user's general purpose computer 814 (FIG. 5F) from the controller computer 820 (FIG. 5F) or otherwise.

The user registers with the user records database 202 of the controller computer (FIG. 3). As noted above, the user records database stores personal details of each patient for which the audiometry kit is to be used as well as general medical information regarding each such patient and results of tests conducted on that patient, using the audiogram sensing kit, to the extent that such results are transmitted to the controller computer. Preferably, the information entered by the user into the user records database 202 of the controller computer 820 such as personal details and general medical information as well as results of the tests conducted on the patient, are stored in the personal database 871 of the user's general purpose computer 814.

When the user is ready to perform a baseline establishing audiogram test, following current use registration and calibration, a baseline test is carried out as seen at II in FIG. 5F.

Software 819 provides appropriate signal processing and comparison of audiogram data received by the general purpose computer 814.

It is appreciated that should one or more baseline values differ from expected values to a medically significant extent, such as that described hereinbelow with reference to FIG. 8F, appropriate indications/recommendations may be provided immediately to the user and the controller computer and the manned center may be employed as appropriate.

At least some of the foregoing parameters as well as possibly other parameters are employed by operating software installed at the user's general purpose computer 814.

The general purpose computer 814 preferably determines the differences between the baseline values and the current test values for the various parameters and analysis results and preferably indicates both the absolute difference and the percentage difference.

Based on the calculated differences between the baseline and the current test results, and using the information contained in databases 871 and 880, the operating software installed at the user's general purpose computer 814 is preferably operative to provide a condition description and recommendations to the user via the user's general purpose computer. The user's general purpose computer 814 may also employ inputs from the controller computer 820 in providing the condition description and recommendations to the user.

Depending on the comparison results and the recommendations, the user's computer may provide to the controller computer 820 the comparison results and possibly some or all of the test and baseline information.

The controller computer may analyze the comparison results and possibly some or all of the test and baseline information and provide results of the analysis to the user via the user's general purpose computer.

Preferably, a duly certified physician at the manned center 36 confirms the comparison results and signs a report, which may be required by governmental or other authorities. The physician signature may be effected electronically in a conventional manner.

Figure 8F:
FIG. 8F is a an illustration of application of part of an exemplary decision table to personal parameters of a given person in the operative environment of FIG. 5F.

Preferably, the condition description and recommendations are provided in accordance with a decision table, an example of which is provided in FIG. 8F.

The decision table of FIG. 8F is merely exemplary and illustrates the application of typical decision and recommendation functionality to a typical patient, a 37 year male.

As noted above, based on the application of the decision and indication/recommendation functionality, an indication/recommendation such as "INSIGNIFICANT CHANGE IN AUDIOGRAM/NO ACTION REQUIRED", "POSSIBLY SIGNIFICANT CHANGE IN AUDIOGRAM/REPEAT TEST" and "SIGNIFICANT CHANGE IN AUDIOGRAM/ CONSULT PHYSICIAN" may be made. In certain cases where the computer is unable to provide a reliable indication/recommendation due to technical difficulties with the test, an indication such as "BECAUSE OF TECHNICAL PROBLEMS RECOMMENDATION UNAVAILABLE/ REPEAT TEST" may be provided.

Additionally or alternatively, an automatic connection may be made to the controller computer 820 which may apply decision functionality similar to that used by the user's general purpose computer, but preferably including additional informational resources. The controller computer may also make any of the above-listed recommendations to the user. Alternatively or additionally, an automatic connection may be made to the manned center 36 (FIG. 1) wherein a human operator, such as a physician may review all of the personal parameters, analyses thereof and additional available medical information and make appropriate recommendations for action.

As noted above, complete records of all communications between the user and both the controller computer 820 and the manned center are maintained at the controller computer 820 for future reference.

Turning to FIG. 8F, it is seen that for each of a plurality of relevant parameters, such as:

the hearing threshold at each of a plurality of frequencies;

the average hearing threshold at each of a plurality of frequency ranges; and the rate of change of the hearing threshold as a function of frequency, predicted, baseline and current test values are provided. Ratios may be calculated. Additionally or alternatively, the differences between a current test and previous tests and/or predicted values, as from databases 871 and 880, for the same patient may be determined and used.

In FIG. 8F, "slope" is measured on a standard audiogram graph according to the OSHA USA standard.

The differences are preferably categorized as to their significance and the number of parameters falling within each category are noted. It is appreciated that various parameters may be given different weighting. All of the relevant parameters are taken into account with their respective weighting and a total, suitably weighted, value is used to determine which indications/recommendations are provided to the user and whether to utilize the analysis of the controller computer 820 and/or to engage the services of the manned center 36 (FIG. 1).

In the specific example shown in FIG. 8F, three categories, each having a different weighting, are defined. Category A includes parameters having a ratio of the difference of current and baseline to the baseline measurements (D/B) less than 25% and is given a weight of 0. Category B includes parameters having a D/B value of more than 25% and is given a weight of 4. Category C includes parameters exceeding normal limits, preferably according to physician's decision, and is given a weight of 6.

It is appreciated that differences in different parameters may be measured in different ways, as most appropriate. In the example of FIG. 8E, however, the differences in all parameters are all measured as the ratio of current to baseline values.

Thus it is seen in FIG. 8F that no parameter falls within Category A and three parameters, namely:

the average hearing threshold of a person within the frequency range of human speech, typically 500 Hz–3000 Hz;

the average hearing threshold of a person within the frequency range of human speech, typically 4000 Hz–8000 Hz;

the rate of change in the hearing threshold as a function of frequency between 2000 Hz and 4000 Hz, fall within category B.

Two parameters, namely:

the average hearing threshold of a person within the frequency range of human speech, typically 4000 Hz–8000 Hz;

the rate of change in the hearing threshold as a function of frequency between 2000 Hz and 4000 Hz, fall within category C. The resulting total weighted score is thus 24.

The relationship between weighted scores and indications/recommendations for the example shown in FIG. 8E, is typically as follows:

| Weighted Score | Indication/Recommendation |
|---|---|
| 0–5 | "INSIGNIFICANT CHANGE IN AUDIOGRAM/ NO ACTION REQUIRED" |
| 6–12 | "POSSIBLY SIGNIFICANT CHANGE IN AUDIOGRAM/ REPEAT TEST" |
| 13+ | "SIGNIFICANT CHANGE IN AUDIOGRAM/ CONSULT PHYSICIAN" |

Accordingly, the recommendation in the example of FIG. 8F is "SIGNIFICANT CHANGE IN AUDIOGRAM/ CONSULT PHYSICIAN".

Figure 5G:
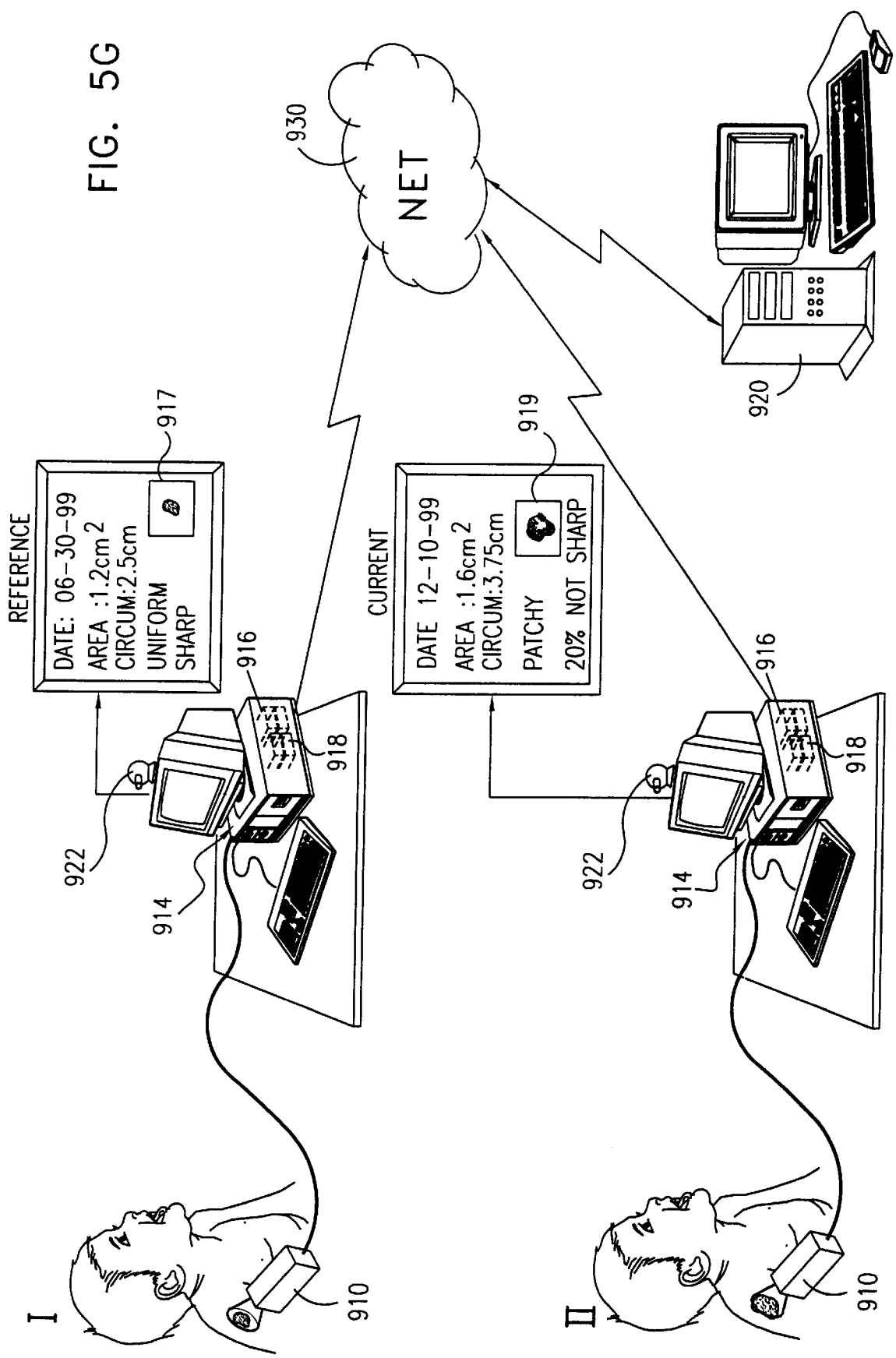
FIG. 5G is a pictorial illustration of part of the medical condition sensing system of FIG. 1 being employed for acute and chronic skin lesion monitoring sensing.

Reference is now made to FIG. 5G, which is a pictorial illustration of part of the medical condition sensing system of FIG. 1 being employed for skin condition sensing. FIG. 5G shows skin condition sensing at two different times, indicated by designations I and II, which enable analysis of progression of the skin condition. This type of sensing is appropriate for both acute conditions, such as allergic reasons, chicken pox and measles and chronic conditions such as acne and nevus, some of which could possibly progress to melanoma. The context of FIG. 5G is typically a situation wherein a person, such as a child, has a visually apparent skin condition.

In the environment of FIG. 5G, a user interface is provided which preferably includes a digital or video camera 910. A suitable camera which is provided together with skin lesion comparison software is commercially available from Romedix Ltd. of Ramat Gan, Israel under the trademark Nevuscan. The camera 910 provides an electrical output to a suitable interface of a general purpose computer 10 (FIG. 1), here designated by reference numeral 914.

A recording and storage facility 40 (FIG. 1), here designated by reference numeral 916, at general purpose computer 914 is operative for recording and storing at least one image of skin received by the general purpose computer 914 from camera 910 during at least one first test taken at least a first time, such as on Jun. 30, 1999. This first test is preferably carried out when the patient, such as a child, has a visible skin condition and may be employed to establish a baseline. The baseline result may be visualized by a representation 917.

Software 42 (FIG. 1) here designated by reference numeral 918, which is preferably resident in general purpose computer 914, provides appropriate signal processing and comparison of skin condition representations received by the general purpose computer 914 from camera 910 during a subsequent test taken at a subsequent time, such as on Aug. 15, 1999. This second test is preferably carried out when the child continues to show symptoms of the skin condition and may require attention. It is seen that the representation 919 differs from previous representation 917.

Software 918, which preferably is at least partially embodied in software supplied with the aforesaid Nevuscan product, compares the skin representations during the second test with the baseline established by at least one earlier test and may apply a threshold to the comparison result. Software 918 typically provides, via the general purpose computer 914, an indication of exceedance or non-exceedance of the threshold along with suitable description of the situation which may be accompanied by recommendations for action.

Software 918 typically compares various skin lesion parameters such as: size, shape, circumference, color, color variation, uniformity, texture and sharpness of the transition between the skin lesion and the surrounding skin.

A controller computer 16 (FIG. 1), here designated by reference numeral 920, preferably communicates, via the network 930, with software 918 for assisting in providing recommendations for action. Where a manned center 36 (FIG. 1) is provided, a human interface or human evaluation of the skin may also be provided to the user. To enhance the efficacy of interface between the user and personnel in the manned center 36 (FIG. 1) a video camera 38 (FIG. 1), here designated by reference numeral 922, may be located at the user location to enable personnel in the manned center 36 to view the patient.

In accordance with another preferred embodiment of the present invention, communication with the manned center may be actuated automatically by the system, normally through the action of the controller computer 920, for example in response to skin condition of a certain type or the output of a comparison of the currently sensed skin condition with a baseline or with a standard reference which exceeds a threshold indicating a possibly critical condition or possibly improper use of the kit.

Reference is now made to FIG. 6G, which is a simplified functional block diagram of the system of FIG. 1 having the functionality of FIG. 5G, namely skin condition sensing, typically in an environment wherein a person, such as a child, has a skin condition.

In the environment of FIG. 5G, as illustrated in FIG. 6G, camera 910 provides an image of an area of skin to recording and storage facility 916 (FIG. 5G) of general purpose computer 914 (FIG. 5G). As noted above with reference to FIG. 5G, preferably a baseline is initially established. Thereafter, at an appropriate later time a further test may be conducted. In both cases, the resulting image received from camera 910 is processed using the functionality described hereinabove with reference to FIGS. 2, 3 and 4.

In the embodiment of FIG. 6G, preferably, the recording and storage facility 916 stores both baseline skin image data and later test skin image data. A skin image signal receipt and storage facility 960 receives and stores the signal received from camera 910. A signal processing facility 962 removes unwanted signal artifacts and generally prepares the signal for analysis.

A signal analysis functionality 964 preferably includes at least part of the skin lesion comparison software commercially available from Romedix Ltd. of Ramat Gan, Israel under the trademark Nevuscan and preferably performs the following functions on the skin signals:

Determination of area of skin lesions;

Determination of shape of skin lesions;

Determination of circumference of skin lesions;

Determination of color of skin lesions;

Determination of color variation of skin lesions;

Determination of uniformity of skin lesions;

Determination of texture of skin lesions; and

Determination of sharpness of the transition between the skin lesion and the surrounding skin;

Normalization of the above parameters for the age or other characteristics, using patient data from a personal database, typically forming part of software 918.

The outputs of the signal analysis functionality 964 for the signal are preferably stored in storage facility 966.

The above-described functionality provided by software 916 preferably is applied initially to baseline data and thereafter to further test data. The stored results for both baseline and further tests are supplied to software 918.

Comparison functionality 130 (FIG. 2), here designated by reference numeral 970, which is included in software 918 (FIG. 5G), compares the skin image and analysis data relating thereto stored by recording and storage facility 916 with a baseline skin image and analysis data relating thereto, also stored by facility 916. Comparison functionality 970 preferably applies sensed differences therebetween to thresholding functionality 132 (FIG. 2), here designated by reference numeral 972, which may apply a threshold to the comparison result indicating whether the currently sensed skin image data is substantially different from the baseline. Threshold functionality may employ data received from a personal database 974, which may also provide data to signal analysis functionality 964 of software 916 for use in normalizing analysis data for given patient parameters.

Outputs of comparison functionality 970 and thresholding functionality 972 are preferably provided to condition description functionality 134 (FIG. 2) here designated by reference numeral 975, which provides a description of the sensed respiratory condition via an output device, such as a display 50, printer 52 and audio transducer 54 (FIG. 1). Outputs provided by comparison functionality 970, thresholding functionality 972 and condition description functionality 975 may be further processed by recommendation functionality 136 (FIG. 2) here designated by reference numeral 976, which may provide indications/recommendations to the user via any one or more of display 50, printer 52 or transducer 54.

Preferably, both condition description functionality 975 and recommendation functionality 976 receive reference data from a database 140 (FIG. 2), designated by reference numeral 980, which stores acceptable ranges of outputs of comparison functionality 970, normalized for age and possibly other characteristics. Database 980 is preferably employed to enable condition description functionality 975 and recommendation functionality 976 to take into account the variation in acceptable changes in various personal parameters due to variations in age and possibly other characteristics.

Communication with a remote computer, such as a controller computer 16 (FIG. 1) is preferably initiated automatically by the general purpose computer 914 via the network 14, for example in response to the output of comparison functionality 970, threshold functionality 972, condition description functionality 975 or recommendation functionality 976, indicating, any medically significant change in the skin lesion.

Thus, when a sensed skin parameter or the comparison output lies beyond a certain threshold which may indicate a medically significant skin event, communication is established immediately between the user's general purpose computer 914 and the controller computer 16 (FIG. 1) via the network 14 (FIG. 1). Communication via the network 14 with the controller computer 920 may also be initiated by a user, at the user's initiative. This communication enables reference data to be readily accesses for evaluation of the skin event.

Where a manned center 36 (FIG. 1) is provided, a human interface or human evaluation may also be provided to the user. It may be possible for medical personnel in the manned center 36 to directly view the patient while hearing and speaking with the user.

Reference is now made to FIG. 7G, which is a simplified flowchart illustrating the operation of the system of FIG. 1 in the operative environment of FIGS. 5G and 6G.

Initially the user accesses a system web site and carries out the initial communications and actions described hereinabove with respect to FIG. 4, which include the acquisition of a skin examination test kit including a camera such as camera 920 and download of operating software to the user's general purpose computer 914 (FIG. 5G) from the controller computer 920 (FIG. 5G) or otherwise. The user registers with the user records database 202 of the controller computer (FIG. 3). As noted above, the user records database stores personal details of each patient for which the skin sensing kit is to be used as well as general medical information regarding each such patient and results of tests conducted on that patient, using the skin sensing kit, to the extent that such results are transmitted to the controller computer. Preferably, the information entered by the user into the user records database of the controller computer 920 is also stored in the user's general purpose computer 914. Thus, such as the personal details and general medical information as well as results of the tests conducted on the patient, are stored in the personal database 974 of the user's general purpose computer 914.

When the user is ready to perform a baseline establishing skin test, following current use registration, a baseline determination is carried out typically in the following manner:

The skin image data is recorded at the user's general purpose computer 914.

As noted above, the following determinations are made with respect to detected skin lesions:

Determination of area of skin lesions;

Determination of shape of skin lesions;

Determination of circumference of skin lesions;

Determination of color of skin lesions;

Determination of color variation of skin lesions;

Determination of uniformity of skin lesions;

Determination of texture of skin lesions; and

Determination of sharpness of the transition between the skin lesion and the surrounding skin.

At least some of the above parameters are preferably normalized for the age of the patient.

It is appreciated that should one or more baseline values differ from expected values to a medically significant extent, such as that described hereinbelow with reference to FIG. 8G, appropriate indications/recommendations may be provided immediately to the user and the controller computer and the manned center may be employed as appropriate.

At a later time, when a test is carried out on the same patient preferably all of the above listed parameters are measured and analyses are performed. Some of the above parameters are preferably normalized for the age of the patient.

At least some of the foregoing parameters as well as possibly other parameters are employed by operating software installed at the user's general purpose computer 914. Some or all of the parameters are preferably stored both at the user's general purpose computer 914 and in user records database 202 at the controller computer 920.

The general purpose computer 914 preferably determines the differences between the baseline values and the current test values for the various parameters and analysis results and preferably indicates both the absolute difference and the percentage difference.

Based on the calculated differences between the baseline and the current test results, and using the information contained in databases 974 and 980, the operating software installed at the user's general purpose computer 914 is preferably operative to provide a condition description and recommendations to the user via the user's general purpose computer. The user's general purpose computer 914 may also employ inputs from the controller computer 920 in providing the condition description and recommendations to the user.

Depending on the comparison results and the recommendations, the user's computer may provide to the controller computer 920 the comparison results and possibly some or all of the test and baseline information.

The controller computer may analyze the comparison results and possibly some or all of the test and baseline information and provide results of the analysis to the user via the user's general purpose computer.

Preferably, the controller computer 920 makes a determination as to whether to contact a manned center 36. The user may make an independent determination whether to contact the manned center 36. A user's decision to utilize the services of the manned center which is not supported by the decision of the controller computer 920 may incur an additional charge, depending on the financial arrangements with the user.

Figure 8G:
FIG. 8G is a an illustration of application of part of an exemplary decision table to personal parameters of a given person in the operative environment of FIG. 5G.

Preferably, the condition description and recommendations are provided in accordance with a decision table, an example of which is provided in FIG. 8G.

The decision table of FIG. 8G is merely exemplary and illustrates the application of typical decision and recommendation functionality to a typical patient, a 10 year child having skin lesions over two weeks.

As noted above, based on the application of the decision and indication/recommendation functionality, indications/recommendations such as "INSIGNIFICANT CHANGE IN SKIN LESION/NO ACTION REQUIRED", "SIGNIFICANT CHANGE IN SKIN LESION/CONSULT PHYSICIAN" may be made. In certain cases where the computer is unable to provide a reliable indication/recommendation due to technical difficulties with the test, an indication such as "BECAUSE OF TECHNICAL PROBLEMS RECOMMENDATION UNAVAILABLE/CONTACT YOUR PHYSICIAN/REPEAT TEST" may be provided.

Additionally or alternatively, an automatic connection may be made to the controller computer 920 which may apply decision functionality similar to that used by the user's general purpose computer, but preferably including additional informational resources, such as a library of images of skin lesions indicating the procession thereof. The controller computer preferably provides a basis for diagnosis based on similarity of the sensed patient skin image data to image data stored in the library and may also make any of the above-listed recommendations to the user. Alternatively or additionally, an automatic connection may be made to the manned center 36 (FIG. 1) wherein a human operator, such as a physician may review all of the personal parameters, analyses thereof and additional available medical information and make appropriate recommendations for action.

As noted above, complete records of all communications between the user and both the controller computer 920 and the manned center are maintained at the controller computer for future reference.

Turning to FIG. 8G, it is seen that for each of a plurality of relevant skin lesion parameters, such as: size, shape, circumference, color, color variation, uniformity and texture, baseline and current test values are provided. Ratios and differences are calculated. Additionally or alternatively, the differences between a current test and previous tests and/or predicted values, as from databases 974 and 980, for the same patient may be determined and used.

The differences are preferably categorized as to their significance and the number of parameters falling within each category are noted. It is appreciated that various parameters may be given different weighting. All of the relevant parameters are taken into account with their respective weighting and a total, suitably weighted, value is used to determine which indications/recommendations are provided to the user and whether to utilize the analysis of the controller computer 920 and/or to engage the services of the manned center 36 (FIG. 1).

In the specific example shown in FIG. 8G, three categories, each having a different weighting, are defined. Category A includes parameters having a ratio of the difference of current and baseline to the baseline measurements (D/B) less than 20% and is given a weight of 0. Category B includes parameter D/B with value more than 20% and is given a weight of 4. Category C includes parameters which fall within pathological patterns as indicated in a stored reference library and is given a weight of 6.

It is appreciated that differences in different parameters may be measured in different ways, as most appropriate. In the example of FIG. 8G, however, the differences in all parameters are all measured as the ratio of current to baseline values.

Thus it is seen in FIG. 8G that no parameter falls within Category A and two parameters, namely area and circumference of skin lesions, fall within category B.

Two parameters, namely uniformity of skin lesions and sharpness of the transition between the skin lesion and the surrounding skin, fall within category C. The resulting total weighted score is thus 20.

The relationship between weighted scores and indications/recommendations for the example shown in FIG. 8G, is typically as follows:

| Weighted Score | Indication/Recommendation |
|---|---|
| 0–6 | "INSIGNIFICANT CHANGE IN SKIN LESIONS/ NO ACTION REQUIRED" |
| 7+ | "SIGNIFICANT CHANGE IN SKIN LESIONS/ CONSULT PHYSICIAN" |

Accordingly, the recommendation in the example of FIG. 8G is "SIGNIFICANT CHANGE IN SKIN LESIONS/ CONSULT PHYSICIAN". As indicated above, preferably, the reference library is employed to provide evaluation of the skin lesion and comparison thereof to known lesions.

Reference is now made to FIG. 5H, which is a pictorial illustration of part of the medical condition sensing system of FIG. 1 being employed for vision sensing. The context of FIG. 5H is typically a situation wherein a person is having his vision tested.

In the environment of FIG. 5H, a user interface is provided which preferably includes a vision testing headset 1010, such as a virtual reality headset, typically a V8 Head Mount Display, commercially available from Virtual research Systems, Inc of Santa Clara, Calif., which is modified to permit ready replacement or displacement of lenses therein. The vision testing headset 1010 provides an electrical output typically via interface circuitry 1012, typically commercially available with the V8 Head Mount Display, to a suitable interface of a general purpose computer 10 (FIG. 1), here designated by reference numeral 1014.

A recording and storage facility 40 (FIG. 1), here designated by reference numeral 1016, at general purpose computer 1014 is operative for recording and storing at least one baseline plot of vision received by the general purpose computer 1014 from vision testing headset 1010 during at least one first test. Typical test results are shown at reference numeral 1017 on a display of the general purpose computer 1014.

Typically the test procedure involves presenting to the vision test in accordance with a commercially available test procedure, such as the AVAT test procedure developed by Bar Advanced Control Systems Ltd. of Even Yehuda, Israel, which is described in published PCT Patent Application WO 98/02083, preferably using the commercially available AVAT keyboard, which is also commercially available from Bar Advanced Control Systems Ltd. of Even Yehuda, Israel. Additionally or alternatively, commercially available speech recognition software can be used for receiving subject responses. AVAT software typically uses signals for determining visual acuity threshold such as "C" marks of different sizes, and indicated by reference numeral 1018 in FIG. 5H.

Software 42 (FIG. 1) here designated by reference numeral 1019, which typically includes software embodying the AVAT test procedure, which is preferably resident in general purpose computer 1014, provides appropriate signal processing and comparison of vision data received by the general purpose computer 1014 from vision testing headset 1010 during at least one subsequent test taken at a later time.

Software 1019 compares the vision data received during the second test with the baseline established by at least one earlier test and may apply a threshold to the comparison result. Software 1019 typically provides via the general purpose computer 1014 an indication of exceedance or non-exceedance of the threshold along with suitable description of the situation which may be accompanied by recommendations for action.

Software 1019 typically compares various vision parameters such as visual acuity at 40 cm, 80 cm and 600 cm, color vision, depth perception and phoria.

A controller computer 16 (FIG. 1), here designated by reference numeral 1020, preferably communicates, via the network 1021, with software 1019 for assisting in providing recommendations for action. Where a manned center 36 (FIG. 1) is provided, a human interface or human evaluation of the vision data may also be provided to the user. To enhance the efficacy of interface between the user and personnel in the manned center 36 (FIG. 1) a video camera 38 (FIG. 1), here designated by reference numeral 1022, may be located at the user location to enable personnel in the manned center 36 to view the patient who is experiencing apparent vision difficulties.

In accordance with another preferred embodiment of the present invention, communication with the manned center may be actuated automatically by the system, normally through the action of the controller computer 1020, for example in response to vision of a certain type or the output of a comparison of the currently sensed vision with a baseline or with a standard reference which exceeds a threshold indicating vision difficulty or possibly improper use of the kit.

Figure 6H:
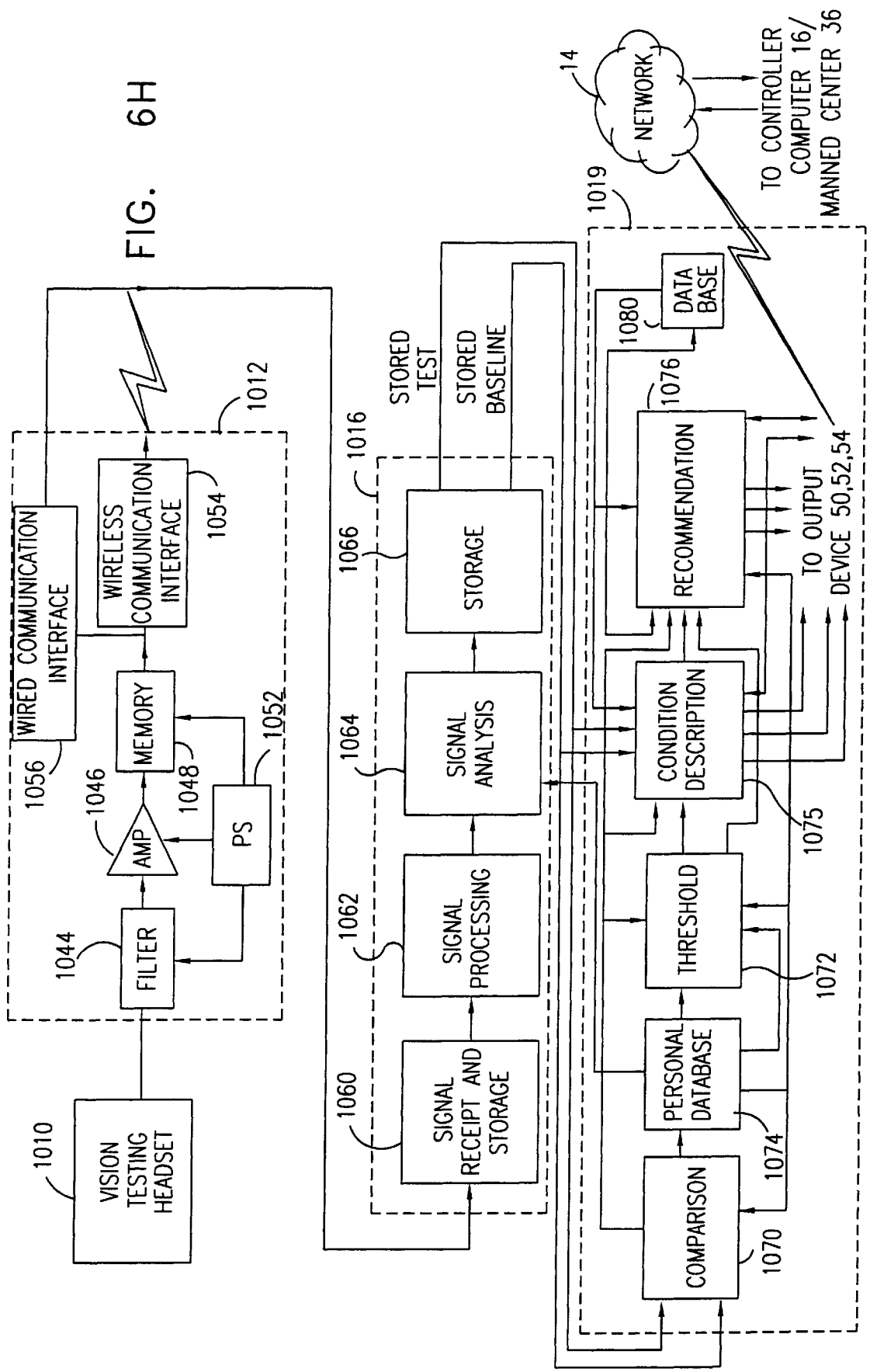
FIG. 6H is a simplified functional block diagram of the system of FIG. 1 having the functionality shown in FIG. 5H.

Reference is now made to FIG. 6H, which is a simplified functional block diagram of the system of FIG. 1 having the functionality of FIG. 5H, namely vision sensing.

In the environment of FIG. 5H, as illustrated in FIG. 6H, vision testing headset 1010 provides vision data via interface circuitry 1012 (FIG. 5H) to recording and storage facility 1016 (FIG. 5H) of general purpose computer 1014 (FIG. 5H). As noted above with reference to FIG. 5H, preferably a baseline is initially established by an earlier test. Thereafter, a further test may be conducted at an appropriate time. In both cases, the resulting vision data received from vision testing headset 1010 is processed using the functionality described hereinabove with reference to FIGS. 2, 3 and 4.

In the embodiment of FIG. 6H, interface circuitry 1012 is preferably portable and preferably employs a band pass filter 1044 which filters out noise outside a desired band. The output of filter 1044 is amplified by an amplifier 1046 and preferably supplied to a memory 1048. A portable power supply 1052 preferably supplies power to the foregoing components as well as to a wireless communication interface 1054 and/or a wired communication interface 1056 which output to general purpose computer 1014 (FIG. 5H).

In the embodiment of FIG. 6H, preferably, the recording and storage facility 1016 stores both baseline vision data and later test vision data. A vision data receipt and storage facility 1060 receives and stores the data received from interface 1012. A signal processing facility 1062 removes unwanted signal artifacts and generally prepares the data for analysis.

Signal analysis functionality 1064 preferably performs the following functions on the vision data signals:

Determination of various vision parameters such as visual acuity at 40 cm, 80 cm and 600 cm;

Determination of color vision;

Determination of depth perception;

Determination of phoria.

Normalization of the above parameters may be carried out for the age and possibly other parameters of the patient, using patient data from a personal database 1074, typically forming part of software 1019.

The outputs of the signal analysis functionality 1064 for the vision data is preferably stored in storage facility 1066.

The above-described functionality is provided by facility 1016 and is applied initially to a baseline test and thereafter to subsequent tests. The stored results for both the baseline data and for the test data are supplied to software 1019.

Comparison functionality 130 (FIG. 2), here designated by reference numeral 1070, which is included in software 1019 (FIG. 5H), compares the vision data and analysis data relating thereto stored by recording and storage facility 1016 with baseline vision data and analysis data relating thereto, also stored by facility 1016. Comparison functionality 1070 preferably applies sensed differences therebetween to thresholding functionality 132 (FIG. 2), here designated by reference numeral 1072, which may apply a threshold to the comparison result indicating whether the currently sensed vision parameters are substantially different from the baseline. Threshold functionality may employ data received from a personal database 1074, which may also provide data to signal analysis functionality 1064 of software 1016 for use in normalizing analysis data for given patient parameters.

Outputs of comparison functionality 1070 and thresholding functionality 1072 are preferably provided to condition description functionality 134 (FIG. 2) here designated by reference numeral 1075, which provides a description of the vision condition of the subject via an output device, such as a display 50, printer 52 and audio transducer 54 (FIG. 1). Outputs provided by comparison functionality 1070, thresholding functionality 1072 and condition description functionality 1075 may be further processed by recommendation functionality 136 (FIG. 2) here designated by reference numeral 1076, which may provide indications/recommendations to the user via any one or more of display 50, printer 52 or transducer 54.

Preferably, both condition description functionality 1075 and recommendation functionality 1076 receive reference data from a database 140 (FIG. 2), designated by reference numeral 1080, which stores acceptable ranges of outputs of comparison functionality 1070, normalized for age and possibly other characteristics. Database 1080 is preferably employed to enable condition description functionality 1075 and recommendation functionality 1076 to take into account the variation in acceptable changes in various vision parameters due to variations in age and possibly other characteristics.

Communication with a remote computer, such as controller computer 1020 may be initiated automatically by the general purpose computer 1014 via the network 14, for example in response to the output of comparison functionality 1070, threshold functionality 1072, condition description functionality 1075 or recommendation functionality 1076, indicating, for example a possibly acute vision condition or change therein or a suspected misuse of the kit.

Thus, when a sensed vision parameter or the comparison output lies beyond a certain threshold which may indicate either an acute situation or a situation requiring controller intervention, communication is established immediately between the user's general purpose computer 1014 and the controller computer 1020 via the network 14 (FIG. 1). Communication via the network 14 with the controller computer 1020 may also be initiated by a user, at the user's initiative.

Where a manned center 36 (FIG. 1) is provided, a human interface or human evaluation may also be provided to the user the manned center 36 to view the test subject. It may be possible for medical personnel in the manned center 36 to directly view the patient while hearing the vision directly and speaking with the user.

Reference is now made to FIG. 7H, which is a simplified flowchart illustrating the operation of the system of FIG. 1 in the operative environment of FIGS. 5H and 6H.

Initially the user accesses a system web site and carries out the initial communications and actions described hereinabove with respect to FIG. 4, which include the acquisition of a vision testing headset and download of operating baseline establishment software to the user's general purpose computer 1014 (FIG. 5H) from the controller computer 1020 (FIG. 5H) or otherwise. The user registers with the user records database 202 of the controller computer 1020 (FIG. 5H). As noted above, the user records database 202 stores personal details of each patient for which the vision sensing kit is to be used as well as general medical information regarding each such patient and results of tests conducted on that patient, using the vision sensing kit, to the extent that such results are transmitted to the controller computer. Preferably, the information entered by the user into the user records database 202 of the controller computer 1020 is also stored in the user's general purpose computer 1014. Thus, such as personal details and general medical information as well as the tests conducted on the patient, are stored in the personal database 1074 of the user's general purpose computer 1014.

When the user is ready to perform a baseline establishing vision test, following current use registration, a baseline determination is carried out typically in the following manner:

The vision data is recorded at the user's general purpose computer 1014.

The following determinations are preferably carried out at the user's general purpose computer:

Determination of various vision parameters such as visual acuity at 40 cm, 80 cm and 600 cm;

Determination of color vision;

Determination of depth perception;

Determination of phoria.

Some of the above parameters are preferably normalized for the age and possibly other characteristics of the subject.

It is appreciated that should one or more baseline values differ from expected values to a medically significant extent, such as that described hereinbelow with reference to FIG. 8H, appropriate indications/recommendations may be provided immediately to the user and the controller computer and the manned center may be employed as appropriate.

At a later time, when a test is carried out on the same subject, preferably all of the above listed parameters are measured and analyses are performed. Some of the above parameters are preferably normalized for the age and possibly other characteristics of the patient.

At least some of the foregoing parameters as well as possibly other parameters are employed by operating software installed at the user's general purpose computer 1014. Some or all of the parameters are preferably stored both at the user's general purpose computer 1014 and in user records database 202 at the controller computer 1020.

The general purpose computer 1014 preferably determines the differences between the baseline values and the current test values for the various parameters and analysis results and preferably indicates both the absolute difference and the percentage difference.

Based on the calculated differences between the baseline and the current test results, and using the information contained in databases 1074 and 1080, the operating software installed at the user's general purpose computer 1014 is preferably operative to provide a condition description and recommendations to the user via the user's general purpose computer. The user's general purpose computer 1014 may also employ inputs from the controller computer 1020 in providing the condition description and recommendations to the user.

Depending on the comparison results and the recommendations, the user's computer may provide to the controller computer 1020 the comparison results and possibly some or all of the test and baseline information.

The controller computer may analyze the comparison results and possibly some or all of the test and baseline information and provide results of the analysis to the user via the user's general purpose computer.

Preferably, the controller computer 1020 makes a determination as to whether to contact a manned center 36. The user may make an independent determination whether to contact the manned center 36. A user's decision to utilize the services of the manned center which is not supported by the decision of the controller computer 1020 may incur an additional charge, depending on the financial arrangements with the user.

Preferably, the condition description and recommendations are provided in accordance with a decision table, an example of which is provided in FIG. 8H.

The decision table of FIG. 8H is merely exemplary and illustrates the application of typical decision and recommendation functionality to a typical subject, a 40 year old male.

As noted above, based on the application of the decision and indication/recommendation functionality, an indication/ recommendation such as "VISION WITHIN ACCEPTABLE LIMITS", "CHANGE IN VISION FROM PREVIOUS EXAMINATION OR VISION OUTSIDE NORMAL LIMITS/CONTACT VISION PROFESSIONAL/REPEAT TEST" and "VISION NOT WITHIN ACCEPTABLE LIMITS/CONSULT VISION PROFESSIONAL".

In certain cases where the computer is unable to provide a reliable indication/recommendation due to technical difficulties with the test, an indication such as "BECAUSE OF TECHNICAL PROBLEMS RECOMMENDATION UNAVAILABLE/CONTACT YOUR PHYSICIAN/REPEAT TEST" may be provided.

Additionally or alternatively, an automatic connection may be made to the controller computer 1020 which may apply decision functionality similar to that used by the user's general purpose computer, but preferably including additional informational resources. The controller computer may also make any of the above-listed recommendations to the user. Alternatively or additionally, an automatic connection may be made to the manned center 36 (FIG. 1) wherein a human operator, such as a physician may review all of the personal parameters, analyses thereof and additional available medical information and make appropriate recommendations for action.

As noted above, complete records of all communications between both the user and the controller computer 1020 and the manned center 36 are maintained at the controller computer for future reference.

Turning to FIG. 8H, it is seen that for each of a plurality of relevant parameters, such as visual acuity at 40 cm, 80 cm and 600 cm; color vision; depth perception and phoria baseline and current test values are provided. Differences are calculated. Additionally or alternatively, the differences between a current test and previous tests, for the same subject may be determined and used.

The differences are preferably categorized as to their significance and the number of parameters falling within each category are noted. It is appreciated that various parameters may be given different weighting. All of the relevant parameters are taken into account with their respective weighting and a total, suitably weighted, value is used to determine which indications/recommendations are provided to the user and whether to utilize the analysis of the controller computer 1020 and/or to engage the services of the manned center 36 (FIG. 1).

In the specific example shown in FIG. 8H, three categories, each having a different weighting, are defined. Category A includes parameters having a current to baseline (C/B) ratio less than 30% and is given a weight of 0. Category B includes parameters having a current to baseline (C/B) ratio above 30% and is given a weight of 8. Category C includes parameters which lie outside normal limits, preferably according to physician's decision, and is given a weight of 4.

It is appreciated that differences in different parameters may be measured in different ways, as most appropriate.

It is seen in FIG. 8H that two parameters, namely visual acuity at 40 cm and depth perception, fall within Category A no parameters fall within Category B. One parameter, namely visual acuity at 6 meters, falls within Category C. The resulting total weighted score is thus 4.

The relationship between weighted scores and indications/recommendations for the example shown in FIG. 8H is typically as follows:

| Weighted Score | Indication/Recommendation |
|---|---|
| 0–3 | "VISION WITHIN ACCEPTABLE LIMITS" |
| 4–12 | "CHANGE IN VISION FROM PREVIOUS EXAMINATION OR VISION OUTSIDE NORMAL LIMITS/ CONTACT VISION PROFESSIONAL/REPEAT TEST" |
| 13+ | "VISION NOT WITHIN ACCEPTABLE LIMITS/CONSULT VISION PROFESSIONAL" |

Accordingly, the recommendation in the example of FIG. 8H is "CHANGE IN VISION FROM PREVIOUS EXAMINATION OR VISION OUTSIDE NORMAL LIMITS/CONTACT VISION PROFESSIONAL/REPEAT TEST"

Turning to FIG. 8H, it is seen that for each of a plurality of relevant parameters, baseline and current test values are provided. Absolute and percentage differences are calculated. Additionally or alternatively, the differences between a current test and previous tests, for the same subject be determined and used.

The differences are preferably categorized as to their significance and the number of parameters falling within each category are noted. It is appreciated that various parameters may be given different weighting. All of the relevant parameters are taken into account with their respective weighting and a total, suitably weighted value is used to determine which indications/recommendations are provided to the user and whether to utilize the analysis of the controller computer 1020 and/or to engage the services of the manned center 36 (FIG. 1).

The present invention has been described hereinabove with reference to a number of specific applications. It is appreciated that the invention is not limited to those applications and that the invention may be used in many other applications. Some examples of additional applications include the following:

Heart sound monitoring, which may include functionality very similar to that of lung sound monitoring described hereinabove.

Fetal monitoring, which may involve sensing various biometric parameters, such as fetal ECG and Doppler of the fetal heart and umbilical cord artery, and differentiating those of the fetus from those of the mother. The fetal monitoring may also include monitoring contractions of the uterus.

Sleep apnea monitoring typically employing functionality very similar to that of lung sound monitoring described hereinabove.

Alertness monitoring, such as using a combination of biometric parameters, including, for example, posture monitoring, response speed monitoring, eye-hand coordination monitoring and eye tracking.

It will be appreciated by persons skilled in the art that the present invention is not limited by what has been particularly shown and described hereinabove. Rather the present invention includes both combinations and subcombinations of the various features described hereinabove as well as modifications and variations thereof which would occur to a person skilled in the art upon reading the foregoing description and which are not in the prior art.

What is claimed is:

1. A medical condition sensing system comprising:
   a multiplicity of general purpose computers disposed in user locations and being connectable via an on-line connection with a computer network to at least one controller computer remote from at least one of said user locations;

personal parameter measuring software resident on at least one of said multiplicity of general purpose computers fur measuring at least one personal parameter of at least one user;

personal parameter reference generating software resident on at least one of said multiplicity of general purpose computers and said at least one controller computer for establishing a reference for said at least one personal parameter; and personal parameter comparison software resident on at least one of said multiplicity of general purpose computers for comparing at least one currently measured personal parameter with a corresponding reference and providing a comparison output without an on-line connection to said controller.

2. A medical condition sensing system according to claim 1 and also comprising alert indication software resident on at least one of said multiplicity of general purpose computers and said at least one controller computer for providing a generally real time alert indication to said user based at least partially on said comparison output.

3. A medical condition sensing system according to claim 2 and wherein said alert indication software is resident on said multiplicity of general purpose computers.

4. A medical condition sensing system according to claim 1 and wherein said reference is a personal parameter baseline constructed from pre-real time measurements of said personal parameter.

5. A medical condition sensing system according to claim 1 and wherein said reference is a calibration reference employing a measurement of a personal parameter based on a calibration input.

6. A medical condition sensing system according to claim 1 and wherein said reference is a calibration reference based on a calibration input.

7. A medical condition sensing system according to claim 1 and wherein said reference is a calibration reference based on a calibration input supplied from another computer via said computer network.

8. A medical condition sensing system according to claim 1 and wherein said reference is a calibration reference employing a measurement of a personal parameter based on a calibration input supplied from another computer via said computer network.

9. A medical condition sensing system according to claim 8 and wherein said personal parameter comparison software is operative to compare at least one currently measured personal parameter with said calibration reference.

10. A medical condition sensing system according to claim 1 and also comprising notification software resident on at least one of said multiplicity of general purpose computers and said at least one controller for transmitting a notification from one of said at multiplicity of general purpose computers to at least one other computer based on said comparison output.

11. A medical condition sensing system according to claim 1 and wherein said personal parameter comprises a heart function parameter.

12. A medical condition sensing system according to claim 1 and wherein said personal parameter comprises a blood parameter.

13. A medical condition sensing system according to claim 1 and wherein said personal parameter comprises a electrocardiogram parameter.

14. A medical condition sensing system according to claim 1 and wherein said personal parameter comprises a hearing function parameter.

15. A medical condition sensing system according to claim 1 and wherein said personal parameter comprises a skin appearance parameter.

16. A medical condition sensing system according to claim 1 and wherein said personal parameter comprises a tissue appearance parameter.

17. A medical condition sensing system according to claim 1 and wherein said personal parameter comprises an optically sensible parameter.

18. A medical condition sensing system according to claim 1 and wherein said personal parameter comprises an electrically sensible parameter.

19. A medical condition sensing system according to claim 1 and wherein said personal parameter comprises an thermally sensible parameter.

20. A medical condition sensing system according to claim 1 and wherein said personal parameter comprises an audibly sensible parameter.

21. A medical condition sensing system according to claim 1 and wherein said personal parameter comprises a chemically sensible parameter.

22. A medical condition sensing system according to claim 1 and wherein said personal parameter comparison software is operative to compare optical images of at least one body region.

23. A medical condition sensing system according to claim 1 and wherein said personal parameter measuring software is operative to measure at least one personal parameter of at least one user in response to an input supplied to the user.

24. A medical condition sensing system according to claim 23 and wherein said personal parameter measuring software includes feedback software for calibrating the input supplied to the user.

25. A medical condition sensing system according to claim 23 and also comprising feedback circuitry for calibrating the input supplied to the user.

26. A medical condition sensing system according to claim 24 and wherein said feedback software is operative to communicate between a general purpose computer and said controller computer over said computer network.

27. A medical condition sensing system according to claim 25 and wherein said feedback circuitry is operative to communicate between a general purpose computer and said controller computer over said computer network.

28. A medical condition sensing method according to claim 23 and wherein said personal parameter measuring software includes feedback software for calibrating the input supplied to the user.

29. A medical condition sensing method according to claim 28 and also comprising employing feedback circuitry for calibrating the input supplied to the user.

30. A medical condition sensing method according to claim 29 and wherein said feedback software is operative to communicate between a general purpose computer and said controller computer over said computer network.

31. A medical condition sensing method according to claim 30 and wherein said feedback circuitry is operative to communicate between a general purpose computer and said controller computer over said computer network.

32. A medical condition sensing system according to claim 1 and also comprising software utilizing the output of at least one of said personal parameter measuring software, said personal parameter reference generating software, and said personal parameter comparison software for providing at least one of recommendations and indications to a user.

33. A medical condition sensing system according to claim 32 and also comprising a manned center accessible at least via said computer network for receiving at least some of said output of at least one of said personal parameter measuring software, said personal parameter reference generating software said personal parameter comparison software and at least one of recommendations and indications to a user and providing health professional interaction with the user.

34. A medical condition sensing system according to claim 33 and wherein at least one of said recommendations and indications as well as the criteria therefor is determinable by a user's health professional by transmitting instructions to at least one of said controller computer and said general purpose computer via said computer network.

35. A medical condition sensing system according to claim 1 and also comprising a manned center accessible at least via said computer network for receiving at least some of said output of at least one of said personal parameter measuring software, said personal parameter reference generating software said personal parameter comparison software and at least one of recommendations and indications to a user and providing health professional interaction with the user.

36. A medical condition sensing system according to claim 35 and wherein at least one of said recommendations and indications as well as the criteria therefor is determinable by a user's health professional by transmitting instructions to at least one of said controller computer and said general purpose computer via said computer network.

37. A medical condition sensing system according to claim 35 and wherein said manned center employs a personal physician of the user and communicates with him via through at least one of telephone and data links via at least one of wired and wireless communication media.

38. A medical condition sensing system according to claim 1 and also comprising personal parameter analysis software resident on at least one of said multiplicity of general purpose computers and said at least one controller computer for analyzing said at least one personal parameter of at least one user.

39. A medical condition sensing system according to claim 38 and wherein analysis of at least one personal parameter of at least one user takes place partially at a general purpose computer at at least one user location and partially at said at least one controller computer.

40. A medical condition sensing system according to claim 38 and wherein analysis of at least one personal parameter of at least one user at a general purpose computer at at least one user location provides an analysis output which determines whether further analysis of said at least one personal parameter is carried out at said at least one controller computer.

41. A medical condition sensing system according to claim 38 and wherein at least one of said general purpose computer and said at least one controller computer serves as a backup for another one of said general purpose computer and said at least one controller computer.

42. A medical condition sensing system according to claim 1 and wherein said personal parameter measuring software includes feedback software for calibrating a measured personal parameter of a user.

43. A medical condition sensing system according to claim 42 and wherein said feedback software is operative to communicate between a general purpose computer and said controller computer over said computer network.

44. A medical condition sensing system according to claim 1 and also comprising feedback circuitry for calibrating a measured personal parameter of a user.

45. A medical condition sensing system according to claim 44 and wherein said feedback circuitry is operative to communicate between a general purpose computer and said controller computer over said computer network.

46. Apparatus for collecting medical data comprising:
   a user station connected to at least one computer remote from said user station via a computer network;
   a user interface connected to said user station, said user interface being for interfacing for gathering medical data for remote processing; and
   a calibration system at said computer remote from said user station operable to calibrate said user interface which employs communication via said at least one computer network, said calibration being for calibrating said gathering of medical data for said remote processing.

47. Apparatus for collecting medical data according to claim 46 and wherein said calibration system operates automatically without operator intervention.

48. Apparatus for collecting medical data according to claim 46 and also comprising personal parameter analysis software resident on at least one of said user station and said at least one computer for analyzing said at least one personal parameter of at least one user.

49. Apparatus for collecting medical data according to claim 48 and wherein analysis of at least one personal parameter of at least one user takes place partially at said user station and partially at said at least one computer.

50. Apparatus for collecting medical data according to claim 48 and wherein analysis of at least one personal parameter of at least one user provides an analysis output which determines whether further analysis of said at least one personal parameter is carried out at said at least one computer.

51. Apparatus for collecting medical data according to claim 48 and wherein at least one of said user station and said at least one computer serves as a backup for another one of said user station and said at least one computer.

52. A medical condition sensing system comprising:
   a multiplicity of general purpose computers disposed in user locations and being connectable via an on-line connection with a computer network to at least one controller computer remote from at least one of said user locations;
   personal parameter measuring software resident on at least one of said multiplicity of general purpose computers for measuring at least one personal parameter of at least one user; and
   personal parameter analysis software resident on at least one of said multiplicity of general purpose computers for analyzing said at least one personal parameter of at least one user and for producing an output corresponding to said analysis without an on-line connection to said controller.

53. A medical condition sensing system according to claim 52 and wherein analysis of at least one personal parameter of at least one user takes place partially at a general purpose computer at at least one user location and partially at said at least one controller computer.

54. A medical condition sensing system according to claim 52 and wherein analysis of at least one personal parameter of at least one user at a general purpose computer at at least one user location provides an analysis output which determines whether further analysis of said at least one personal parameter is carried out at said at least one controller computer.

55. A medical condition sensing system according to claim 52 and wherein at least one of said general purpose computer and said at least one controller computer serves as a backup for another one of said general purpose computer and said at least one controller computer.

56. A medical condition sensing method comprising:
  connecting a multiplicity of general purpose computers disposed in user locations via an on-line connection with a computer network to at least one controller computer remote from at least one of said user locations;
  employing personal parameter measuring software resident on at least one of said multiplicity of general purpose computers for measuring at least one personal parameter of at least one user;
  employing personal parameter reference generating software resident on at least one of said multiplicity of general purpose computers and said at least one controller computer for establishing a reference for said at least one personal parameter; and
  employing person parameter comparison software resident on at least one of said multiplicity of general purpose computers for comparing at least one currently measured personal parameter with a corresponding reference and for providing a comparison output without an on-line connection to said controller.

57. A medical condition sensing method according to claim 56 and also comprising utilizing alert indication software resident on at least one of said multiplicity of general purpose computers and said at least one controller computer for providing a generally real time alert indication to said user based at least partially on said comparison output.

58. A medical condition sensing method according to claim 57 and wherein said alert indication software is resident on said multiplicity of general purpose computers.

59. A medical condition sensing method according to claim 56 and wherein said reference is a personal parameter baseline constructed from pre-real time measurements of said personal parameter.

60. A medical condition sensing method according to claim 56 and wherein said reference is a calibration reference employing a measurement of a personal parameter based on a calibration input.

61. A medical condition sensing method according to claim 56 and wherein said reference is a calibration reference based on a calibration input.

62. A medical condition sensing method according to claim 56 and wherein said reference is a calibration reference based on a calibration input supplied from another computer via said computer network.

63. A medical condition sensing method according to claim 56 and wherein said reference is a calibration reference employing a measurement of a personal parameter based on a calibration input supplied from another computer via said computer network.

64. A medical condition sensing method according to claim 63 and wherein said personal parameter comparison software is operative to compare at least one currently measured personal parameter with said calibration reference.

65. A medical condition sensing method according to claim 56 and also comprising employing notification software resident on at least one of said multiplicity of general purpose computers and said at least one controller for transmitting a notification from one of said at multiplicity of general purpose computers to at least one other computer based on said comparison output.

66. A medical condition sensing method according to claim 56 and wherein said personal parameter comprises a heart function parameter.

67. A medical condition sensing method according to claim 56 and wherein said personal parameter comprises a blood parameter.

68. A medical condition sensing method according to claim 56 and wherein said personal parameter comprises a electrocardiogram parameter.

69. A medical condition sensing method according to claim 56 and wherein said personal parameter comprises a hearing function parameter.

70. A medical condition sensing method according to claim 56 and wherein said personal parameter comprises a skin appearance parameter.

71. A medical condition sensing method according to claim 56 and wherein said personal parameter comprises a tissue appearance parameter.

72. A medical condition sensing method according to claim 56 and wherein said personal parameter comprises an optically sensible parameter.

73. A medical condition sensing method according to claim 56 and wherein said personal parameter comprises an electrically sensible parameter.

74. A medical condition sensing method according to claim 56 and wherein said personal parameter comprises an thermally sensible parameter.

75. A medical condition sensing method according to claim 56 and wherein said personal parameter comprises an audibly sensible parameter.

76. A medical condition sensing method according to claim 56 and wherein said personal parameter comprises a chemically sensible parameter.

77. A medical condition sensing method according to claim 56 and wherein said personal parameter comparison software is operative to compare optical images of at least one body region.

78. A medical condition sensing method according to claim 56 and wherein said personal parameter measuring software is operative to measure at least one personal parameter of at least one user in response to an input supplied to the user.

79. A medical condition sensing method according to claim 56 and wherein said personal parameter measuring software includes feedback software for calibrating a measured personal parameter of a user.

80. A medical condition sensing method according to claim 56 and also comprising employing feedback circuitry for calibrating a measured personal parameter of a user.

81. A medical condition sensing method according to claim 80 and wherein said feedback software is operative to communicate between a general purpose computer and said controller computer over said computer network.

82. A medical condition sensing method according to claim 81 and wherein said feedback circuitry is operative to communicate between a general purpose computer and said controller computer over said computer network.

83. A medical condition sensing method according to claim 56 and also comprising employing software utilizing the output of at least one of said personal parameter measuring software, said personal parameter reference generating software, and said personal parameter comparison software for providing at least one of recommendations and indications to a user.

84. A medical condition sensing method according to claim 56 and also comprising accessing a manned center at least via said computer network for receiving at least some of said output of at least one of said personal parameter measuring software, said personal parameter reference generating software, said personal parameter comparison software and at least one of recommendations and indications to a user and providing health professional interaction with the user.

85. A medical condition sensing method according to claim 84 and also comprising accessing a manned center at least via said computer network for receiving at least some of said output of at least one of said personal parameter measuring software, said personal parameter reference generating software, said personal parameter comparison software and at least one of recommendations and indications to a user and providing health professional interaction with the user.

86. A medical condition sensing method according to claim 85 and wherein at least one of said recommendations and indications as well as the criteria therefor is determinable by a user s health professional by transmitting instructions to at least one of said controller computer and said general purpose computer via said computer network.

87. A medical condition sensing method according to claim 86 and wherein at least one of said recommendations and indications as well as the criteria therefor is determinable by a user's health professional by transmitting instructions to at least one of said controller computer and said general purpose computer via said computer network.

88. A medical condition sensing method according to claim 85 and wherein said manned center employs a personal physician of the user and communicates with him via through at least one of telephone and data links via at least one of wired and wireless communication media.

89. A medical condition sensing method according to claim 88 and wherein analysis of at least one personal parameter of at least one user at a general purpose computer at at least one use location provides an analysis output which determines whether further analysis of said at least one personal parameter is carried out at said at least one controller computer.

90. A medical condition sensing method according to claim 88 and wherein at least one of said general purpose computer and said at least one controller computer serves as a backup for another one of said general purpose computer and said at least one controller computer.

91. A medical condition sensing method according to claim 56 and also comprising employing personal parameter analysis software resident on at least one of said multiplicity of general purpose computers and said at least one controller computer for analyzing said at least one personal parameter of at least one user.

92. A medical condition sensing method according to claim 91 and wherein analysis of at least one personal parameter of at least one user takes place partially at a general purpose computer at at least one user location and partially at said at least one controller computer.

93. Apparatus for collecting medical data comprising:
 a general purpose computer;
 a user interface connected to said computer;
 a recording and storage facility for recording and storing at least one baseline result received by said user station using said user interface from at least a first test taken at least a first time; and
 a comparison facility for receiving at least one subsequent result received by said user station using said user interface from at least a second test, similar to said first test, taken at at least a second time, later than said first time, comparing said at least second test with said at least first test, applying a threshold to a comparison result and providing an indication in response to exceedance of said threshold.

94. A user interface assembly suitable for use in apparatus for collecting medical data including a general purpose computer, the user interface assembly comprising:
 a user interface coupled to said user station for use in collecting medical data from a subject;
 software usable by said general purpose computer and providing at least the following functionality:
  a recording and storage functionality for recording and storing at least one baseline result received by said general purpose computer via said user interface from at least a first test taken at at least a first time; and
  a comparison facility for receiving at least one subsequent result received by said general purpose computer using said user interface from at least a second test, similar to said first test, taken at at least a second time, later than said first time, comparing said at least second test with said at least first test, applying a threshold to a comparison result, said threshold being selected based on said first test, and providing an indication in response to exceedance of said threshold.

95. A user interface method suitable for use in apparatus for collecting medical data including a general purpose computer, the user interface method comprising:
 coupling a user interface to said user station for collecting medical data from a subject;
 employing software providing at least the following functionality:
  recording and storing at least one baseline result received by said general purpose computer via said user interface from at least a first test taken at at least a first time; and
  receiving at last one subsequent result using said user interface from at least a second test, similar to said fist test, taken at at least a second time, later than said fist time, comparing said at least second test with said at least first test, applying a threshold to a comparison result, said threshold being selected based on said first test, and proving an indication in response to exceedance of said threshold.

96. A user interface method suitable for use in apparatus for collecting medical data for remote processing including a user station connected to at least one computer remote from said user station via a computer network, said user interface method comprising:
 coupling a user interface to said user station for use in collecting medical data from a subject; and
 employing software to control the operation of said user interface and to communicate via said computer network with said at least one computer remote from said user station, said software being further operable to:
  communicate data required for calibration of said medical data collecting, from said user station to said remote computer via said network and
  to support calibration of said medical data collecting at said user station from said remote computer via said network.

97. A method for collecting medical data for remote processing comprising:
 connecting a user station to at least one computer remote from said user station via a computer network;
 connecting a user interface to said user station, said user interface being for collecting medical data at said user station for said remote processing; and calibrating said user interface at said user station from said remote computer by employing communication via said at least one computer network, thereby to obtain calibrated data for said remote processing.

98. A method for collecting medical data according to claim 97 and wherein said calibrating step operates automatically without operator intervention.

99. A method for collecting medical data according to claim 97 and also comprising employing personal parameter analysis software resident on at least one of said user station and said at least one computer for analyzing said at least one personal parameter of at least one user.

100. A method for collecting medical data according to claim 99 and wherein analysis of at least one personal parameter of at least one user provides an analysis output which determines whether further analysis of said at least one personal parameter is carried out at said at least one computer.

101. A method for collecting medical data according to claim 99 and wherein analysis of at least one personal parameter of at least one user takes place partially at said user station and partially at said at least one computer.

102. A method for collecting medical data according to claim 99 and wherein at least one of said user station and said at least one computer serves as a backup for another one of said user station and said at least one computer.

103. A method for collecting medical data comprising:

providing a general purpose computer;

connecting a user interface to said computer;

recording and storing at least one baseline result received by said user station using said user interface from at least a first test taken at least a first time; and receiving at least one subsequent result received by said user station using said user interface from at least a second test, similar to said first test, taken at at least a second time, later than said first time, comparing said at least second test with said at least first test, applying a threshold to a comparison result and providing an indication in response to exceedance of said threshold.

104. A medical condition sensing method comprising:

connecting a multiplicity of general purpose computers disposed in user locations via an on-line connection with a computer network to at least one controller computer remote from at least one of said user locations;

employing personal parameter measuring software resident on at least one of said multiplicity of general purpose computers for measuring at least one personal parameter of at least one user; and employing personal parameter analysis software resident oil at least one of said multiplicity of general purpose computers for analyzing said at least one personal parameter of at least one user and for producing an output corresponding to said analysis without an on-line connection to said controller.

105. A medical condition sensing method according to claim 104 and wherein analysis of at least one personal parameter of at least one user at a general purpose computer at at least one user location provides an analysis output which determines whether further analysis of said at least one personal parameter is carried out at said at least one controller computer.

106. A medical condition sensing method according to claim 104 and wherein at least one of said general purpose computer and said at least one controller computer serves as a backup for another one of said general purpose computer and said at least controller computer.

107. A medical condition sensing method according to claim 104 and wherein analysis of at least one personal parameter of at least one user takes place partially at a general purpose computer at at least one use location and partially at said at least one controller computer.

108. A user interface assembly suitable for use in apparatus for collecting medical data including a user station connected to at least one computer remote from said user station via a computer network, said user interface assembly comprising:

a user interface coupled to said user station for use in collecting medical data from a subject;

software usable by said user station to control the operation of said user interface and to communicate via said computer network with said at least one computer remote from said user station; and wherein said software is useful at least to communicate data required for calibration of at least one of said user interface and said user station.

* * * * *